United States Patent
Imaizumi et al.

(10) Patent No.: US 7,179,222 B2
(45) Date of Patent: Feb. 20, 2007

(54) FLUORESCENT ENDOSCOPE SYSTEM ENABLING SIMULTANEOUS ACHIEVEMENT OF NORMAL LIGHT OBSERVATION BASED ON REFLECTED LIGHT AND FLUORESCENCE OBSERVATION BASED ON LIGHT WITH WAVELENGTHS IN INFRARED SPECTRUM

(75) Inventors: Katsuichi Imaizumi, Shibuya-ku (JP); Kazunari Nakamura, Shibuya-ku (JP)

(73) Assignee: Olympus Corporation (JP)

( * ) Notice: Subject to any disclaimer, the term of this patent is extended or adjusted under 35 U.S.C. 154(b) by 457 days.

(21) Appl. No.: 10/767,755

(22) Filed: Jan. 28, 2004

(65) Prior Publication Data
US 2004/0186351 A1    Sep. 23, 2004

Related U.S. Application Data

(60) Continuation of application No. 09/533,366, filed on Mar. 22, 2000, now abandoned, which is a division of application No. 08/974,531, filed on Nov. 19, 1997, now Pat. No. 6,293,911.

(30) Foreign Application Priority Data

| Nov. 20, 1996 | (JP) | ................................. 8-309692 |
| Nov. 25, 1996 | (JP) | ................................. 8-313876 |
| May 23, 1997 | (JP) | ................................. 9-133959 |

(51) Int. Cl.
*A61B 1/045* (2006.01)
*A61B 1/05* (2006.01)

(52) U.S. Cl. ...................... 600/109; 600/160; 600/118; 600/178

(58) Field of Classification Search ................ 600/160, 600/109, 178, 407, 476, 478, 473, 118; 348/65, 348/68, 69, 70
See application file for complete search history.

(56) References Cited

U.S. PATENT DOCUMENTS

| 4,685,451 A | 8/1987 | Ando |
| 4,821,117 A | 4/1989 | Sekiguchi |
| 4,885,634 A | 12/1989 | Yabe |
| 5,078,150 A | 1/1992 | Hara et al. |
| 5,131,398 A | 7/1992 | Alfano et al. |
| 5,187,572 A | 2/1993 | Nagamura et al. |
| 5,196,928 A | 3/1993 | Karasawa et al. |

(Continued)

FOREIGN PATENT DOCUMENTS

JP          62217216          9/1987

(Continued)

*Primary Examiner*—John P Leubecker
(74) *Attorney, Agent, or Firm*—Ostrolenk, Faber, Gerb & Soffen, LLP

(57) ABSTRACT

A visible light spectrum and a fluorescent light spectrum are received by a variable gain solid state imaging device provided to an endoscope. The variable gain solid state imaging device can be said to lower amplification levels for easily observed visible light spectrum, and higher amplification levels for low intensity fluorescent light spectrum observation. By varying the gain of the imaging device with the different spectrums, an object observed with the endoscope is displayed with approximately similar brightness in each white spectrum. A controller coupled to endoscope system switches different light spectrum to irradiate the observed object, while controlling amplification of the image device. The endoscope provides enhanced image detail to improve diagnosis and treatment of observed abnormal objects.

49 Claims, 32 Drawing Sheets

U.S. PATENT DOCUMENTS

| | | |
|---|---|---|
| 5,255,087 A | 10/1993 | Nakamura et al. |
| 5,337,340 A | 8/1994 | Hynecek |
| 5,412,705 A | 5/1995 | Snoeren |
| 5,507,287 A | 4/1996 | Palcic et al. |
| 5,528,059 A | 6/1996 | Isogai |
| 5,590,660 A | 1/1997 | MacAulay et al. |
| 5,608,451 A | 3/1997 | Konno |
| 5,699,798 A | 12/1997 | Hochman et al. |
| 5,713,364 A | 2/1998 | DeBaryshe et al. |
| 5,716,595 A | 2/1998 | Goldenberg |
| 5,749,830 A | 5/1998 | Kaneko et al. |
| 5,772,580 A | 6/1998 | Utsui et al. |
| 5,827,190 A | 10/1998 | Palcic et al. |
| 5,968,479 A | 10/1999 | Ito |
| 5,987,261 A | 11/1999 | Sugahara |
| 6,099,466 A * | 8/2000 | Sano et al. .................. 600/160 |

FOREIGN PATENT DOCUMENTS

| | | |
|---|---|---|
| JP | 7059783 | 3/1995 |
| JP | 7155292 | 6/1995 |
| JP | 7204156 | 8/1995 |
| JP | 639464 | 2/1998 |
| WO | 9525460 | 9/1995 |
| WO | 9623525 | 8/1996 |

* cited by examiner

FIG.5
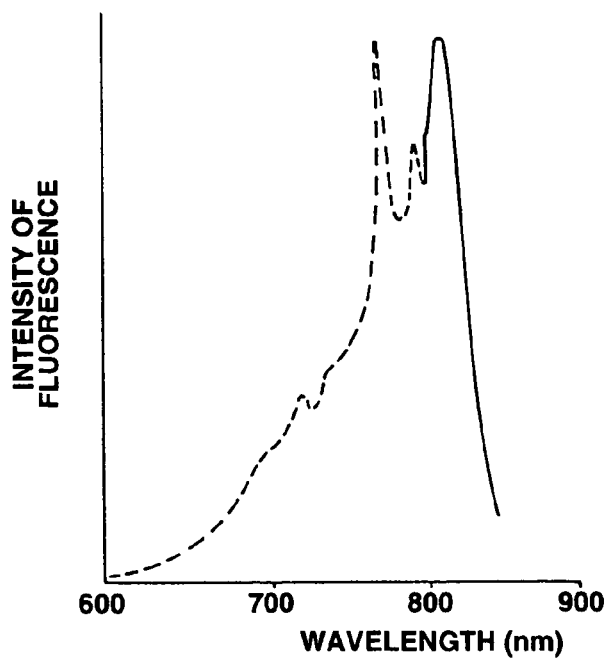
FIG.6
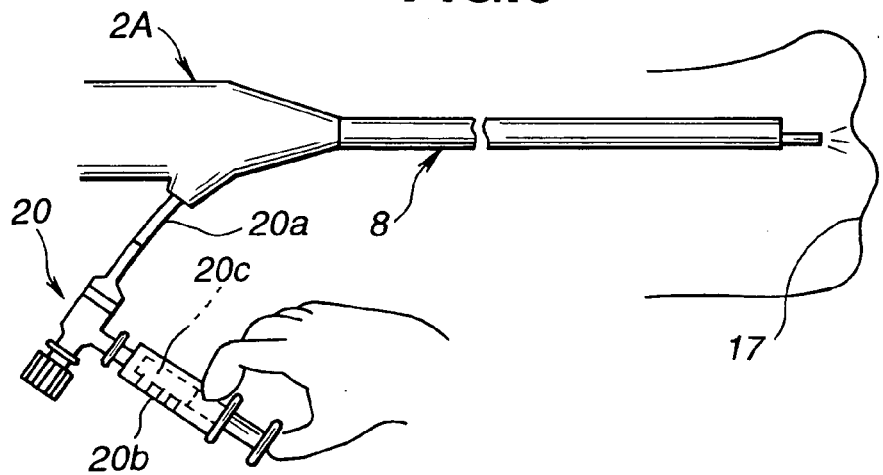
FIG.9

6a  6b 6a  6b

6c

6a

6b

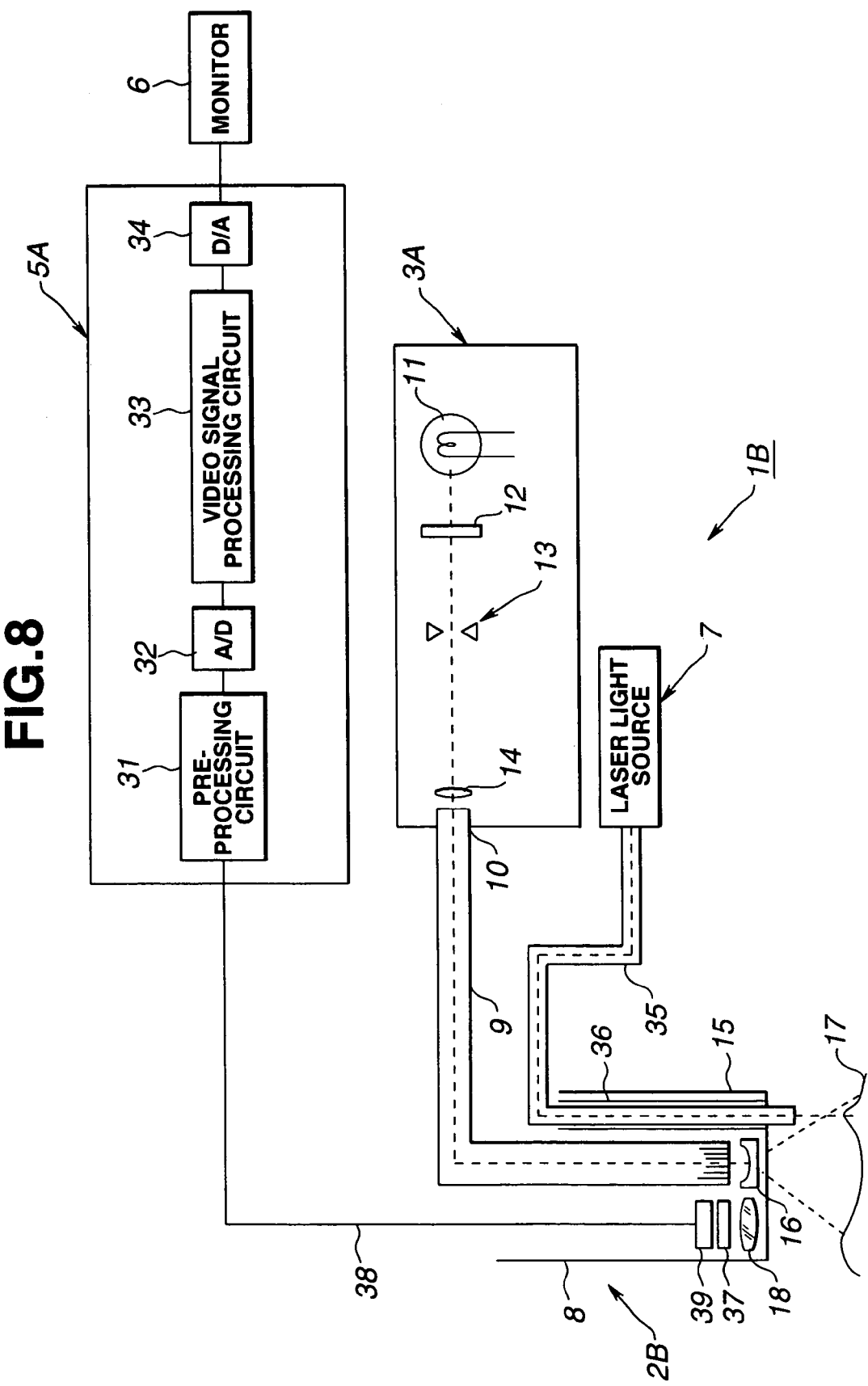

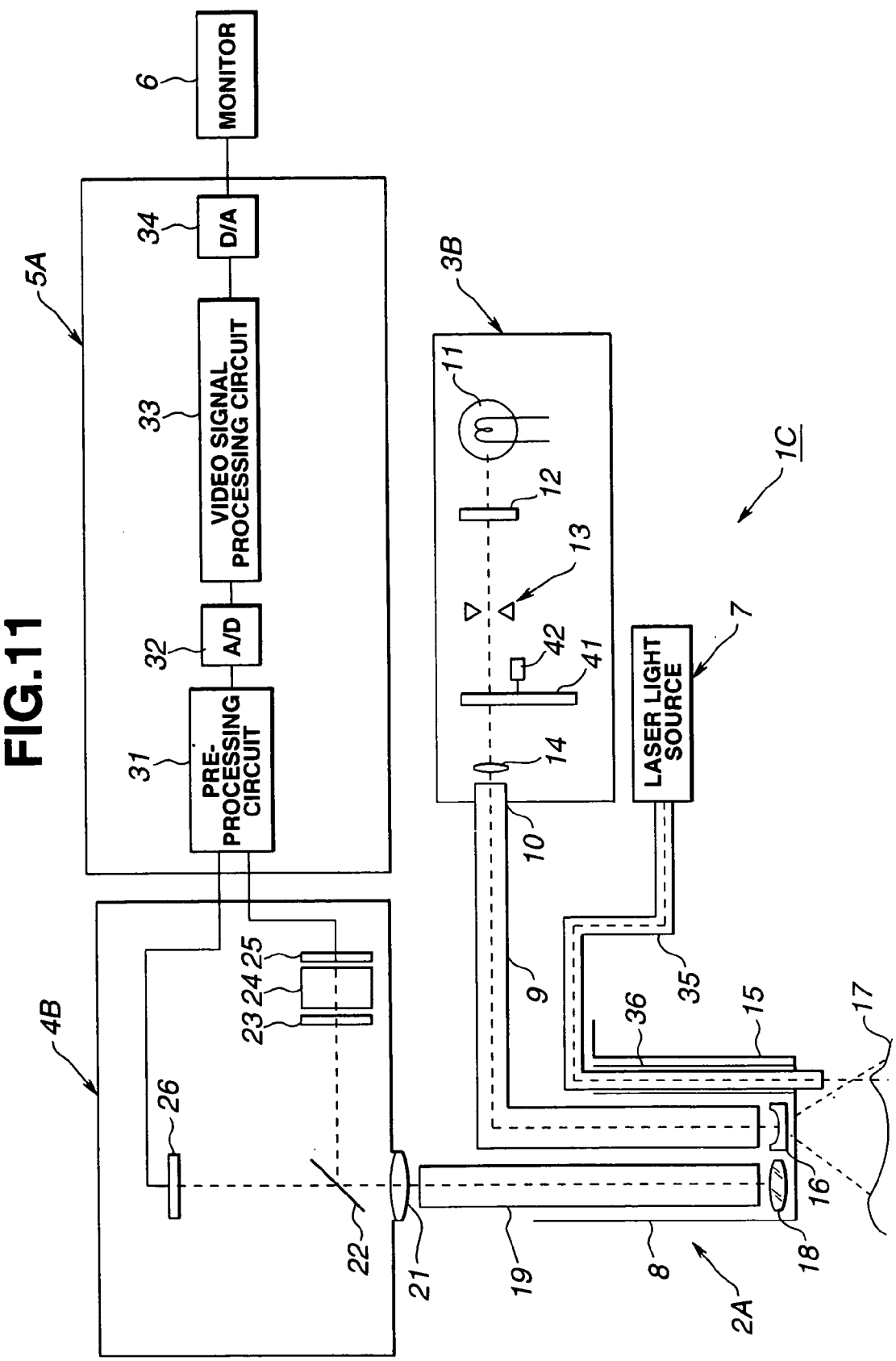

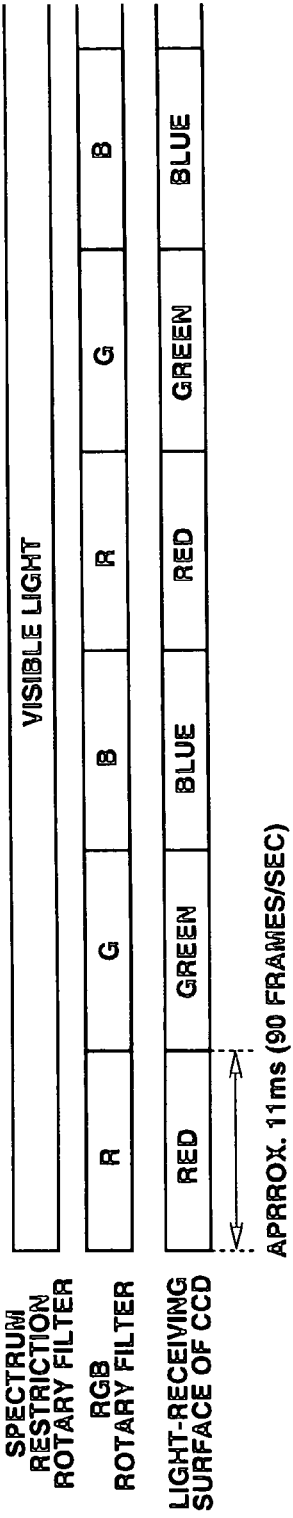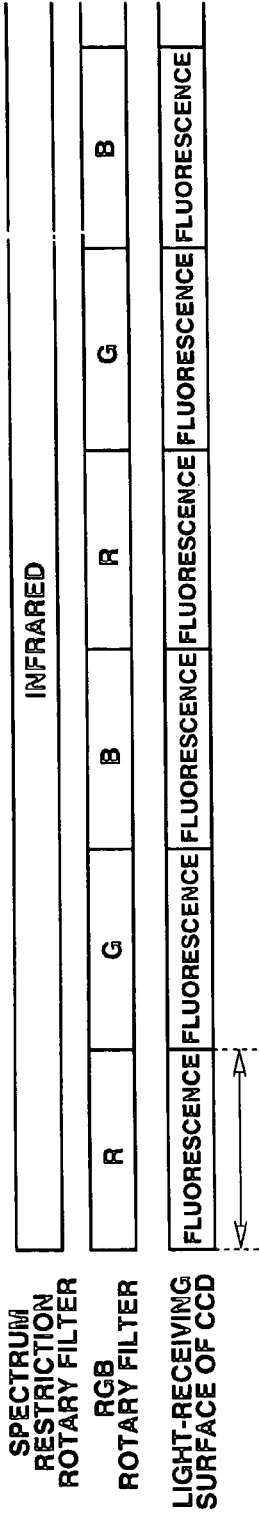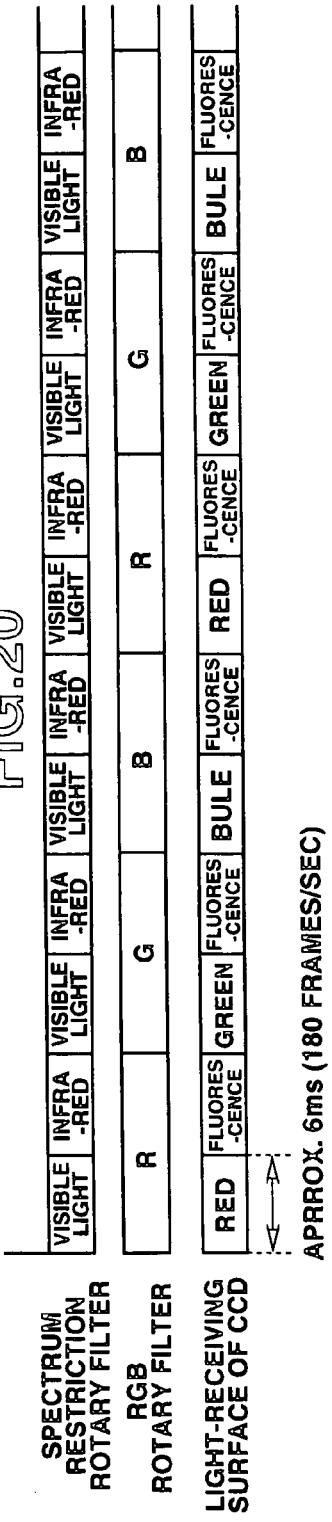

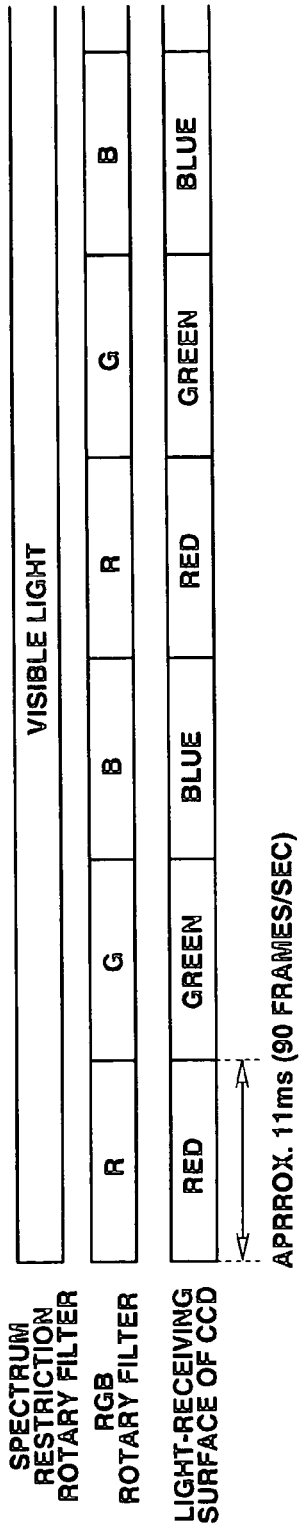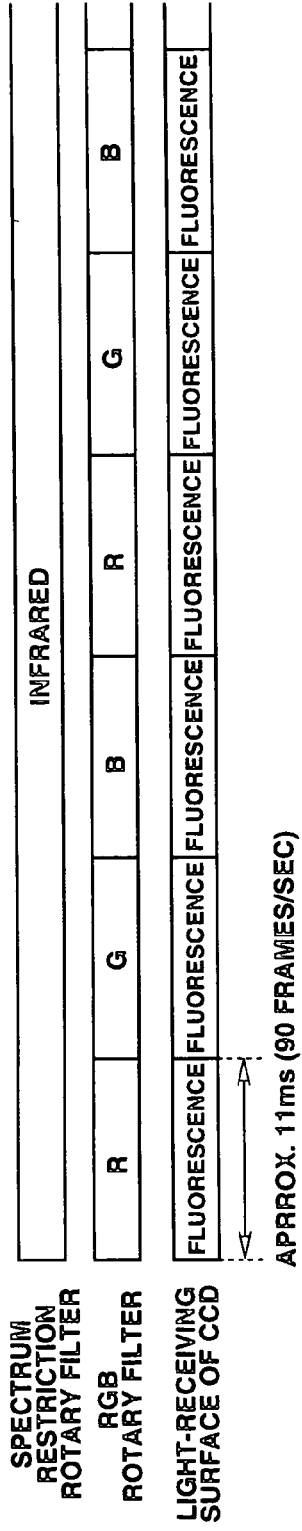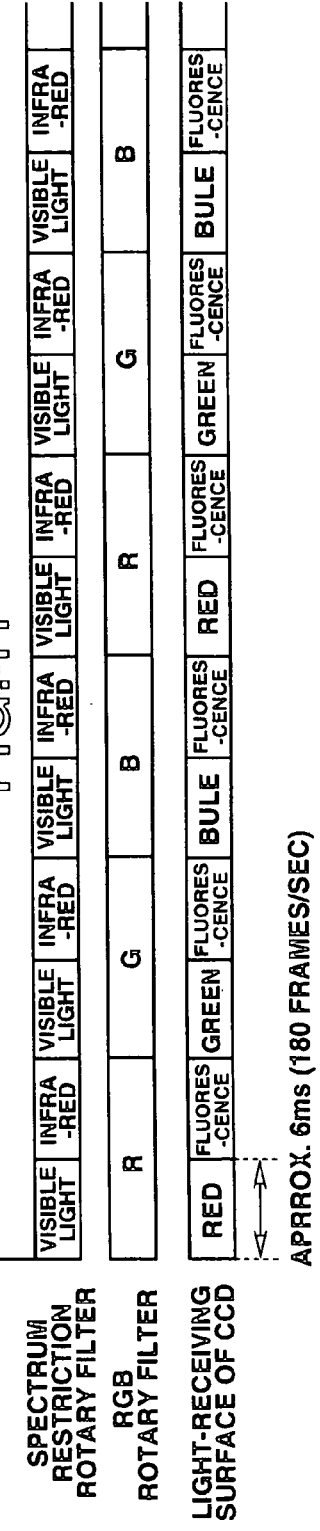

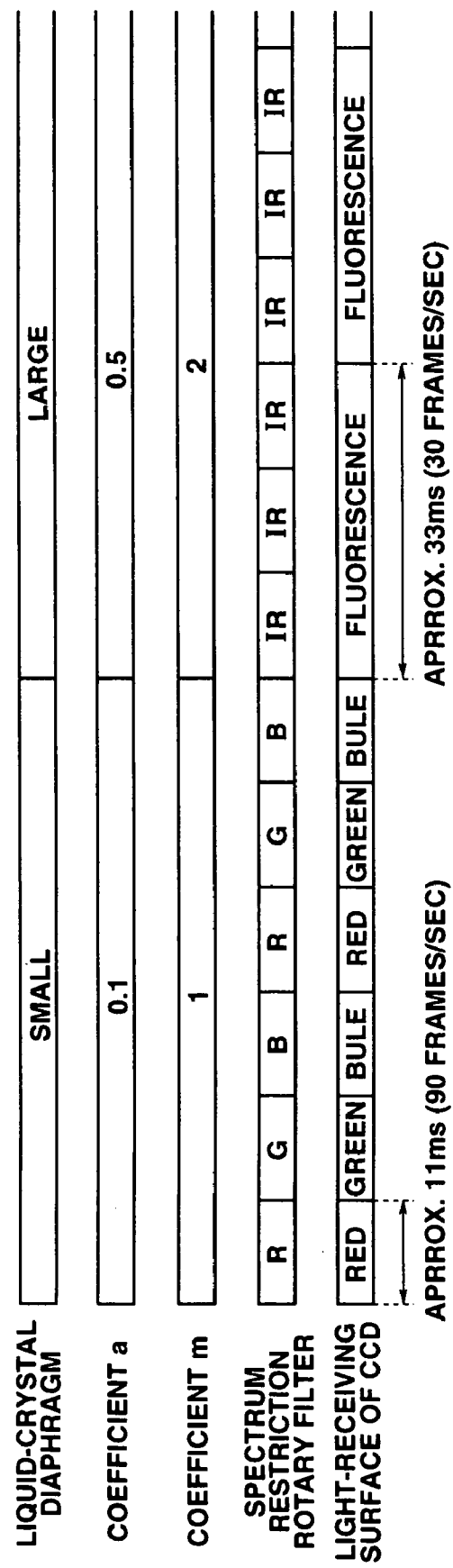

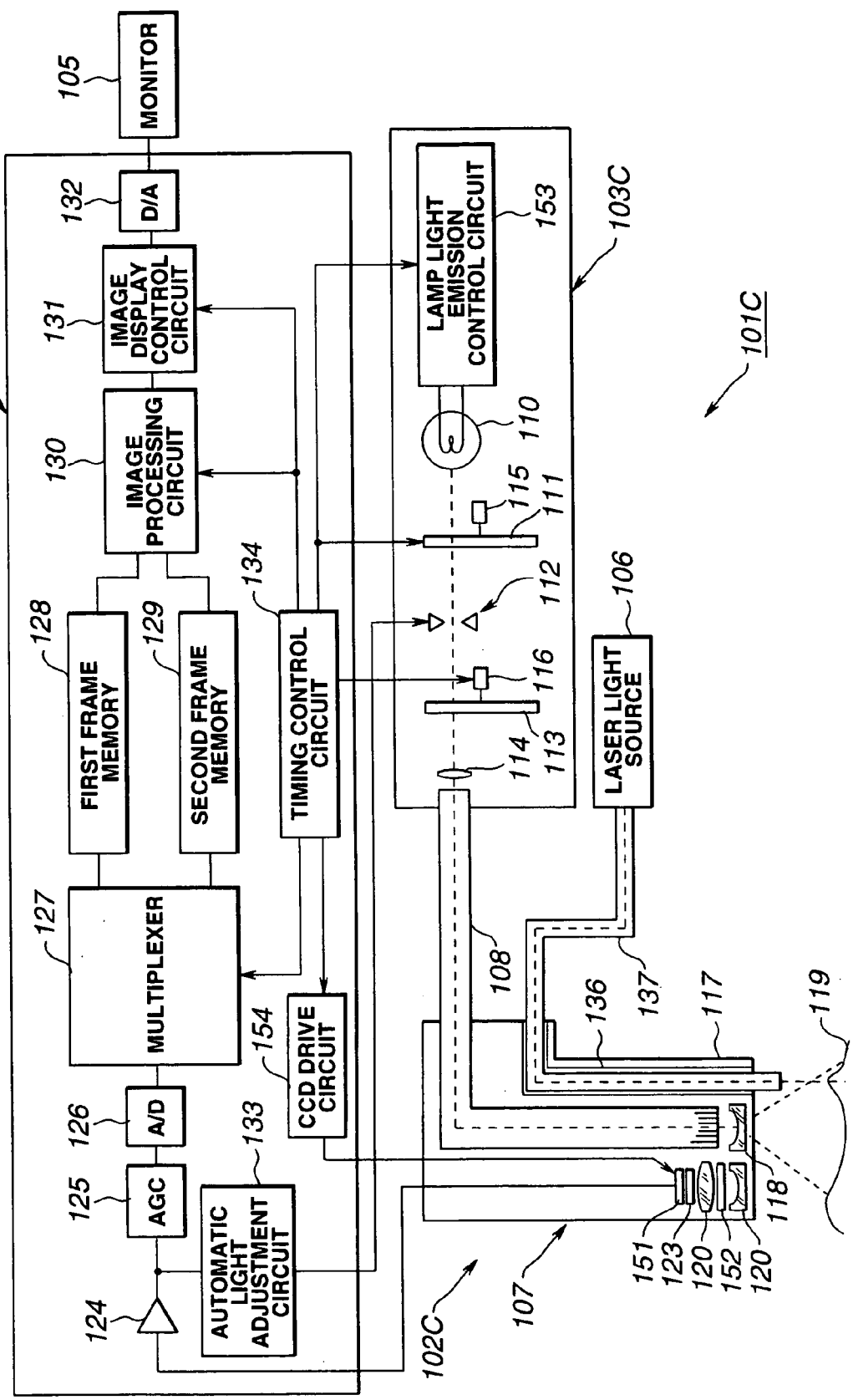

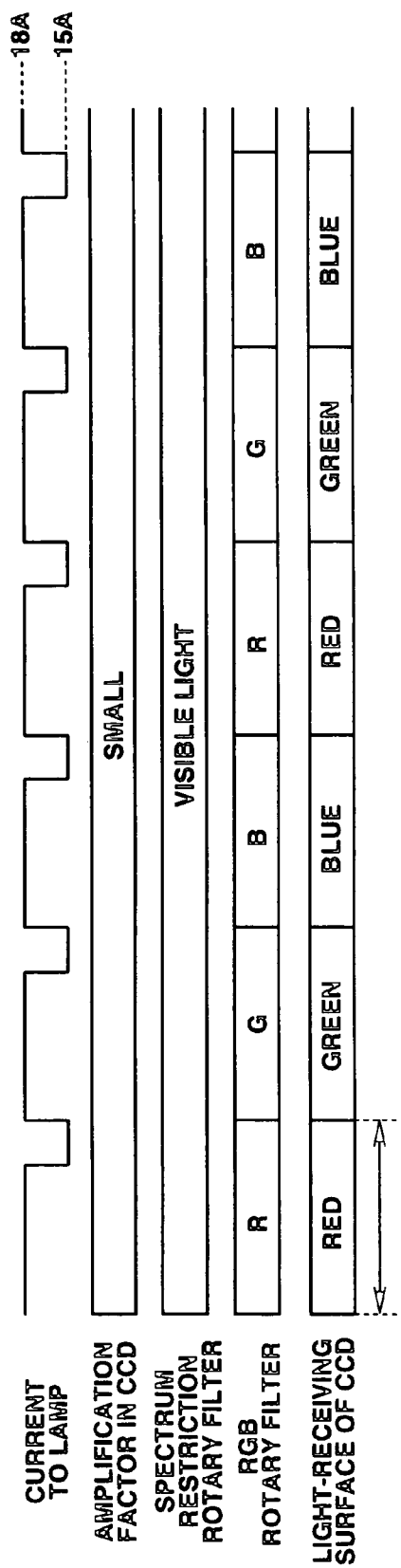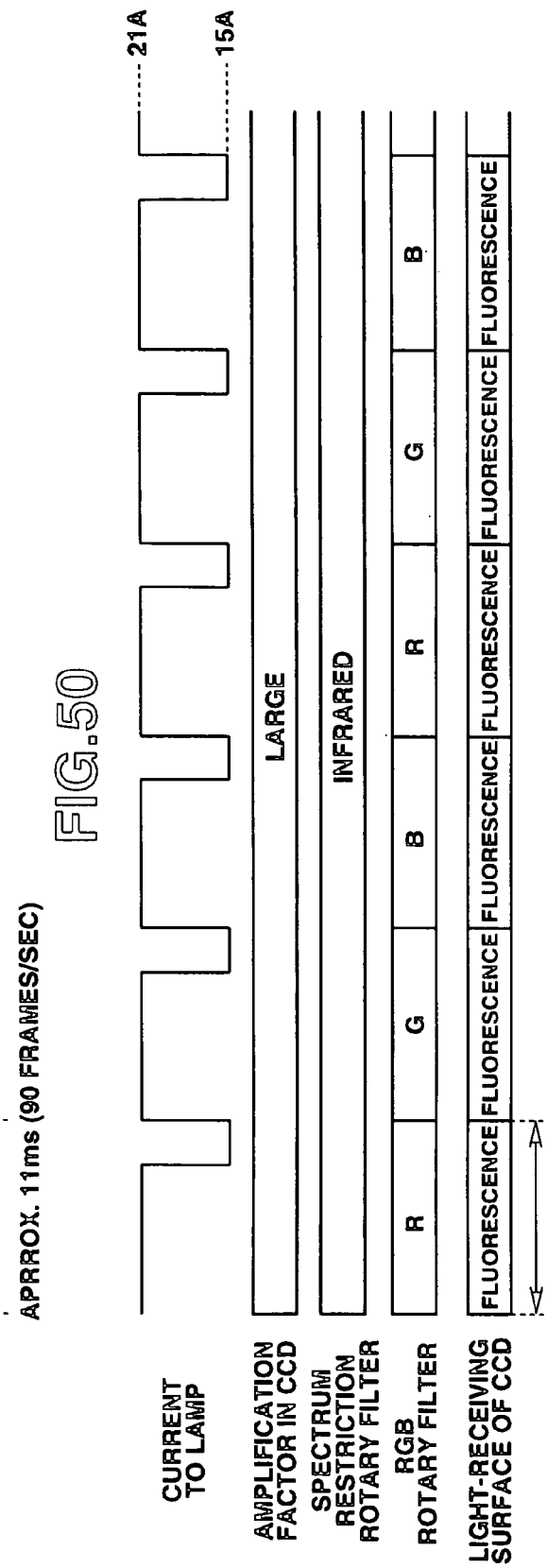

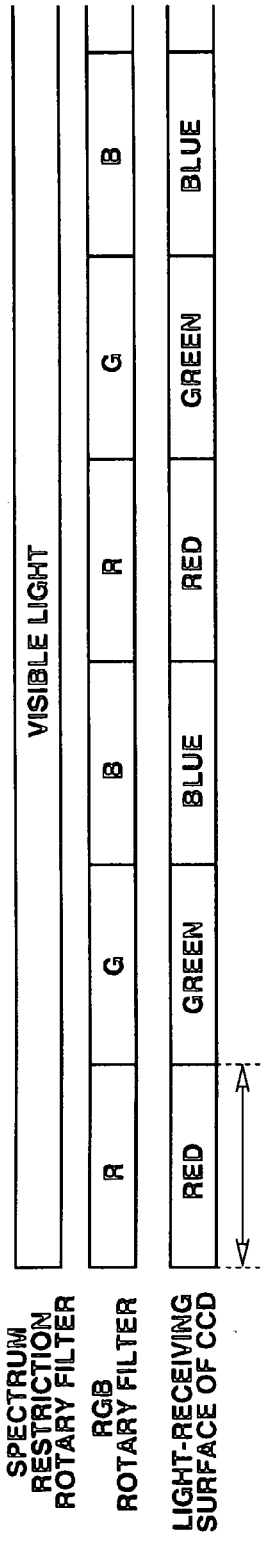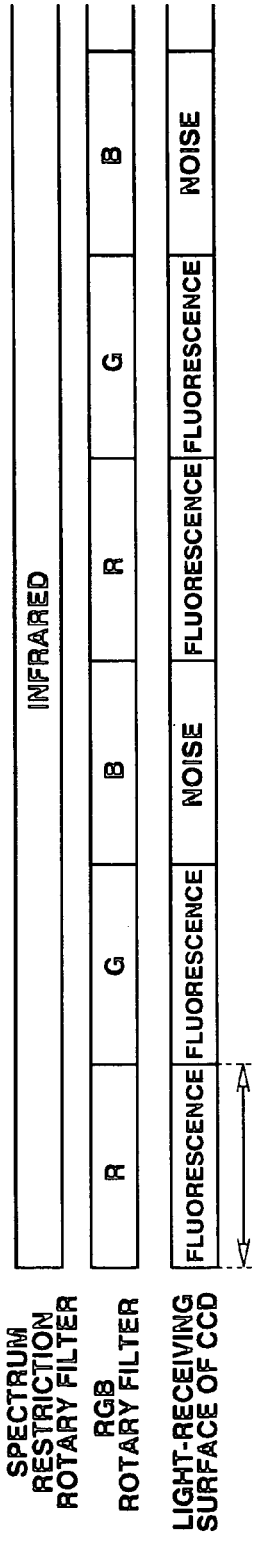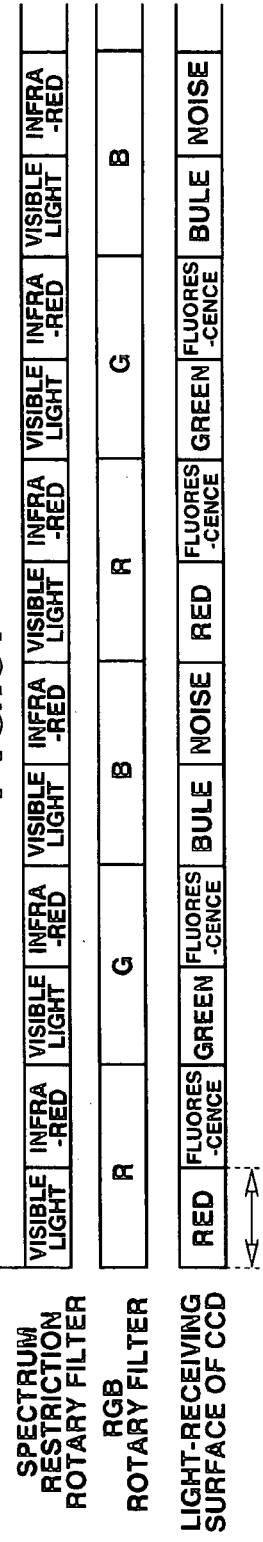

FIG.59

| 1/35 | 1/35 | 1/35 | 1/35 | 1/35 |
|------|------|------|------|------|
| 1/35 | 2/35 | 2/35 | 2/35 | 1/35 |
| 1/35 | 2/35 | 2/35 | 2/35 | 1/35 |
| 1/35 | 2/35 | 2/35 | 2/35 | 1/35 |
| 1/35 | 1/35 | 1/35 | 1/35 | 1/35 |

FIG.60

| 0 | 1   | 1   | 1   | 0 |
|---|-----|-----|-----|---|
| 1 | -2  | -10 | -2  | 1 |
| 1 | -10 | 37  | -10 | 1 |
| 1 | -2  | -10 | -2  | 1 |
| 0 | 1   | 1   | 1   | 0 |

FLUORESCENT ENDOSCOPE SYSTEM ENABLING SIMULTANEOUS ACHIEVEMENT OF NORMAL LIGHT OBSERVATION BASED ON REFLECTED LIGHT AND FLUORESCENCE OBSERVATION BASED ON LIGHT WITH WAVELENGTHS IN INFRARED SPECTRUM

CROSS-REFERENCE TO RELATED APPLICATIONS

This is a continuation of U.S. patent application Ser. No. 09/533,366, filed Mar. 22, 2000, now abandoned which is a divisional of U.S. patent application Ser. No. 08/974,531, filed Nov. 19, 1997 now U.S. Pat. No. 6,293,911 of in the name of Katsuichi Imaizumi et al. and entitled FLUORESCENT ENDOSCOPE SYSTEM ENABLING SIMULTANEOUS ACHIEVEMENT OF NORMAL LIGHT OBSERVATION BASED ON REFLECTED LIGHT AND FLUORESCENCE OBSERVATION BASED ON LIGHT WITH WAVELENGTHS IN INFRARED SPECTRUM.

BACKGROUND OF THE INVENTION

1. Field of the Invention

The present invention relates to a fluorescent endoscope system for simultaneously producing a reflected-light image depicted by reflected light with wavelengths in the visible spectrum and a fluorescence image depicted by infrared radiation.

2. Description of the Related Art

In recent years, an endoscope of which insertional part is inserted into a body cavity for the purpose of observing the alimentary canal extending from the esophagus through the stomach to the small and large intestines or the trachea extending to the lung, or if necessary, of conducting various kinds of treatments using therapeutic instruments inserted into a therapeutic instrument channel has been put to use. In particular, an electronic endoscope having an electronic imaging device such as a charge coupled device (CCD) has been widely adopted because an image can be displayed on a monitor and an operator of the endoscope is little fatigued with manipulation.

Recently, a modality in which a fluorescent substance having an affinity for a lesion such as a carcinoma is administered to a subject to be examined in advance, excitation light for exciting the fluorescent substance is irradiated, and fluorescence emanating from the fluorescent substance is detected.

According to the modality, since intense fluorescence is radiated from a lesion, the presence of the lesion can be judged from the brightness of a fluorescence image. A system as adopting the modality is, for example, a system, disclosed in Japanese Unexamined Patent Publication No. 59-40830, for detecting fluorescence emanating from hematoporphyrin that is a fluorescent substance.

In the system disclosed in Japanese Unexamined Patent Publication No. 59-40830, control is provided so that pulsed laser light for excitation and white light for normal observation can be irradiated selectively. Japanese Unexamined Patent Publication No. 7-59783 has disclosed a system enabling observation of fluorescent substances such as chlorin and pheophorbide. In the system disclosed in Japanese Unexamined Patent Publication No. 7-59783, light suitable for exciting a fluorescent substance and light suitable for normal light observation (white light) are irradiated while being switched by a rotary filter.

Prior methods for exciting fluorescent substances is irradiated, light with relatively short wavelengths of about 405 nm is irradiated. When light with the wavelengths is irradiated to a living tissue, the living tissue itself fluoresces. Unless an apparatus exhibiting high spectroscopic precision such as a spectrometer is employed, it is hard to distinguish self-fluorescence from fluorescence emanating from a fluorescent substance.

The transmittance of light with short wavelengths relative to a living tissue is so poor that a system using hematoporphyrin to be excited by light with short wavelengths may miss the presence of a substance fluorescing in a deep subcutaneous region.

In the prior art, excitation light and white light are irradiated while being switched temporally. Consequently, during irradiation of excitation light, a fluorescence image alone can be produced. During irradiation of while light, a normal light image alone can be produced. There is a large difference in time between the fluorescence image and normal image.

OBJECTS AND SUMMARY OF THE INVENTION

The first object of the present invention is to provide a fluorescent endoscope system enabling observation of a fluorescent substance that is excited to fluoresce by means of light with wavelengths in an infrared spectrum exhibiting good transmittance relative to a living tissue, such as, an antibody labeled by indocyanine green, capable of nullifying the influence of self-fluorescence, and capable of preventing a lesion in a deep subcutaneous region from being missed.

The second object of the present invention is to provide a fluorescent endoscope system in which since a reflected-light image depicted by reflected light and a fluorescence image can be produced simultaneously, there is no difference in time between the images, which enables easy diagnose of a lesion, and of which endoscope can be oriented easily.

A fluorescent endoscope system comprises: an endoscope having an elongated insertional part capable of being inserted into a living body; a light source means for simultaneously irradiating excitation light with wavelengths in a first infrared spectrum, which causes a fluorescent substance to be administered to a living tissue to fluoresce, and light with wavelengths in the visible spectrum; a separating means for separating fluorescence with wavelengths in a second infrared spectrum including at least part of the wavelengths of the fluorescent substance and different from the first infrared spectrum, from light stemming from the living tissue; a first imaging means for forming an image depicted by the fluorescence separated by the separating means; and a second imaging means for forming an image depicted by light with wavelengths in the visible spectrum. Owing to these components, self-fluorescence can be cut off together with light with wavelengths in the infrared spectrum that are longer than the wavelengths of the self-fluorescence. Fluorescence observation of an object using a fluorescent substance that is characteristic of good transmittance and ready accumulation in a lesion, such as, an antibody labeled by indocyanine green can be carried out. Fluorescence emanating form a lesion in a deep subcutaneous region in which the fluorescent substance is accumulated can be observed but will not be missed.

BRIEF DESCRIPTION OF THE DRAWINGS

FIGS. 1 to 7 relate to the first embodiment of the present invention;

FIG. 1 is a diagram showing the overall configuration of a fluorescent endoscope system in accordance with the first embodiment;

FIG. 2 is a diagram showing the spectroscopic characteristic of a bandpass filter concerning transmission;

FIG. 3 is a diagram showing the spectroscopic characteristic of a dichroic mirror concerning transmission;

FIG. 4 is a diagram showing the spectroscopic characteristic of an excitation light cutoff filter concerning of transmission;

FIG. 5 is a diagram showing the characteristic of an antibody labeled by indocyanine green concerning excitation and fluorescence;

FIG. 6 is a diagram schematically showing a scene in which a fluorescent substance that is an antibody labeled by indocyanine green is dispersed;

FIGS. 8 to 10 relate to the second embodiment of the present invention;

FIG. 8 is a diagram showing the overall configuration of a fluorescent endoscope system in accordance with the second embodiment;

FIG. 9 is a diagram showing the structure of a mosaic filter;

FIG. 10 is a diagram showing the spectroscopic characteristics of the mosaic filter concerning transmission;

FIGS. 11 to 13 relate to the third embodiment of the present invention;

FIG. 11 is a diagram showing the overall configuration of a fluorescent endoscope system in accordance with the third embodiment;

FIG. 12 is a diagram showing the structure of an RGB rotary filter;

FIG. 13 is a diagram showing the spectroscopic characteristics of the RGB filter concerning transmission;

FIGS. 14 to 20 relate to the fourth embodiment of the present invention;

FIG. 14 is a diagram showing the overall configuration of a fluorescent endoscope system in accordance with the fourth embodiment;

FIG. 15 is a diagram showing the structure of a spectrum restriction rotary filter;

FIG. 16 is a diagram showing the spectroscopic characteristics of a visible light transmission filter and infrared light transmission filter concerning transmission;

FIG. 17 is a diagram showing the spectroscopic characteristic of an excitation light cutoff filter concerning transmission;

FIG. 18 is an explanatory diagram showing operations in normal light observation;

FIG. 19 is an explanatory diagram showing operations in fluorescence observation;

FIG. 20 is an explanatory diagram showing operations in normal light/fluorescence simultaneous observation;

FIG. 21 is a diagram showing the overall configuration of a fluorescent endoscope system in accordance with the fifth embodiment;

FIG. 22 is a diagram showing the configuration of a pre-processing circuit;

FIG. 23 is a diagram showing the configuration of a video signal processing circuit;

FIG. 24 is a diagram showing the characteristic of hemoglobin concerning absorption;

FIG. 25 is an explanatory diagram showing an example of a screen display on a monitor when normal light/fluorescent marker observation is selected;

FIG. 26 is a diagram showing the overall configuration of a fluorescent endoscope system in accordance with the sixth embodiment;

FIG. 27 is a diagram showing the configuration of a video signal processing circuit;

FIG. 28 is a diagram showing the spectroscopic characteristic of a second dichroic mirror concerning transmission;

FIG. 29 is a diagram showing an image displayed when fluorescence synthesis observation is selected;

FIG. 30 is a diagram showing an image displayed when normal light/fluorescence two-screen observation is selected;

FIGS. 31 to 41 relate to the seventh embodiment of the present invention;

FIG. 31 is a diagram showing the overall configuration of a fluorescent endoscope system in accordance with the seventh embodiment;

FIG. 32 is a diagram showing the structure of a spectrum restriction rotary filter;

FIG. 33 is a diagram showing the spectroscopic characteristics of the spectrum restriction rotary filter concerning transmission;

FIG. 34 is a diagram showing the structure of an RGB rotary filter;

FIG. 35 is a diagram showing the spectroscopic characteristics of the RGB rotary filter concerning transmission;

FIG. 36 is a diagram showing the structure of a filter diaphragm;

FIG. 37 is a diagram showing the spectroscopic characteristic of the filter diaphragm concerning transmission;

FIG. 38 is a diagram showing the spectroscopic characteristic of an excitation light cutoff filter concerning transmission;

FIG. 39 is an explanatory diagram concerning operations in normal light observation;

FIG. 40 is an explanatory diagram concerning operations in fluorescence observation;

FIG. 41 is an explanatory diagram concerning operations in normal light/fluorescence simultaneous observation;

FIG. 42 is a diagram showing the overall configuration of a fluorescent endoscope system in accordance with the eighth embodiment;

FIG. 43 is a diagram showing the structure of a parallel rotary filter;

FIG. 44 is a diagram showing the spectroscopic characteristics of the parallel rotary filter concerning transmission;

FIG. 45 is a diagram showing the structure of a liquid-crystal diaphragm;

FIG. 46 is a diagram showing the configuration of an integration circuit;

FIG. 47 is an explanatory diagram concerning operations in accordance with the ninth embodiment;

FIGS. 48 to 51 relate to the tenth embodiment of the present invention;

FIG. 48 is a diagram showing the overall configuration of a fluorescent endoscope system in accordance with the tenth embodiment;

FIG. 49 is an explanatory diagram concerning operations in normal light observation;

FIG. 50 is an explanatory diagram concerning operations in fluorescence observation;

FIG. 51 is an explanatory diagram concerning operations in normal light/fluorescence simultaneous observation;

FIGS. 52 to 57 relate to the eleventh embodiment of the present invention;

FIG. 52 is a diagram showing the overall configuration of a fluorescent endoscope system in accordance with the eleventh embodiment;

FIG. 53 is a diagram showing the structure of an RGB rotary filter;

FIG. 54 is a diagram showing the spectroscopic characteristics of the RGB rotary filter;

FIG. 55 is an explanatory diagram concerning operations in normal light observation;

FIG. 56 is an explanatory diagram concerning operations in fluorescence observation;

FIG. 57 is an explanatory diagram concerning operations in normal light/fluorescence simultaneous observation;

FIGS. 58 to 60 relate to the twelfth embodiment of the present invention;

FIG. 58 is a diagram showing the overall configuration of a fluorescent endoscope system in accordance with the twelfth embodiment;

FIG. 59 is a diagram showing coefficients set in a spatial filter for fluorescence observation; and FIG. 60 is a diagram showing coefficients set in a spatial filter for normal light observation.

DESCRIPTION OF PREFERRED
EMBODIMENTS OF THE INVENTION

Embodiments of the present invention will be described with reference to the drawings below.

An object of an embodiment is to produce a visible-light image and a fluorescence image depicted by infrared light emanating from an antibody labeled by indocyanine green with high image quality and with no difference in time between the images.

Figure 1:
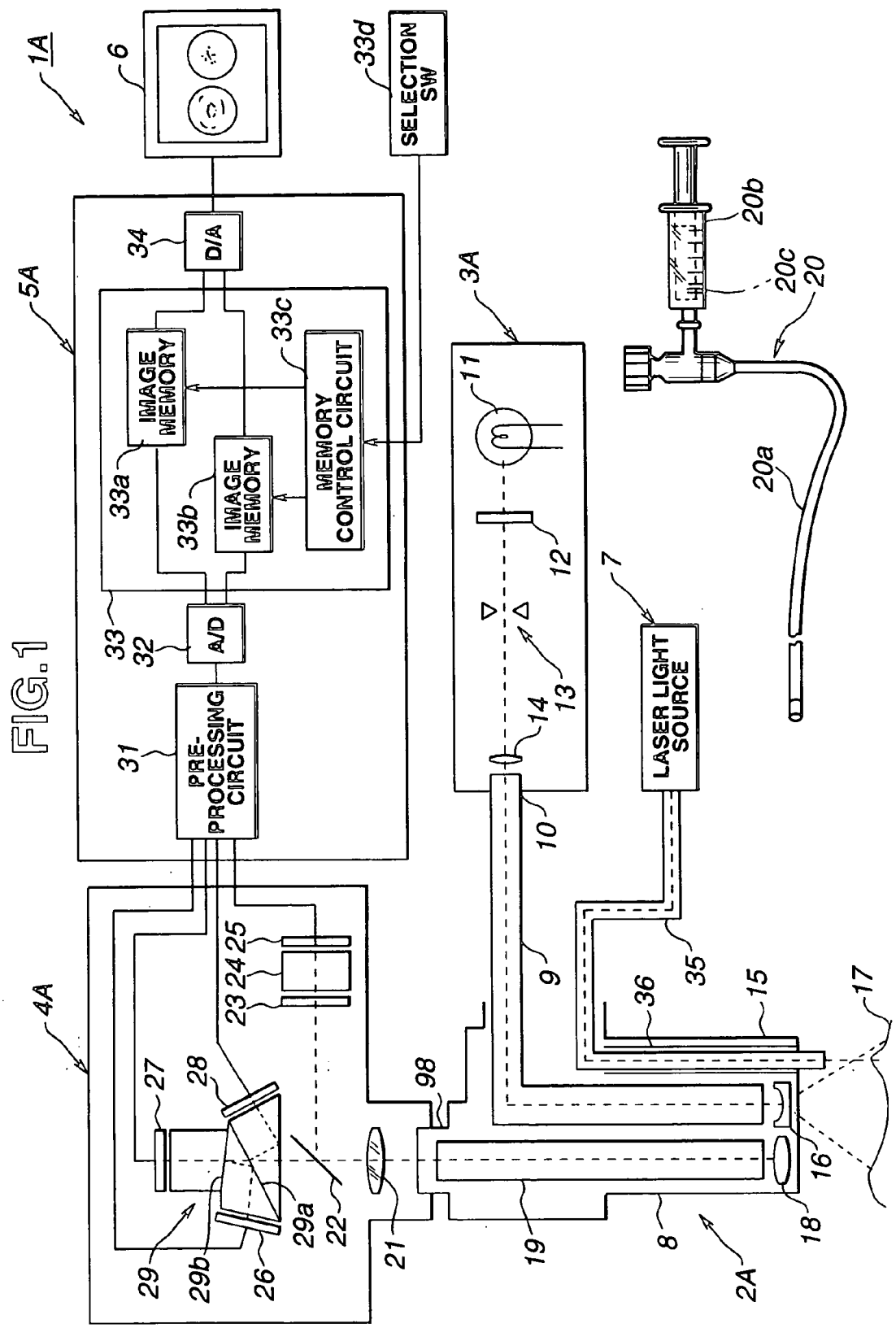

As shown in FIG. 1, a fluorescent endoscope system 1A in accordance with the first embodiment of the present invention comprises an endoscope 2A to be inserted into a body cavity for observation or diagnosis of the inside of the body cavity, a light source apparatus 3A for emitting light for observation and for excitation, a camera head 4A mounted on the endoscope 2A and having an imaging means therein, a processor 5A for processing a signal sent from the imaging means, a monitor 6 for displaying an image, a laser light source 7 for irradiating laser light for treatment, and an administration instrument 20 for use in administering a fluorescent substance into a living body through a forceps channel 36 in the endoscope 2A.

In this embodiment, an electronic endoscope having an imaging means is realized with a camera-mounted endoscope formed by mounting the freely attachable and detachable camera head 4A on an eyepiece unit 98 of the optical endoscope 2A.

The endoscope 2A has an elongated flexible insertional part 8 to be inserted into a body cavity. A light guide fiber 9 over which illumination light is propagated is run through the insertional part 8. A light guide connector 10 located at an incident end of the light guide fiber 9 to be placed near an operator's hand can be freely detachably attached to the light source apparatus 3A.

The light source apparatus 3A includes a lamp 11 for radiating light with wavelengths in a spectrum ranging from the infrared spectrum including the wavelengths of excitation light to the visible spectrum, a bandpass filter 12 located on the path of illumination light emanating from the lamp 11 for restricting the wavelengths of light to be transmitted, an illumination light diaphragm 13 for restricting an amount of light, and a condenser 14 for concentrating light.

Figure 2:
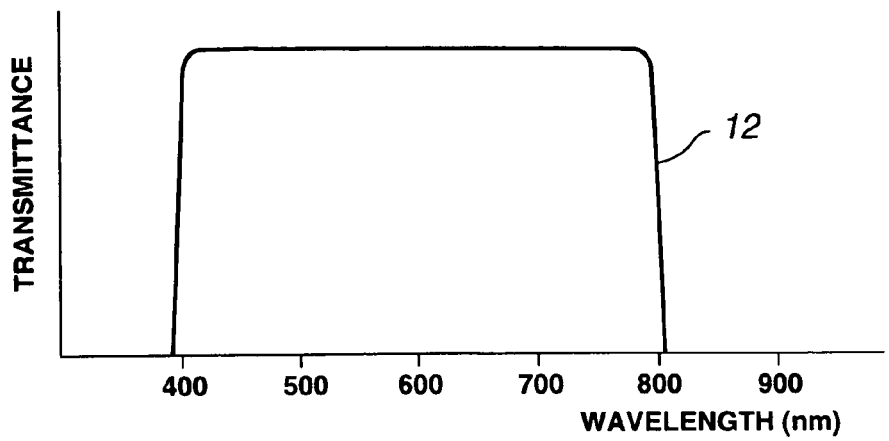

The bandpass filter 12 exhibits, as shown in FIG. 2, a nearly flat characteristic of transmission in relation to a spectrum ranging from the visible spectrum to the infrared spectrum including the wavelengths of excitation light.

Light components with wavelengths in the spectrum ranging from the visible spectrum to the infrared spectrum is extracted from light emanating from the lamp 11 by the band pass filter 12, and supplied to the light guide connector 10 of the endoscope 2A via the illumination light diaphragm 13 and the condenser 14. The light is then emitted from a distal end of the light guide fiber locked in a distal part 15 of the insertional part 8 to a living tissue 17 in a body cavity through an illumination lens 16 attached to an illumination window. Thus, the living tissue 17 is illuminated with light with wavelengths in the visible spectrum and with excitation light with wavelengths in the infrared spectrum.

The distal part 15 has an observation window adjacently to the illumination window. An objective lens 18 is attached to the observation window. Reflected light and fluorescence stemming from the illustrated living tissue 17 fall on the objective lens, whereby images are formed at an image formation position of the objective lens. Location at the image formation position is, the distal end of an image guide fiber 19 serving as a transmitting means for transmitting optical images. Optical images formed on the distal end are transmitted to a back end of the image guide fiber.

The camera head 4A has an image formation lens 21 opposed to the back end. A dichroic mirror 22 is located in the middle of an optical axis of the image formation lens 21 reaching an image formation position of the image formation lens 21.

Figure 3:
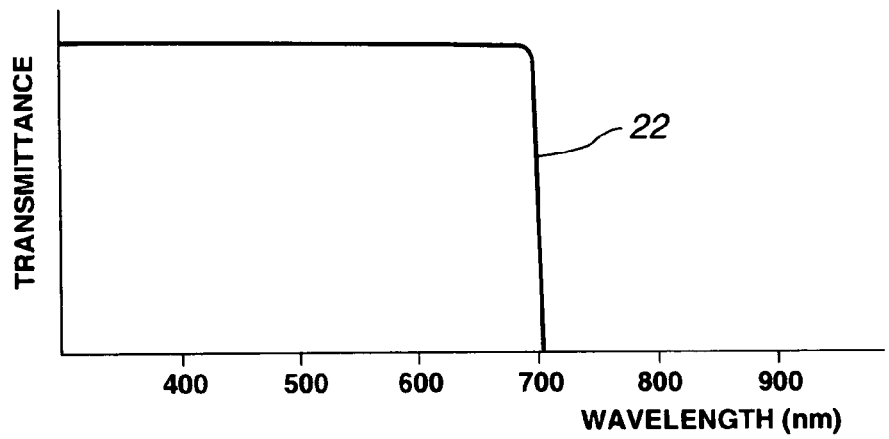

The characteristic of the dichroic mirror 22 concerning transmission is, as shown in FIG. 3, such that the dichroic mirror transmits visible-light components and reflects light components having longer wavelengths than the visible light.

Consequently, an optical image depicted by the visible-light components is formed at the image formation position toward which light transmitted by the dichroic mirror 22 is directed, and an optical image depicted by infrared-light components having longer wavelengths than visible light is formed at an image formation position toward which light reflected from the dichroic mirror 22 is directed.

An excitation light cutoff filter 23 for removing excitation-light components from separated infrared light, and a first CCD 25 are placed at the image formation position toward which light reflected from the dichroic mirror 22 is directed with an image intensifier 24 for amplifying infrared light between them. The first CCD 25 receives light amplified by the image intensifier 24, photoelectrically converts the light, and thus produces an image signal representing the infrared-light components.

Figure 4:
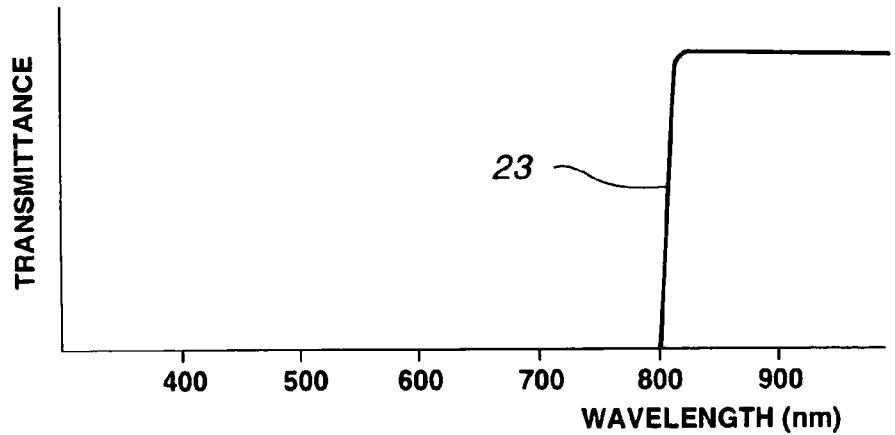

The excitation light cutoff filter 23 is, as shown in FIG. 4, characteristic of transmitting light with wavelengths longer than the wavelengths of excitation light in the infrared spectrum. The spectrum includes the wavelengths shown in FIG. 5 of fluorescence emanating from an antibody labeled by indocyanine green that is a fluorescent substance.

Excitation light is cut off by the excitation light cutoff filter 23. Fluorescence components emanating from the fluorescent substance are introduced to the CCD 25.

At the image formation position toward which light transmitted by the dichroic mirror 22 is directed, a second CCD 26 for receiving red light, a third CCD 27 for receiving green light, and a fourth CCD 28 for receiving blue light are arranged with a dichroic prism 29 for separating red light, green light, and blue light from visible light placed among the CCDs. The CCDs produce image signals representing the color light components.

The dichroic prism 29 has a blue reflection dichroic mirror layer 29a for selectively reflecting blue light located at an incident end thereof, and has a red reflection dichroic mirror layer 29b for selectively reflecting red light located at a transmission end thereof. Owing to this structure, red light, green light, and blue light fall on the second to fourth CCDs 26 to 28.

Image signals produced by the first to fourth CCDs 25 to 28 are input to the processor 5A over signal lines. The processor 5A includes a pre-processing circuit 31 for carrying out pre-processing such as amplification and white balance adjustment for the image signals produced by the first to fourth CCDs 25 to 28, an A/D conversion circuit 32, a video signal processing circuit 33 for carrying out processing such as image enhancement, and a D/A conversion circuit 34.

The video signal processing circuit 33 includes an image memory 33a for storing component images of red, green, and blue produced by the second to fourth CCDs 26 to 28, an image memory 33b for storing an infrared image produced by the first CCD 25, and a memory control circuit 33c for controlling writing or reading in or from the image memories 33a and 33b.

Also included is a display selection switch 33d for use in selecting a display format according to which a visible light image and infrared image are displayed on the monitor 6.

A video signal output from the D/A conversion circuit 34 is input to the monitor 6, whereby the fluorescence image formed on the image plane of the first CCD 25 and the visible light image formed on the image planes of the second to fourth CCDs 26 to 28 can be displayed on a display screen of the monitor 6.

In this embodiment, a laser light source 7 for generating laser light for laser therapy and a laser guide 35 for introducing the laser light are included. The laser guide 35 is structured to be able to be inserted into the forceps channel 36 of the endoscope 2A.

In this embodiment, an antibody labeled by indocyanine green that has an affinity for a lesion developing in the living tissue 17 (is characteristic of accumulating in the lesion) and that causes the living tissue 17 to transmit excitation light with wavelengths in the infrared spectrum higher than the visible and ultraviolet spectra, and to emit fluorescence with wavelengths in the infrared spectrum is used as a fluorescent substance to be administered to the living tissue 17.

Light with wavelengths including the wavelengths of the visible spectrum and the wavelengths of excitation light for exciting the fluorescent substance is irradiated from an illumination means to the living tissue 17. Light reflected from the living tissue 17 is mixed with self-fluorescence of the living tissue 17 and fluorescence induced by excitation light. Light components with wavelengths in the visible spectrum and infrared spectrum are separated from the resultant light by means of the dichroic mirror 22. Using the light components with wavelengths in the visible spectrum, the second to fourth CCDs 26 to 28 produce portions of a visible light image. The excitation light included in the light with wavelengths in the infrared spectrum is cut off by the excitation light cutoff filter 23. The first CCD 25 then produces a fluorescence image depicted by fluorescence emanating from the fluorescent substance.

Next, the operations of the fluorescent endoscope system 1A having the foregoing components will be described. An antibody labeled by indocyanine green is administered to the living tissue 17 prior to an examination using the fluorescent endoscope system 1A.

Conventional fluorescent substances are usually administered to a body by performing intravenous injection. Another method of administering the antibody labeled by indocyanine green is such that a subject is asked to gulp a solution containing the antibody labeled by indocyanine green, or the antibody labeled by indocyanine green is dispersed directly into a living tissue inside a body using the endoscope 2A.

For example, a tube 20a forming the administration instrument 20 is, as shown in FIG. 6, inserted into a forceps port of the endoscope 2A and run through the forceps channel. A movable part of a syringe 20b connected to the back end of the tube 20a is thrust, thus dispersing a fluorescent substance 20c that is the solution containing the antibody labeled by indocyanine green into the living tissue 17 through a small hole at the distal end of the tube 20a.

The antibody labeled by indocyanine green is, as described in the PCT WO96 23525, having an affinity for a lesion such as a carcinoma. When some time elapses after administration to the inside of a body, the antibody labeled by indocyanine green accumulates in the lesion. Moreover, the antibody labeled by indocyanine green is structured similarly to indocyanine green (ICG) that has been employed in an examination for studying the hepatic functions in the past. The antibody labeled by indocyanine green is therefore quite safe for a living body.

When bonded with human IgG, the antibody labeled by indocyanine green exhibits the characteristic of excitation and fluorescence shown in FIG. 5. The peak wavelength of excitation light (indicated with a dashed line) is about 770 nm, and the peak wavelength of fluorescence (indicated with a solid line) is about 810 nm. However, in practice, since the antibody labeled by indocyanine green is bonded with another substance existent inside the body, the wavelengths become a bit longer.

Light with wavelengths of about 770 to 780 nm is irradiated to the inside of a living body and light with wavelengths of about 810 to 820 nm is detected, whereby it becomes apparent whether or not a lesion is present. Light passed by the bandpass filter 12 includes light components with wavelengths in the visible spectrum and with wavelengths of about 770 to 780 nm, but does not include light components with wavelengths of about the peak wavelength of fluorescence (the bandpass filter 12 passes light components with wavelengths in the visible spectrum and wavelengths of a maximum of 800 nm). A filter characteristic of passing light with long wavelengths of 800 m or larger is, as shown in FIG. 4, adopted as the excitation light cutoff filter 23 for extracting fluorescence components.

As long as excitation light with wavelengths of about 800 nm is used, it is unnecessary to take care of the influence of self-fluorescence emanating from a living tissue itself. Moreover, since the light is little absorbed by hemoglobin or water, the light is transmitted efficiently by the living tissue. Excitation light can therefore be irradiated to a region deeper than the mucosa of a living tissue. Fluorescence stemming from the deep region may be transmitted by the surface of the living tissue.

The lamp 11 in the light source apparatus 3A is a xenon lamp and radiates light with wavelengths in a spectrum including the visible spectrum and the spectrum of wavelengths of excitation light for exciting an antibody labeled by indocyanine green. Light radiated from the lamp 11 is recomposed into light with wavelengths in a spectrum including the visible spectrum and the spectrum of wavelengths of excitation light while passing through the bandpass filter 12.

The bandpass filter 12 transmits red, green, and blue light rays and light with wavelengths of about 770 to 780 nm which excites an antibody labeled by indocyanine green, and cuts off light with wavelengths of 810 to 820 nm which is fluorescence components emanating from the antibody labeled by indocyanine green.

Light passed by the bandpass filter 12 has an amount of light thereof adjusted by the illumination light diaphragm 13, is concentrated by the condenser 14, and is then supplied to the light guide fiber 9 in the endoscope 2A.

Light propagated over the light guide fiber 9 is irradiated from the distal end of the light guide fiber to the living tissue 17 through the illumination lens 16. The optical systems in the endoscope 2A and light source apparatus 3A are designed to cope with the infrared spectrum. Irradiated light is absorbed and reflected by the living tissue 17, and fluorescence is emitted from a lesion in which an antibody labeled by indocyanine green administered in advance is accumulated.

The reflected light and fluorescence stemming from the living tissue 17 form images on the distal end of the image guide fiber 19. The images are transferred to the back end of the image guide fiber 19, and input to the camera head 4A mounted on the endoscope 2A through the image formation lens 21.

Light incident on the camera head 4A has infrared-light components and visible-light components thereof separated therefrom by the dichroic mirror 22. The infrared-light components reflected by the dichroic mirror 22 fall on the excitation light cutoff filter 23, are amplified by the image intensifier 24, and then detected by the first CCD 25.

The excitation light cutoff filter 23 is designed to remove excitation-light components for exciting an antibody labeled by indocyanine green and to transmit fluorescence components. The excitation light cutoff filter exhibits the spectroscopic characteristic of transmission shown in FIG. 4.

The image intensifier 24 is sensitive to wavelengths of about 350 nm to 910 nm, and capable of detecting fluorescence emanating from an antibody labeled by indocyanine green. Thus, the first CCD 25 produces an image depicted by fluorescence components emanating from the antibody labeled by indocyanine green.

Visible-light components transmitted by the dichroic mirror 22 are input to a three-plate camera composed of the dichroic prism 29 and three CCDs 26, 27, and 28. The dichroic prism 29 separates three light components of red, green, and blue from incident light, and routes the components into the second CCD 26, third CCD 27, and fourth CCD 28.

Thus, the second, third, and fourth CCDs 26 to 28 produce normal visible light (normal light) images. The first to fourth CCDs 25 to 28 are driven synchronously by a CCD drive circuit that is not shown. Each CCD produces 30 frame images per second.

The electric signals produced by the CCDs 25 to 28 are input to the pre-processing circuit 31 in the processor 5A. The gains of the signals are controlled by an amplifier that is not shown, and the white balances of visible light images are adjusted by a white balance correction circuit that is not shown.

Thereafter, the signals are input to the A/D conversion circuit 32 and converted into digital signals. The digital signals are input to the video signal processing circuit 33, and stored temporarily in the image memories 33a and 33b. Thereafter, the signals are subjected to image processing such as image enhancement and noise elimination, and controlled for simultaneous display of a fluorescence image, normal light image, and character information.

The video signal processing circuit 33 can carry out the processing for displaying a fluorescence image and normal light image while superposing the fluorescent image on the normal light image or the processing for normalizing a fluorescence image by carrying out inter-image computation for a normal light image and fluorescence image. Thus, an easily discernible fluorescence image can be produced together with a normal light image.

A digital signal output from the video signal processing circuit 33 is input to the D/A conversion circuit 34, converted into an analog signal, and then output to the monitor 6. As for a display format on the monitor 6, it can be selected whether a normal light image and fluorescence image giving different visions of an object attained at the same time instance are displayed side by side with the same size, the two images are displayed side by side with different sizes, the two images are displayed with one of the images superposed on the other, or images produced by performing image processing on a fluorescence image and normal light image are displayed. An operator can therefore view both a fluorescence image and normal light image simultaneously.

A fluorescence image and normal light image giving different visions of an object attained with no time difference between them can be produced. Consequently, positioning a lesion can be carried out readily with high precision. This will be found very useful for diagnosis.

Figure 7A:
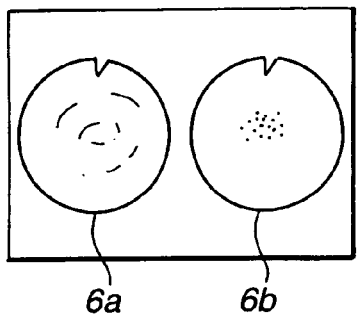
FIGS. 7A to 7E are diagrams showing particular examples of an image displayed on a monitor.
Figure 7B:
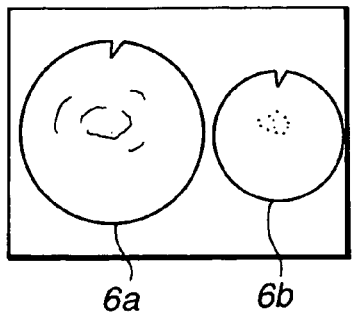
Figure 7C:
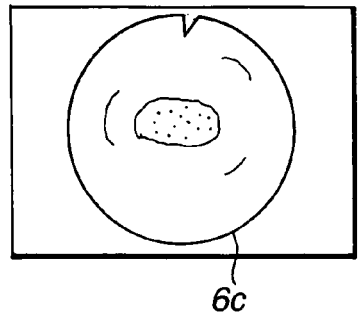
Figure 7D:
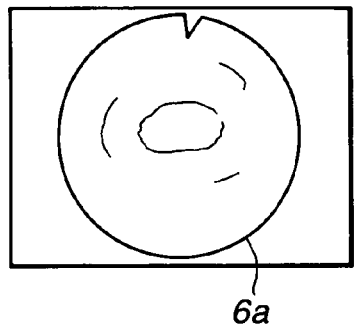
Figure 7E:
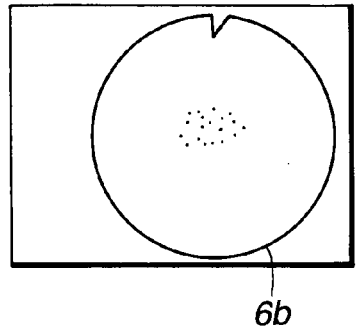

FIGS. 7A to 7E show images displayed on the monitor 6 according to display formats selected using the selection switch 33d. FIG. 7A shows a display format in which a normal light image 6a and fluorescence image 6b giving different visions of an object attained at the same time instant are displayed side by side with the same size. FIG. 7B shows a display format in which the normal light image 6a and fluorescence image 6b giving different visions of an object attained at the same time instant are displayed side by side with different sizes. FIG. 7C shows an image 6c displayed by superposing a fluorescence image on a normal light image giving one vision of an object attained at the same time instant as the other vision thereof given by the fluorescence image. FIGS. 7D and 7E show the normal light image 6a and fluorescence image 6b respectively.

For laser therapy, laser light is emitted from the laser light source 7. The emitted laser light is irradiated to a lesion in the living tissue 17 through the laser guide 35. The laser light source is a semiconductor laser. The wavelengths of laser light are matched with the wavelengths of excitation light for exciting an antibody labeled by indocyanine green. It will therefore not take place that a fluorescence image or normal light image is disturbed greatly by irradiation of laser light. Moreover, since laser light is absorbed by the antibody labeled by indocyanine green, the lesion can be treated efficiently.

In this embodiment, the three-plate camera is employed. A single-plate camera having a mosaic filter placed on the face of the CCD 26 or the like may be substituted for the three-plate camera. When the single-plate camera is used to detect normal light, cost can be reduced.

Instead of using a single lamp as a light source means for observation, two or more light sources, for example, a halogen lamp for normal light observation and a semiconductor laser or light-emitting diode for use in exciting a fluorescent substance may be used in combination.

Moreover, since illumination light for exciting a fluorescent substance is well-transmitted by the living tissue 17, the light may be irradiated in vitro.

Moreover, the camera head 4A may not be employed. A light-receiving device such as a CCD may be incorporated in the processor 5A. The endoscope 2A and processor 5A may be connected using an optical connector. In this case, the endoscope 2A becomes more lightweight and compact.

For removing excitation light, the excitation light cutoff filter 23 may not be placed in front of the image intensifier 24. Alternatively, a dichroic mirror characteristic of not reflecting an excitation-light component may be used as the dichroic mirror 22.

This embodiment has the advantages described below.

According to this embodiment, a fluorescence image depicted by light with wavelengths in the infrared spectrum emanating from an antibody labeled by indocyanine green can be viewed. When fluorescence with long wavelengths can thus be observed, since self-fluorescence with long wavelengths can be ignored almost completely, incorrect diagnosis derived from the self-fluorescence can be prevented. Moreover, since fluorescence with long wavelengths and a high transmittance can be observed, fluorescence stemming from a lesion in a deep submucosal region can be detected. Consequently, it can be prevented effectively that the lesion in the deep submucosal region is missed.

Moreover, since a separating means for separating infrared fluorescence from visible light is included, a normal visible-light image and an infrared fluorescence image which give different visions of an object attained exactly at the same time instant can be produced. Consequently, when an object moving violently is examined using an endoscope, or in particular, when a fluorescence image is superposed on a normal light image or the fluorescence image and normal light image are subjected to inter-image computation, artifacts derived from a difference in position of the object between the images will not be produced.

Moreover, when a visible light image and infrared fluorescence image which give different visions of an object attained at the same time instant are displayed with, for example, one of the images superposed on the other, if the distal portion of the endoscope 2A is moved or a treatment is carried out using a therapeutic instrument run through the forceps channel, the contour or the like of the living tissue 14 can be recognized by referencing the visible light image. By referencing the visible light image, therefore, the endoscope 2A can be oriented properly. This leads to a proper treatment. In other words, maneuverability can be improved.

Furthermore, since the four CCDs 25 to 28 are used to produce an infrared fluorescence image, red image, green image, and blue image, high-quality images can be produced. The configuration of this embodiment is especially suitable for the employment of high-definition CCDs.

Next, the second embodiment of the present invention will be described. An object of this embodiment is to provide a fluorescent endoscope system capable of producing a visible light image and an infrared fluorescence image depicted by fluorescence emanating from an antibody labeled by indocyanine green, which give different visions of an object attained with no time difference between them, and capable of being realized by adopting a relatively compact imaging system.

This embodiment is configured similarly to the first embodiment. A difference will be described mainly. The same reference numerals will be assigned to components having similar functions. The description of the components will be omitted.

A fluorescent endoscope system 1B in accordance with the second embodiment shown in FIG. 8 is different from the fluorescent endoscope system 1A in the first embodiment in a point that an electronic endoscope 2B to be inserted into a body cavity for observation or the like is substituted for the endoscope 2A and camera head 4A.

The electronic endoscope 2B has the elongated insertional part 8 similarly to the optical endoscope 2A. The light guide fiber 9 is run through the insertional part 8, and the light guide connector 10 to be situated near an operator's hand is freely detachably attached to the light source apparatus 3A. Light supplied from the light source apparatus 3A is propagated over the light guide fiber 9 and emitted from the distal end of the light guide fiber locked in the distal part 15 to the living tissue 17 through the illumination lens 16.

An image of the living tissue 17 is formed on the objective lens 18 attached to the observation window. A CCD 39 having a mosaic filter 37 placed in front of the light-receiving plane of the CCD 39 is located at the image formation position of the objective lens.

The CCD 39 is connected to the processor 5A over a signal cable 38 run through the insertional part 8. An image signal produced by the CCD 39 is input to the pre-processing circuit 31.

The mosaic filter 37 has, as shown in FIG. 9, transmission filter elements IR, R, G, and B, which separate infrared components IR, red visible-light components R, green visible-light components G, and blue visible-light components B, located in front of the pixels of the CCD 39.

Figure 10:
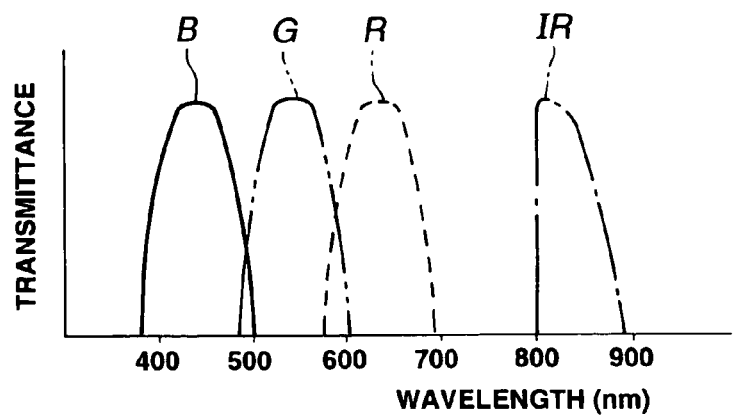

FIG. 10 shows the characteristics of the transmission filter elements concerning transmission. The transmission filter elements IR are characteristic of cutting off excitation light and passing fluorescence emanating from a fluorescent substance.

The pre-processing circuit 31 in the processor 5A extracts signal components R, G, and B passed by the transmission filter elements R, G, and B from an image signal output from the CCD 39, and thus produces color signals of red, green, and blue. Moreover, the pre-processing circuit 31 produces a fluorescence image signal by extracting signal components passed by the transmission filter elements IR.

The other components are identical to those in the first embodiment. The description of the components will be omitted.

Next, the operation of this embodiment will be described.

Light radiated from the lamp 11 in the light source apparatus 3A is supplied to the end of the light guide fiber 9, which is located near an operator's hand, in the electronic endoscope 2B by way of the bandpass filter 12 and illumination light diaphragm 13, and irradiated from the distal end of the light guide fiber 9 to the living tissue 17 through the illumination lens 16. The bandpass filter 12 exhibits the aforesaid characteristic shown in FIG. 2.

Reflected light and fluorescence stemming from the living tissue 17 fall on the objective lens 18 in the distal part 15 of the electronic endoscope 2B, and forms images on the light-receiving plane (image plane) of the CCD 39 via the mosaic filter 37 located in front of the CCD 39.

The filter elements of the mosaic filter 37 are arranged as shown in FIG. 9, whereby infrared light components (IR), and red (R), green (G), and blue (B) visible-light components are separated from light incident on the CCD 39. The filter elements of the mosaic filter 37 exhibit the spectroscopic characteristics of transmission shown in FIG. 10.

Visible-light components of red, green, and blue separated by the mosaic filter 37 form normal visible-light images. Infrared components separated by the mosaic filter 37 have wavelengths including the wavelengths of fluorescence but not including the wavelengths of excitation light. Only a fluorescence image representing the state of a fluorescent substance can therefore be produced.

A signal output from the CCD 39 is input to the preprocessing circuit 31, A/D conversion circuit 32, video signal processing circuit 33, and D/A conversion circuit in the processor 5A in that order, and then output to the monitor 6.

In this embodiment, visible-light components are divided into red components, green components, and blue components. Alternatively, they may be divided into cyan components, magenta components, and yellow components.

Instead of using a single lamp as a light source means for observation, two or more light sources, for example, a halogen lamp for normal light observation and a laser diode or light-emitting diode for use in exciting a fluorescent substance may be used in combination.

Illumination light for use in exciting a fluorescent substance may be irradiated in vitro.

This embodiment has the advantages described below.

According to this embodiment, infrared fluorescence emanating from an antibody labeled by indocyanine green can be observed. Moreover, since infrared fluorescence and visible light are separated from each other by the mosaic filter 37, a normal visible-light image and infrared fluorescence image which express the states of objects at the same time instant can be produced. Moreover, both normal light and fluorescence are observed using one imaging device. This results in a compact imaging system.

Next, the third embodiment of the present invention will be described. An object of this embodiment is to produce a visible light image and an infrared fluorescence image depicted by fluorescence emanating from an antibody labeled by indocyanine green, which express the states of objects attained with a very small time difference between them.

The third embodiment is configured similarly to the first embodiment. Only a difference will be described mainly. The same reference numerals will be assigned to components having similar functions. The description of the components will be omitted.

As shown in FIG. 11, a fluorescent endoscope system IC in accordance with the third embodiment is different from the fluorescent endoscope system 1A in the first embodiment shown in FIG. 1 in a point that a light source apparatus 3B is substituted for the light source apparatus 3A and a camera head 4B is substituted for the camera head 4A.

The light source apparatus 3B has an RGB rotary filter 41 for restricting wavelengths of light to be transmitted placed on an optical path linking the illumination light diaphragm 13 and condenser 14. The RGB rotary filter 41 is driven to rotate by means of a motor 42.

Figure 12:
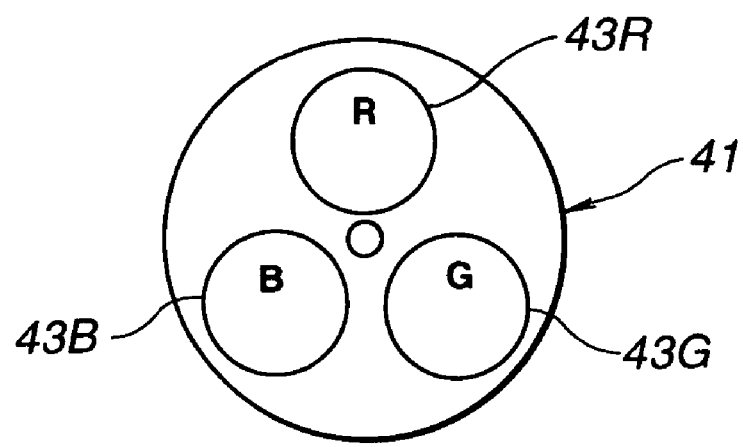

The RGB rotary filter 41 has, as shown in FIG. 12, three apertures in the circumferential direction of a light-interceptive disk. Red, green, and blue filters 43R, 43G, and 43B are fitted into the apertures. When driven by the motor 42, the RGB rotary filter rotates 30 times per second. Thus, red, green, and blue light rays are selectively transmitted.

Figure 13:
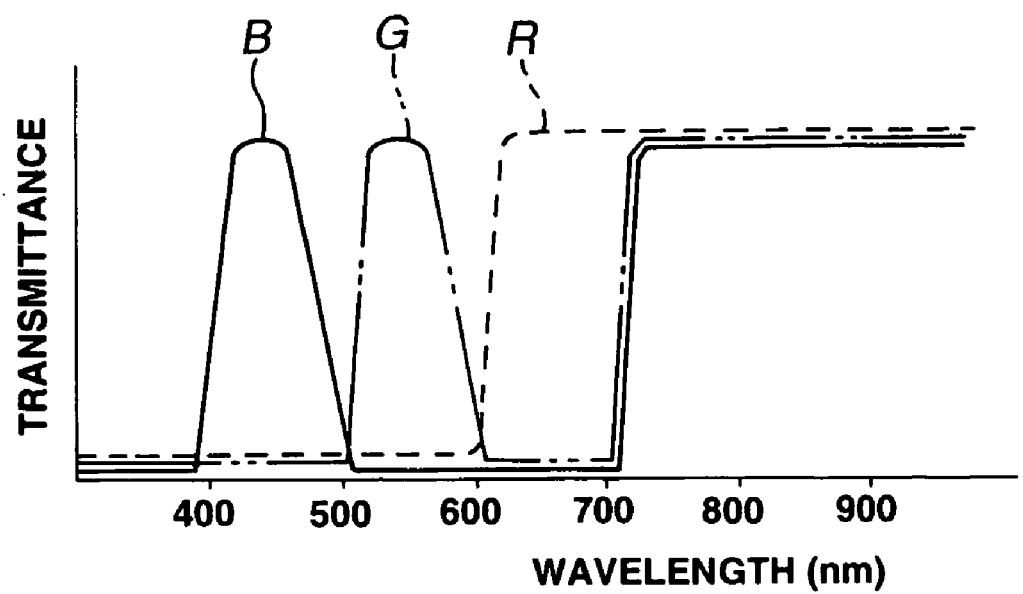

The red, green, and blue filters 43R, 43G, and 43B embedded in the RGB rotary filter 41 exhibit the spectroscopic characteristics of transmission shown in FIG. 13. Thus, the RGB rotary filter transmits any of red, green, and blue light rays and also transmits infrared light containing excitation light components for exciting an antibody labeled by indocyanine green.

Moreover, the bandpass filter 12 exhibits the characteristic shown in FIG. 2. When the bandpass filter 12 and RGB rotary filter 41 are used in combination, one of red visible-light components, green visible-light components, and blue visible-light components and infrared light with wavelengths including the wavelengths of excitation light components but not including the wavelengths of fluorescence can be transmitted simultaneously.

The camera head 4B is identical to the camera head 4A in FIG. 1 except that the second CCD 26 alone is placed to handle light transmitted by the dichroic mirror 22. Reflected light is handled by the same components as those in FIG. 1.

Output signals produced by the two CCDs 25 and 26 are input to the processor 5A. The other components are identical to those in FIG. 1.

Next, the operation of this embodiment will be described.

Light radiated from the lamp 11 in the light source apparatus 3B is supplied to the light guide connector 10 in the endoscope 2A by way of the bandpass filter 12, illumination light diaphragm 13, RGB rotary filter 41, and condenser 14, and irradiated to the living tissue 17 by way of the light guide fiber 9 and illumination lens 16.

The RGB rotary filter 41 has, as shown in FIG. 12, the red, green, and blue filters 43R, 43G, and 43B arranged therein, and transmits red, green, and blue light rays when driven to rotate 30 times per second by means of the motor 42. The red, green, and blue filters 43R, 43G, and 43B embedded in the RGB rotary filter 41 exhibit the spectroscopic characteristics of transmission shown in FIG. 13. Any of red, green, and blur light rays is transmitted, and infrared light containing excitation light components for exciting an antibody labeled by indocyanine green is transmitted at the same time.

Moreover, the bandpass filter 12 has the characteristic shown in FIG. 2. When the bandpass filter 12 and RGB rotary filter 41 are used in combination, one of red, green, and blue visible-light components and infrared light with wavelengths including the wavelengths of excitation light but not including the wavelengths of fluorescence are transmitted simultaneously.

Reflected light and fluorescence stemming from the living tissue 17 are input to the camera head 4B mounted on the eyepiece unit of the endoscope 2A through the image guide fiber 19. Light incident on the camera head 4B has infrared light components and visible light components thereof separated therefrom by means of the dichroic mirror 22 having the characteristic shown in FIG. 3.

The infrared light components reflected by the dichroic mirror 22 are amplified by the image intensifier 24 after passed by the excitation light cutoff filter 23 having the characteristic shown in FIG. 4, and then detected by the first CCD 25.

The first CCD 25 is driven synchronously with the rotation of the RGB rotary filter by means of a CCD drive circuit that is not shown. A fluorescence image depicted by fluorescence emanating from an antibody labeled by indocyanine green is produced at the rate of 30 frames per second.

Visible light components transmitted by the dichroic mirror 22 are input to the second CCD 26. The second CCD 26 is driven synchronously with the rotation of the RGB rotary filter by means of the CCD drive circuit that is not shown. Red, green, and blue images are produced successively at the rate of 90 frames per second. A signal output from the second CCD 26 is processed by the processor 5A, whereby the signal components representing the red, green, and blue images are timed. Consequently, a normal visible image is produced.

Signals produced by the two CCDs 25 and 26 are sent to the pre-processing circuit 31, A/D conversion circuit 32, video signal processing circuit 33, and D/A conversion circuit 34 in the processor 5A, and then output to the monitor 6.

In this embodiment, a single lamp is used as a light source means for observation. Alternatively, two or more light sources, for example, a halogen lamp for normal light observation and a laser diode or light-emitting diode for use in exciting a fluorescent substance may be used in combination.

Moreover, illumination light for use in exciting a fluorescent substance may be irradiated in vitro.

Moreover, the camera head 4B may not be employed. The light-receiving devices of the CCDs 25 and 26 may be incorporated in the processor 5A, and the endoscope 2A and processor 5A may be connected using an optical connector. The endoscope 2A may thus be designed to be lightweight and compact.

For removing excitation light, instead of placing the excitation light cutoff filter 23 on the face of the image intensifier 24, a dichroic mirror characteristic of not reflecting excitation light may be used as the dichroic mirror 22.

Moreover, field-by-field processing may be substituted for frame-by-frame processing.

This embodiment has the advantages described below.

According to the embodiment, infrared fluorescence emanating from an antibody labeled by indocyanine green can be observed. Moreover, since a separating means for separating infrared fluorescence and visible light is included, an infrared fluorescence image expressing the state of an object attained at nearly the same time instant as the state of an object depicted by normal visible light can be produced.

Next, the fourth embodiment of the present invention will be described. An object of this embodiment is to provide a fluorescent endoscope system capable of producing a visible light image and an infrared fluorescence image depicted by fluorescence emanating from an antibody labeled by indocyanine green, and capable of being realized using a compact imaging system.

The fourth embodiment is configured similarly to the first embodiment. A difference will be described mainly. The same reference numerals will be assigned to components having similar functions. The description of the components will be omitted.

Figure 14:
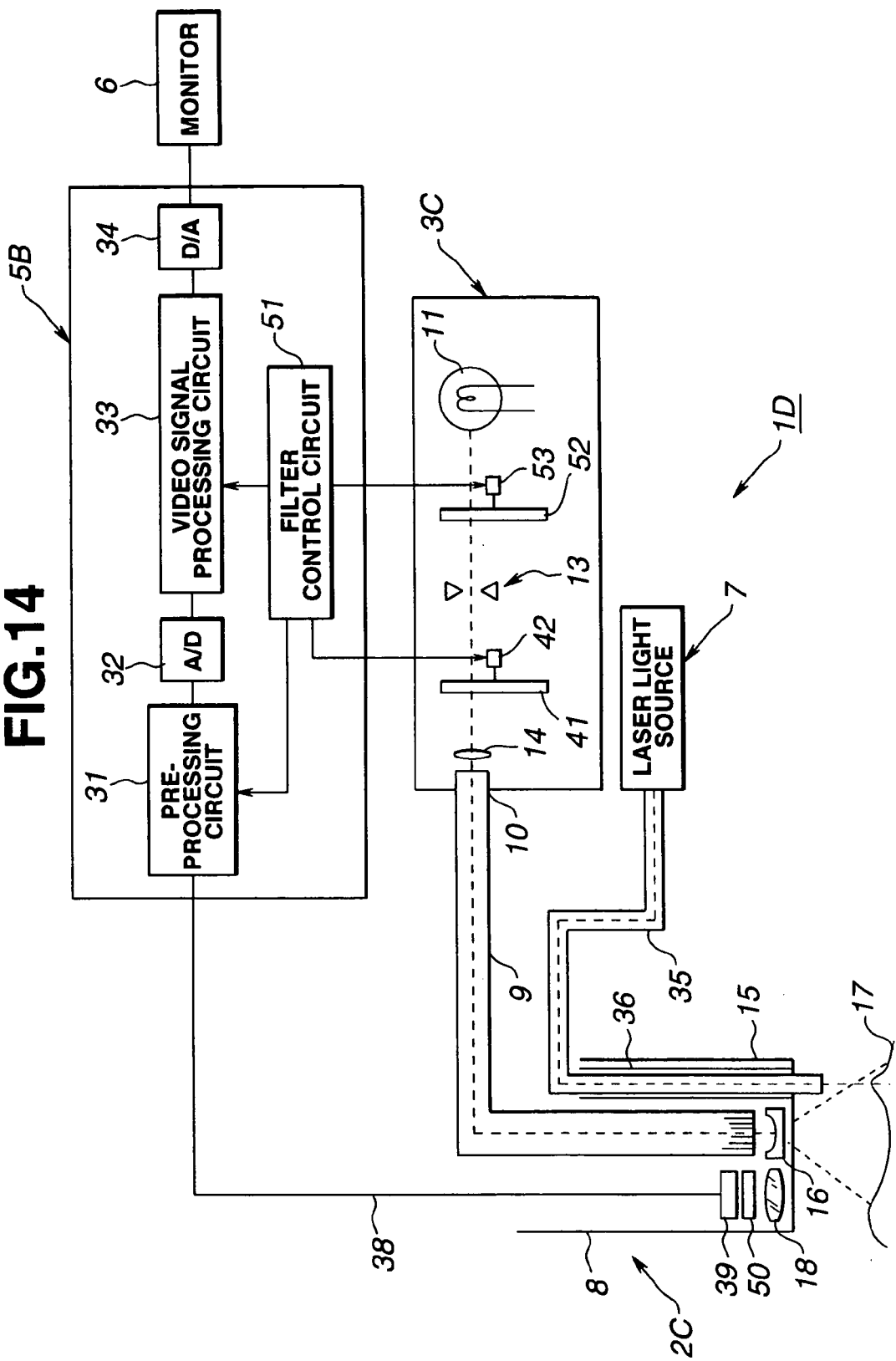

A fluorescent endoscope system 1D in accordance with the fourth embodiment shown in FIG. 14 is different from the fluorescent endoscope system 1B shown in FIG. 8 in points that an electronic endoscope 2C adopts an excitation light cutoff filter 50 instead of the mosaic filter 37 included in the electronic endoscope 2B, a processor 5B includes a filter control circuit 51 in addition to the components of the processor 5A, and a light source apparatus 3C has an RGB rotary filter 41 to be driven to rotate by a motor 42 placed on an optical path linking the illumination light diaphragm 13 and condenser 14 included in the light source apparatus 3A, and includes a spectrum restriction rotary filter 52 to be driven to rotate by a motor 53 in place of the bandpass filter 12.

Figure 15:
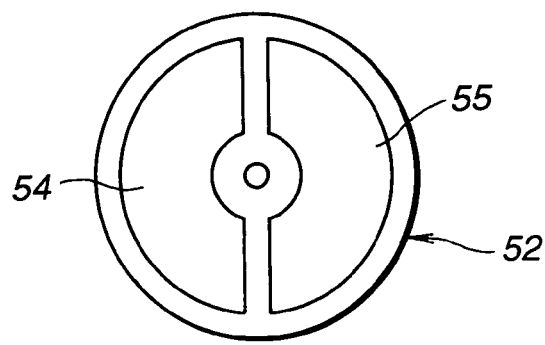

The spectrum restriction rotary filter 52 has, as shown in FIG. 15, a semicircular visible-light transmission filter 54 and infrared-light transmission filter 55 placed as halves of a circle.

Figure 16:
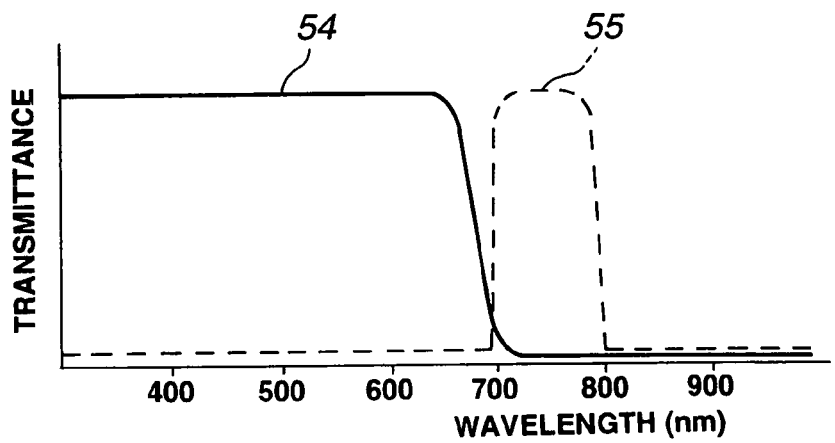

The visible-light transmission filter 54 and infrared-light transmission filter 55 exhibit the spectroscopic transmittances shown in FIG. 16, and transmit normal observation visible light and excitation infrared light respectively.

Figure 17:
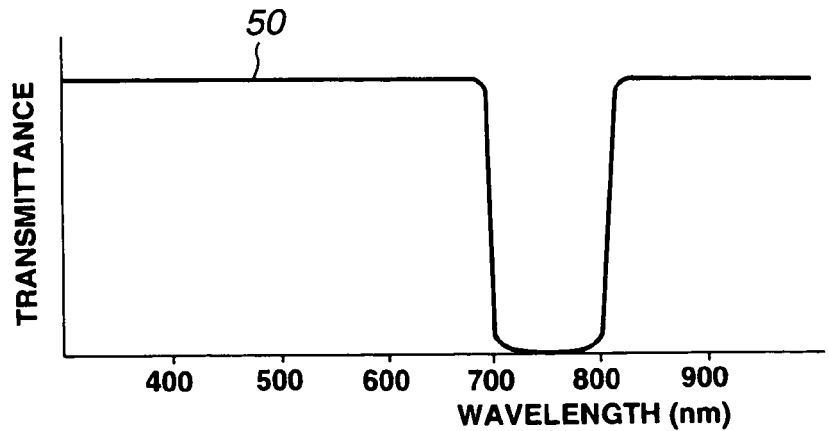

Moreover, the excitation light cutoff filter 50 exhibits the spectroscopic characteristic of transmission shown in FIG. 17, and transmits visible light components and fluorescence components with wavelengths in the infrared spectrum and cuts off excitation light components with wavelengths in the infrared spectrum.

The light source apparatus 3C has, similarly to the one described in conjunction with FIG. 12, the RGB rotary filter 41. The RGB rotary filter 41 is driven to rotate by the motor 42. Moreover, the spectrum restriction filter 52 for restricting the wavelengths of transmitted light is placed on the optical path linking the lamp 11 and illumination light diaphragm 13, and driven by the motor 53.

Rotations of the motors 42 and 53 are controlled by a filter control circuit 51. For example, when an operator presses an observation mode selection switch, which is not shown, to designate a normal observation mode, the filter control circuit 51 gives control so that the motor 53 is rotated (and stopped) by a given magnitude (given angle) in order to keep the visible-light transmission filter 54 lying on the optical path. Moreover, the rotating speed of the motor 42 is controlled so that the RGB rotary filter 41 can be rotated 30 times per second.

Moreover, when an operator presses the observation mode selection switch to designate a fluorescence observation mode, the filter control circuit 51 gives control so that the motor 53 is rotated (and stopped) by a given magnitude (given angle) in order to keep the infrared-light transmission filter 55 lying on the optical path. Moreover, the rotating speed of the motor 42 is controlled so that the RGB rotary filter 41 can be rotated 30 times per second.

Furthermore, when an operator presses the observation mode selection switch to designate a fluorescence/normal light simultaneous observation mode, the filter control circuit 51 controls the rotating speed of the motor 53 so that the spectrum restriction rotary filter 52 can be rotated 90 times per second, and controls the rotating speed of the motor 42 so that the RGB rotary filter 41 can be rotated 30 times per second synchronously with the rotation of the spectrum restriction rotary filter.

The other components are identical to those in the fluorescent endoscope system 1B shown in FIG. 8.

Next, the operation of this embodiment will be described.

Light radiated from the lamp 11 in the light source apparatus 3C is supplied to the light guide connector 10 in the electronic endoscope 2C after passed by the spectrum restriction rotary filter 52, illumination light diaphragm 13, RGB rotary filter 41, and condenser 14, propagated over the light guide filter 9, and then irradiated to the living tissue 17.

The visible-light transmission filter 54 and infrared-light transmission filter 55 of the spectrum restriction rotary filter 52 exhibit the spectroscopic transmittances shown in FIG. 16, and transmit visible light for normal observation and infrared light for excitation respectively.

The RGB rotary filter 41 has, as shown in FIG. 12, red, green, and blue filters 43R, 43G, and 43B arranged therein.

The filters 43R, 43G, and 43B exhibit the spectroscopic characteristics of transmission shown in FIG. 13. Any of red, green, and blue light rays is transmitted, and infrared light with wavelengths including the wavelengths of excitation light for exciting an antibody labeled by indocyanine green is transmitted at the same time.

In normal light observation, the visible-light transmission filter 54 of the spectrum restriction rotary filter 52 is locked on the optical path. As shown in the explanatory diagram of FIG. 18 concerning operations for normal observation, the spectrum restriction rotary filter 52 transmits visible light. At this time, the RGB rotary filter 41 is rotated 30 times per second in order to transmit red, green, and blue light rays. These light rays are irradiated successively to the living tissue 17.

Light having the wavelengths of the red, green, and blue light rays is received on the light-receiving plane of the CCD 39, and photoelectrically converted. The CCD 39 then outputs a signal representing an image formed with red, green, and blue color components. The signal is processed by the processor 5B. A normal endoscopic image depicted by visible light is displayed on the monitor 6.

In fluorescence observation, the infrared-light transmission filter 55 of the spectrum restriction rotary filter 52 is locked on the optical path. As shown in the explanatory diagram of FIG. 19 concerning operations for fluorescence observation, the spectrum restriction rotary filter 52 transmits infrared light.

At this time, the RGB rotary filter 41 is rotated 30 times per second in order to transmit infrared light having the wavelengths of excitation light. The infrared light having the wavelengths of excitation light is irradiated to the living tissue 17.

The excitation light cutoff filter 50 exhibiting the spectroscopic characteristic of transmission shown in FIG. 17, that is, capable of transmitting visible light components and fluorescence components with wavelengths in the infrared spectrum and cutting off excitation light components with wavelengths in the infrared spectrum is located in front of the light-receiving plane of the CCD 39.

Owing to the excitation light cutoff filter 50, excitation light is cut off. Fluorescence emanating from a fluorescent substance (antibody labeled by indocyanine green) is received and photoelectrically converted, whereby a signal representing a fluorescence image is output.

The fluorescence image is displayed on the monitor 6.

Moreover, for observing a fluorescence image and normal light image simultaneously, the spectrum restriction rotary filter 52 is rotated 90 times per second. As shown in the explanatory diagram of FIG. 20 concerning operations for fluorescence/normal light simultaneous observation, the spectrum restriction rotary filter 52 transmits visible light and infrared light. The rotary filter 41 is rotated 30 times per second in order to successively transmit red light, excitation light, green light, excitation light, blue light, and excitation light. These light rays are irradiated to the living tissue 17.

Thus, the filter control circuit 51 gives control so that the RGB rotary filter 41 and spectrum restriction rotary filter 52 are rotated mutually synchronously.

Reflected light and fluorescence stemming from the living tissue 17 are passed by the excitation light cutoff filter 50 and detected by the CCD 39. The CCD 39 receives visible light of red, green, and blue or infrared fluorescence according to the positions of the RGB rotary filter 42 and spectrum restriction rotary filter 52.

The CCD 39 is driven synchronously with the rotations of the filters 41 and 52 by means of a CCD drive circuit that is not shown, and outputs an image signal representing 180 frames per second responsively to the rotation of the spectrum restriction rotary filter 52.

The output signal of the CCD 39 is processed by the processor 5B, whereby a fluorescence image and normal light image are displayed on the monitor 6.

As mentioned above, in this embodiment, a signal produced by the CCD 39 is sent to the pre-processing circuit 31, A/D conversion circuit 32, video signal processing circuit 33, and D/A conversion circuit 34d in the processor 5B, and then output to the monitor 6. The pre-processing circuit 31 and video signal processing circuit 33 carry out processing associated with normal light observation, fluorescence observation, or normal light/fluorescence simultaneous observation according to a signal sent from the filter control circuit 51.

According to this embodiment, infrared fluorescence emanating from an antibody labeled by indocyanine green can be observed. Moreover, since one imaging device is used to observe both normal light and fluorescence, the imaging system becomes compact.

In this embodiment, a single lamp is used as a light source means for observation. Alternatively, two or more light sources, for example, a halogen lamp for normal light observation and a laser diode or light-emitting diode for use in exciting a fluorescent substance may be used in combination.

Moreover, illumination light for use in exciting a fluorescent substance may be irradiated in vitro.

Next, the fifth embodiment of the present invention will be described. An object of this embodiment is to make it possible to view both a fluorescence image and normal light image simultaneously and to recognize the intensity of fluorescence more accurately.

In a fluorescent method of diagnosis in which a fluorescent substance is administered to a body for endoscopic diagnosis, fluorescence of what brightness level is being emitted must be recognized quickly and accurately. However, using a conventional configuration, it is hard to accurately grasp the positional relationship between a fluorescence image and normal light image or the intensity of fluorescence.

For example, when a fluorescence image alone is viewed, even if the image has a bright area, it is hard to judge whether the area is bright because a large amount of light is emanating from a lamp, the area is bright because an object is located nearby, the area is bright because the amplification factor of a video signal is high, or the area is bright because a fluorescent substance is accumulated.

Moreover, it has been impossible in the past that a normal light image and fluorescence image are synthesized and displayed with information of the intensity of fluorescence held intact.

An example of a configuration for solving the above problem will be described below.

Figure 21:
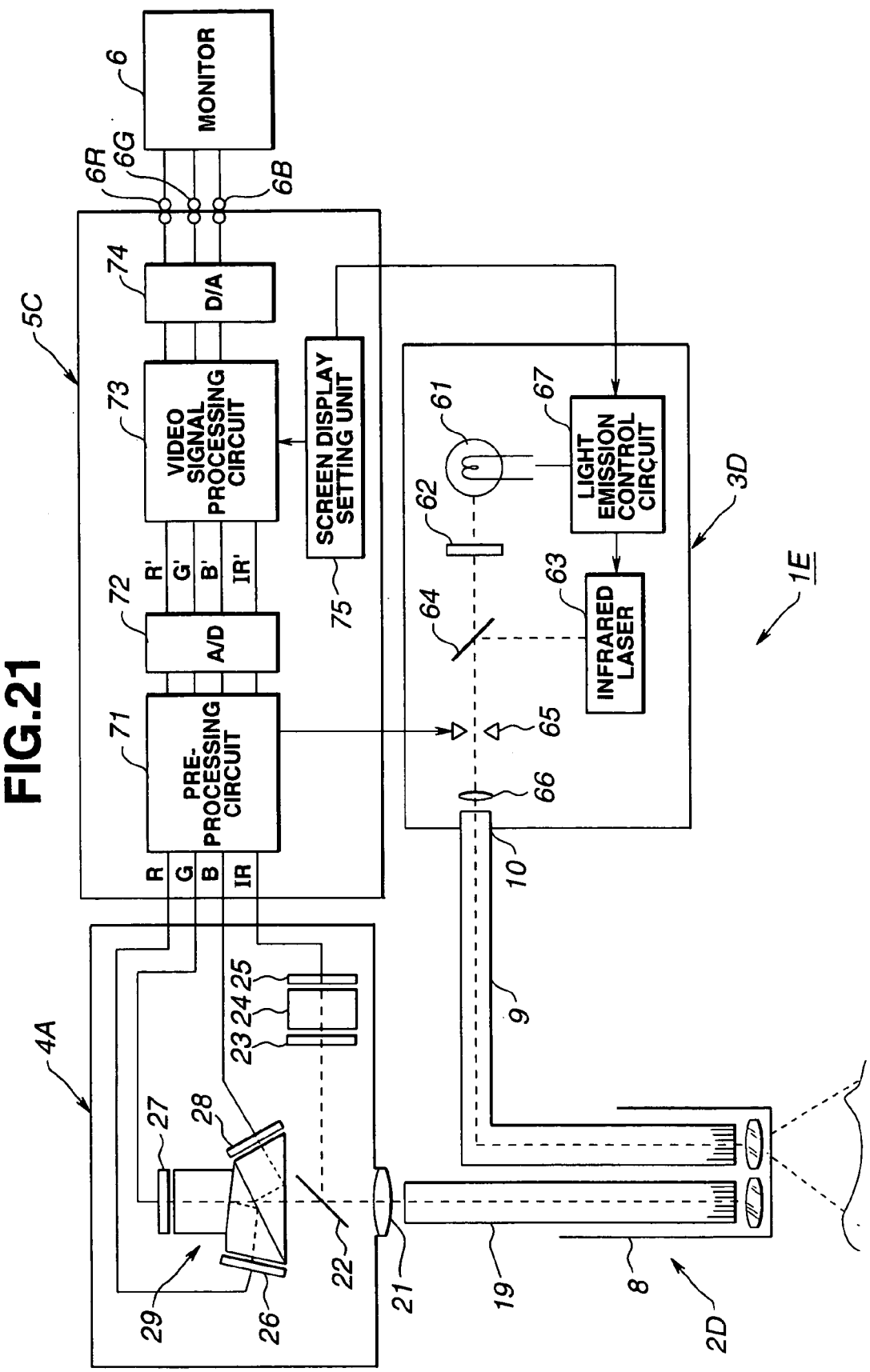
FIGS. 21 to 25 relate to the fifth embodiment of the present invention.

As shown in FIG. 21, a fluorescent endoscope system 1E in accordance with the fifth embodiment comprises an endoscope 2D to be inserted into a body cavity for observing or diagnosing the inside of the body cavity, a light source apparatus 3D for emitting light for observation or for excitation, a camera head 4A mounted on the endoscope 2D and having an imaging device therein, a processor 5C for processing a signal produced by the imaging means, and a monitor 6 for displaying images.

In this embodiment, an electronic endoscope having an imaging means is realized with a camera-mounted endoscope constructed by mounting the freely detachable camera head 4A on the eyepiece unit of the optical endoscope 2D.

The endoscope 2D has the elongated flexible insertional part 8 to be inserted into a body cavity. The light guide fiber 9 over which illumination light is propagated and the image guide fiber 19 over which light stemming from a living tissue is propagated are run through the insertional part 8. A light guide connector 10 located at an incident end of the light guide fiber 9 placed near an operator's hand is freely detachably attached to the light source apparatus 3D. The camera head 4A is freely detachably attached to the back end of the image guide fiber 19.

The light source apparatus 3D includes a lamp 61 for radiating light containing visible light, an infrared light cutoff filter 61 located on the path of illumination light radiated from the lamp 62 for restricting the wavelengths of transmitted light, an infrared laser 63 for radiating laser light with wavelengths in the infrared spectrum, a mirror 64 for transmitting light with wavelengths in the visible spectrum and reflecting light with wavelengths in the infrared spectrum, an illumination light diaphragm 65 for restricting an amount of light, a condenser for concentrating light, and a light emission control circuit 67 for controlling amounts of light emitted form the lamp 61 and infrared laser 63.

The camera head 4A includes the image formation lens 21, the dichroic mirror 22 for separating infrared light components and visible light components, the excitation light cutoff filter 23 for removing excitation light components from the separated infrared light, the image intensifier 24 for amplifying infrared light, the first CCD 25 for receiving light amplified by the image intensifier 24, the dichroic prism 29 for separating red, green, and blue light rays from visible light components, the second CCD 26 for receiving red light, the third CCD 29 for receiving green light, and the fourth CCD 27 for receiving blue light.

The processor 5C includes a pre-processing circuit 71 for amplifying image signals produced by the first to fourth CCDs 25 to 28, and carrying out pre-processing such as color balance adjustment, an A/D conversion circuit 72, a video signal processing circuit 73 for carrying out processing such as marker production and image synthesis, an D/A conversion circuit 74, and a screen display setting unit 75 for setting an image display mode.

Figure 22:
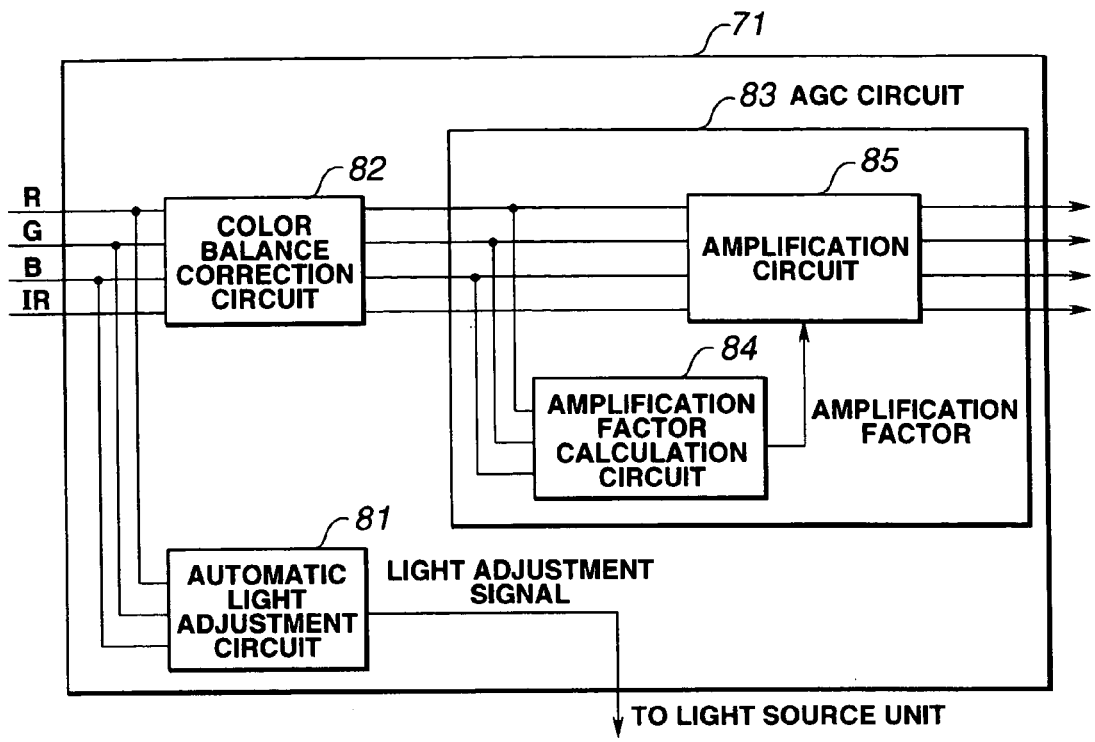

The pre-processing circuit 71 includes, as shown in FIG. 22, an automatic light adjustment circuit 81 for producing a light adjustment signal, a color balance correction circuit 82 for adjusting a color balance, and an automatic gain control (AGC) circuit 83 for automatically controlling a gain.

Figure 23:
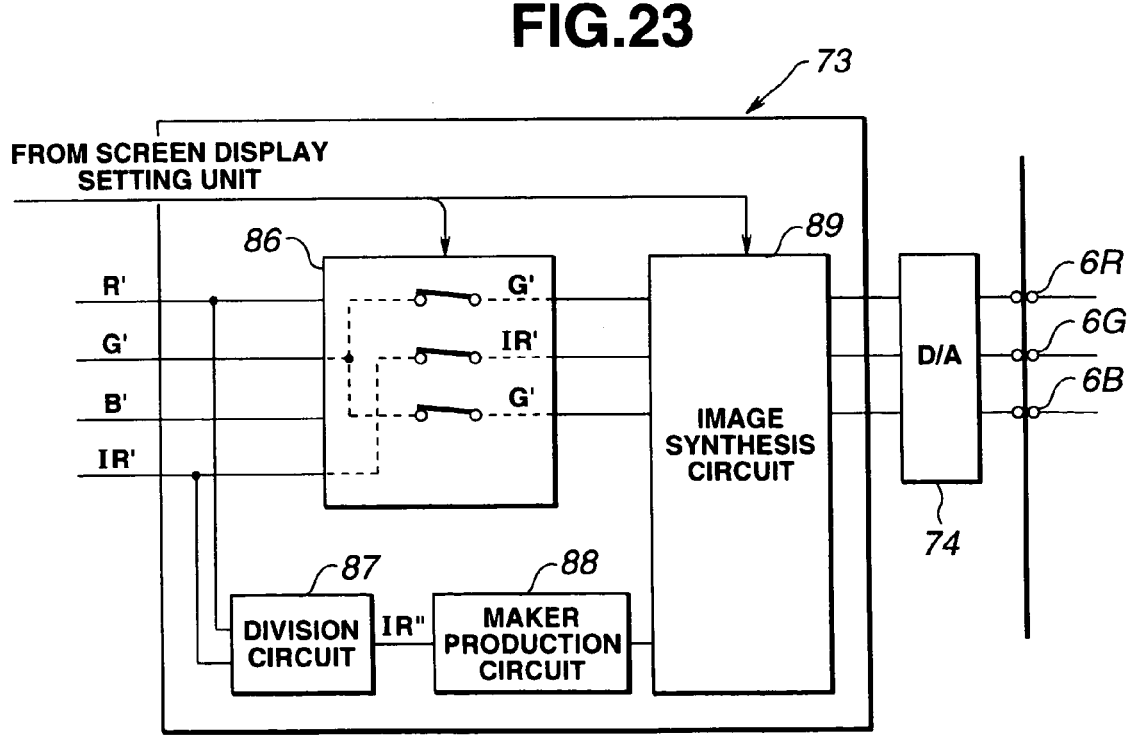

The video signal processing circuit 73 includes, as shown in FIG. 23, a multiplexer 86 for selecting any of color signals, a division circuit 87 for carrying out division for infrared light components (IR) and red light components (R), a marker production circuit 88 for producing markers on the basis of an output of the division circuit 87, and an image synthesis circuit 89 for synthesizing an output of the multiplexer 86 with an output of the marker production circuit 88.

Next, the operations of the fluorescent endoscope system 1E having the foregoing components will be described.

Similarly to the first embodiment, a fluorescent substance that is an antibody labeled by indocyanine green is administered to a living tissue in advance and accumulated in a lesion. Light with wavelengths of 770 to 780 nm is irradiated as excitation light to the inside of a body using the light source apparatus 3D. Light with wavelengths of 810 to 820 nm is detected as fluorescence. Thus, presence or absence of a lesion can be recognized.

The lamp 61 in the light source apparatus 3D is a xenon lamp and radiates light with wavelengths including the wavelengths in the visible spectrum. Light radiated from the lamp 61 is passed by the infrared light cutoff filter 62 and falls on the mirror 64. The infrared light cutoff filter 62 is a filter for transmitting red, green, and blue visible light rays and removing light with wavelengths in the infrared spectrum. Light with wavelengths in the visible spectrum passed by the infrared light cutoff filter 62 is transmitted by the mirror 64. An amount of the light is then adjusted by the illumination light diaphragm 65.

The infrared laser 63 is a semiconductor laser and radiates laser light with wavelengths of about 780 nm which excites an antibody labeled by indocyanine green. Laser light radiated from the infrared laser 63 is diffused by an optical system that is not shown, and then reflected from the mirror 64. The amount of the laser light is then adjusted by the illumination light diaphragm 65.

The illumination light diaphragm 65 has the ability to adjust both an amount of light radiated from the lamp 61 and an amount of light radiated from the infrared laser 63. At this time, the amounts of light radiated from the lamp 61 and infrared laser 63 are controlled by the light emission control circuit 67. Light passed by the illumination light diaphragm 65 is concentrated on the light guide fiber 9 in the endoscope 2D by means of the condenser 66, and irradiated to a living tissue from the distal endoscope part through the light guide fiber 9.

Light radiated from the light source apparatus 3D is absorbed or reflected by the living tissue. Fluorescence is emitted from an antibody labeled by indocyanine green administered in advance and accumulated in a lesion because the antibody is excited by irradiated excitation light.

With reflected light and fluorescence stemming from the living tissue, images are formed on the distal end of the image guide fiber 19, transmitted to the back end of the image guide fiber 19, and then input to the camera head 4A mounted on the endoscope 2D via the image formation lens 21.

Light input to the camera head 4A has infrared light components and visible light components separated therefrom by means of the dichroic mirror 22. The dichroic mirror 22 exhibits the spectroscopic characteristic of transmission shown in FIG. 3. The visible light components are transmitted and the other light components are reflected.

The infrared light components reflected by the dichroic mirror 22 are passed by the excitation light cutoff filter 23, amplified by the image intensifier 24, and then detected by the first CCD 25. The excitation light cutoff filter 23 exhibits the spectroscopic characteristic of transmission shown in FIG. 4. Excitation light components emanating from an antibody labeled by indocyanine green are removed and fluorescence components are transmitted.

The image intensifier 24 is sensitive to the wavelengths of about 350 nm to 910 nm and capable of detecting fluorescence emanating from an antibody labeled by indocyanine green. Thus, the first CCD 25 detects fluorescence components emanating from the antibody labeled by indocyanine green.

The visible light components passed by the dichroic mirror 22 are input to a three-plate camera composed of the dichroic prism 29 and the three CCDs 26, 27, and 28. The dichroic prism 29 separates red, green, and blue light components from incident light, and routes the light components to the second CCD 26, third CCD 27, and fourth CCD 28. Thus, the second to fourth CCDs 26 to 28 detect normal visible light components (normal light images).

The first to fourth CCDs 25 to 28 are driven mutually synchronously by a CCD drive circuit that is not shown. Each of the CCDs produce 30 frame images per second.

The infrared, red, green, and blue light signals (IR, R, G, and B) output from the CCDs 25 to 28 are input to the pre-processing circuit 71 in the processor 5C. The signals sent from the CCDs to the pre-processing circuit 71 are amplified by a preamplifier that is not shown, and input to the automatic light adjustment circuit 81 shown in FIG. 22. A control signal (light adjustment signal) for use in controlling the illumination light diaphragm 65 in the light source apparatus 3D is then produced.

The automatic light adjustment circuit 81 uses signals output from the second to fourth CCDs 26 to 28 designed for normal light observation to produce a light adjustment signal for use in specifying a given amount of illumination light on the basis of an amount of reflected light of light with wavelengths in the visible spectrum stemming from a living tissue. The light adjustment signal output from the automatic light adjustment circuit 81 is input to the illumination light diaphragm 65 in the light source apparatus 3D. Based on the light adjustment signal, an amount of light passed by the illumination light diaphragm 65 is controlled. Owing to this configuration, an amount of light emitted from the infrared laser 63 for exciting a fluorescent substance and irradiated to a living tissue is controlled properly on the basis of the brightness of a normal light image. It will therefore not take place that the brightness of a fluorescence image is judged incorrectly because an amount of light for exciting a fluorescent substance is too large or small.

Moreover, signals output from the CCDs and input to the preprocessing circuit 71 are also input to the color balance correction circuit 82. The color balance correction circuit 82 adjusts color balance indicated by the signals in relation to the levels of signals produced by imaging a color balance adjuster, which is not shown, serving as a color reference.

The color balance adjuster exhibits a nearly constant reflectance relative to light with wavelengths in the visible spectrum. A substance that emits, like an antibody labeled by indocyanine green, fluorescence with wavelengths of about 810 to 820 nm when excited by excitation light with wavelengths of about 770 to 780 nm is applied to the color balance adjuster. When the color balance adjuster is used to adjust color balance, the color balance of red, green, blue as well as infrared is adjusted by the color balance correction circuit 82. Consequently, a tone defect resulting from a difference in performance of a lamp in a light source apparatus or an infrared laser, a difference in spectroscopic transmittance of a light guide fiber or image guide fiber in an endoscope, or a difference in sensitivity of a CCD can be corrected.

Signals output from the CCDs and passed by the color balance correction circuit 82 are input to the AGC circuit 83 that controls the gains of the signals. The signals output from the second to fourth CCDs 26 to 28 designed for normal light observation are input to an amplification factor calculation circuit 84 in the AGC circuit 83. An amplification factor in the amplification circuit 85 is determined on the basis of an amount of reflected light of normal light with wavelengths in the visible spectrum stemming from a living tissue. The determined amplification factor is sent to the amplification circuit 85. The signals output from the CCDs and input to the AGC circuit 83 are amplified according to the amplification factor.

Owing to the above configuration, a signal representing a fluorescence image is amplified properly on the basis of the brightness of a normal light image. It will therefore not take place that the brightness of a fluorescence image is judged incorrectly because the amplification factor of the signal representing the fluorescence image is too high or low.

Signals output from the AGC circuit 83 in the pre-processing circuit 71 are input to the A/D conversion circuit 72, and converted into digital signals (IR', R', G', and B'). Thereafter, the signals are sent to the video signal processing circuit 73, and input to the multiplexer 86 shown in FIG. 23.

According to a setting signal output from the screen display setting unit 75, the multiplexer 86 selects any of input terminals 6R, 6G, and 6B of the monitor 6 to which any of the signals (IR', R', G', and B') sent from the CCDs 25 to 28 is allocated.

Figure 24:
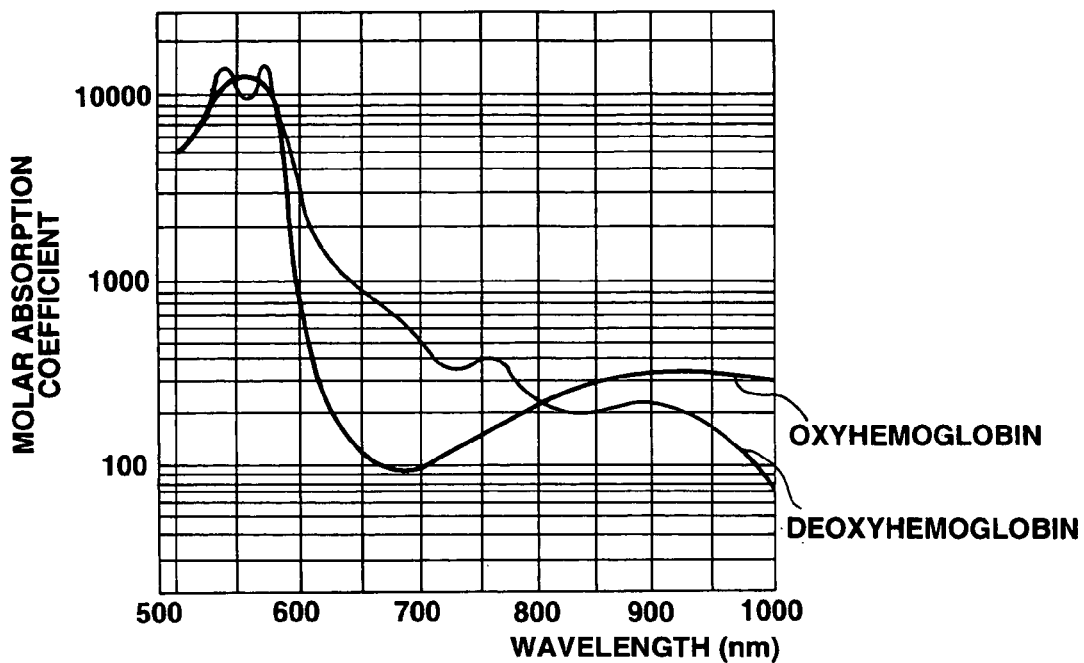

Among the signals input to the video signal processing circuit 73, the signals R' and IR' are input to the division circuit 87. A quotient IR" of the signal level IR' by the signal level R' is calculated for each pixel in an image. Consequently, a fluorescence image is normalized by a red light image. The color of mucosa inside a human body is dominated by an amount of hemoglobin that is a pigment. As shown in FIG. 24, hemoglobin is characteristic of a large absorbance of light with wavelengths of 600 nm or shorter.

In this embodiment, normalization is carried out using an image depicted by red light with wavelengths of 600 nm or longer as a reference image. A change in apparent intensity of fluorescence dependent on the positional relationship between a region to be observed and a distal end of an endoscope can be canceled with a little influence of an amount of hemoglobin. The signal IR" representing a normalized fluorescence image can therefore be used as a signal accurately indicating the intensity of actual fluorescence or the degree of accumulation of an antibody labeled by indocyanine green.

The signal IR" output from the division circuit 87 is input to the marker production circuit 88. The marker production circuit 88 produces markers marking high signal levels of the signal IR" and also produces an image graphically indicating the high levels of the signal IR" marked by the markers.

An output of the multiplexer 86 and an output of the marker production circuit 88 are input to the image synthesis circuit 89, whereby image synthesis is carried out. The image synthesis circuit 89 synthesizes (superimposes) image signals representing the markers and graph produced by the marker production circuit 88 with an image signal output from the multiplexer 86, and outputs a synthetic image.

A synthetic image signal output from the image synthesis circuit 89 in the video signal processing circuit 73 is input to the D/A conversion circuit 74, converted into an analog signal, and input to the monitor 6. An image is then displayed. On the monitor 6, a normal light image and fluorescence image can be viewed according to setting determined by the screen display setting unit 75.

A user manipulates a switch on an operation unit of the endoscope which is not shown, and chooses any of four observation modes of (1) normal light sole observation, (2) fluorescence sole observation, (3) normal light/fluorescence synthesis observation, and (4) normal light/fluorescence marker observation. The screen display setting unit 75 sets a screen display on the basis of a screen display setting signal sent from the operation unit of the endoscope, and sends a setting signal to the multiplexer 86 and image synthesis circuit 89 in the video signal processing unit 73. At this time, a light emission control signal is sent from the screen display setting unit 75 to the light emission control circuit 67 in the light source apparatus 3D. Thus, light emission is controlled according to the setting of a screen display.

When normal light sole observation is designated, the lamp 61 alone glows under the control of the light emission control circuit 67 on the basis of a light emission control signal sent from the screen display setting unit 75. The infrared laser 63 stops emitting light. With a setting signal sent from the screen display setting unit 75, the multiplexer 86 and image synthesis circuit 89 in the video signal processing unit 73 are controlled. The multiplexer 86 selects an output destination so that a signal R' representing a red reflected light image will be applied to an input terminal 6R of the monitor, a signal G' representing a green reflected light image will be applied to an input terminal 6G thereof, and a signal B' representing a blue reflected light image will be applied to an input terminal 6B thereof. The image synthesis circuit 89 does not synthesize a marker image with a normal light image but outputs the signal representing the normal light image. As a result, the normal light image alone is displayed in colors on the monitor 6.

When fluorescence sole observation is designated, both the lamp 61 and infrared laser 63 glow under the control of the light emission control circuit 67 on the basis of a light emission control signal sent from the screen display setting unit 75. At this time, according to a setting signal sent from the screen display setting unit 75, the multiplexer 86 selects an output destination so that a signal IR' representing a fluorescence image will be applied to all the input terminals 6R, 6G, and 6B of the monitor. The image synthesis circuit 89 does not synthesize a marker image with the fluorescence image but outputs the signal representing the fluorescence image. As a result, the fluorescence image alone is displayed monochromatically on the monitor 6.

When normal light/fluorescence synthesis observation is designated, both the lamp 61 and infrared laser 63 glow under the control of the light emission control circuit 67 on the basis of a light emission control signal sent from the screen display setting unit 75. In this case, the lamp 61 is allowed to glow in order to enable the automatic light adjustment circuit 81 to adjust light and enable the amplification factor calculation circuit 84 to determine an amplification factor for a fluorescence image.

At this time, the multiplexer 86 selects an output destination according to a setting signal sent from the screen display setting unit 75 so that a signal G' representing a green reflected light image will be applied to the red input terminal 6R of the monitor 6 and blue input terminal 6B thereof, and a signal IR' representing a fluorescence image will be applied to the green input terminal 6G of the monitor 6.

The image synthesis circuit 89 does not synthesize a marker image with the reflected light and fluorescence images but outputs the signals representing the images. As a result, the reflected light image (green) and fluorescence image are displayed in different colors on the monitor 6. FIG. 23 shows the multiplexer 86 in the foregoing selected state.

An antibody labeled by indocyanine green is not accumulated in a normal mucosa inside a body. Images depicted by reflected light components that are green visible light are displayed in red and blue on the monitor. Green on the monitor gets very dark because of almost no fluorescence components. Consequently, the normal mucosa appears in purple on the monitor 6. Moreover, infrared fluorescence stems from a region in which the antibody labeled by indocyanine green is apt to be accumulated, such as, a carcinoma. The lesion is therefore displayed in greenish color on the monitor 6.

As mentioned above, in the normal light/fluorescence synthesis observation mode, a normal region can be distinguished from a lesion due to a difference in color. This is helpful in diagnosis. Moreover, since a green reflected light image well-reflects the structure-of the mucosa, the positional relationship between a fluorescence image and normal light image can be grasped easily.

When normal light/fluorescence marker observation is designated, both the lamp 61 and infrared laser 63 glow under the control of the light emission control circuit 67. At this time, the multiplexer 86 selects an output designation according to a setting signal sent from the screen display setting unit 75 so that a signal R' representing a red reflected light image will be applied to the red input terminal 6R of the monitor 6, a signal G' representing a green reflected light image will be applied to the green input terminal 6G thereof, and a signal B' representing a blue reflected light image will be applied to the blue input terminal 6B thereof.

The image synthesis circuit 89 synthesizes a marker image with a normal light image and outputs a resultant synthetic image. As a result, the normal light image is displayed on the monitor 6 with markers indicating high intensities of fluorescence superimposed on the normal light image. The levels (intensities of fluorescence) of the normalized fluorescence signal IR" associated with the markers are displayed graphically in a left lower area on the monitor screen. The possibility that a region indicated with a marker may be a lesion can be recognized at sight.

Figure 25:
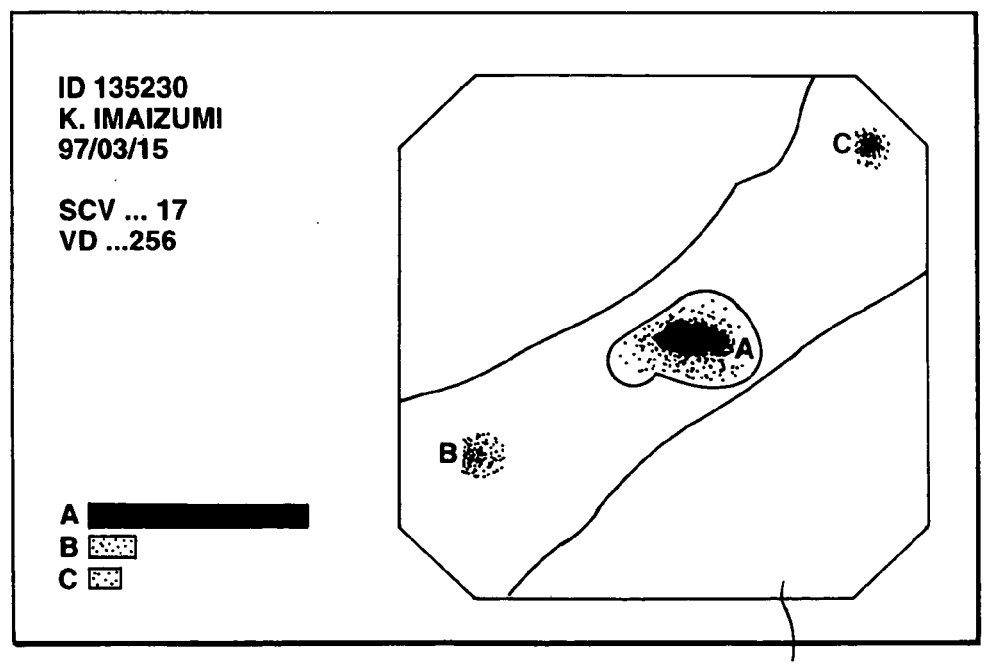

FIG. 25 shows an example of the above screen display on the monitor 6. In normal light/fluorescence marker observation, a normal light image 91 depicted by normal light is displayed in an octagonal area on the right hand of the screen. Regions fluorescing at high intensities are indicated with markers A, B, and C within the normal light image 91. Moreover, a graph is displayed in the left lower corner of the screen. The lengths of bars of the graph associated with the markers A, B, and C indicate the intensities IR" of fluorescence. If a display image has no portion thereof represented by the signal IR" with a given level or higher, no marker is displayed.

In this embodiment, visible light is also irradiated as illumination light for observation from a light source. Alternatively, red, green, blue, and infrared (excitation) light rays may be irradiated color-sequentially from the light source, and a CCD may be placed in the distal end of the insertional part of an endoscope. The signal processing method of this embodiment can still be adapted to this configuration.

Moreover, adjustment of amounts of light emanating from the lamp 61 and infrared laser 63 in the light source apparatus is not limited to adjustment using the illumination light diaphragm 65. Alternatively, an amount of emitted light may be controlled by controlling a current or voltage. Moreover, a light-emitting diode may be placed as a light source means at the distal end of the insertional part of an endoscope. Moreover, since illumination light for exciting a fluorescent substance is transmitted efficiently by a living tissue, the light may be irradiated in vitro.

Moreover, the camera head 4A may not be used as an imaging means. Alternatively, a light-receiving device such as a CCD may be incorporated in the processor 5C. The endoscope 2D and processor 5C may be connected using an optical connector. In this case, the endoscope can be designed to be lightweight and compact. Moreover, a single-plate camera having a mosaic filter on the face of the CCD may be substituted for the three-plate camera, and used to detect normal light. This results in reduced cost.

Moreover, a method of removing excitation light is not limited to the method in which the excitation light cutoff filter 23 is placed on the face of the image intensifier 24. Alternatively, a dichroic mirror characteristic of not reflecting excitation light components may be used as the dichroic mirror 22.

Normalization of a fluorescence image is not limited to normalization relative to a red light image. Alternatively, an image depicted by infrared fluorescence components may be used for the normalization.

Moreover, in fluorescence observation, instead of displaying a fluorescence image (IR') as it is, a normalized fluorescence image (IR") may be displayed on the monitor 6. Moreover, colors displayed on the monitor 6 are not limited to those based on red, green, and blue but may be those based on cyan, magenta, and yellow.

Moreover, color components of reflected light to be displayed on the monitor when normal light/fluorescence synthesis observation is designated are not limited to green light but may be red light. Moreover, green light and red light may be input as different color signals to the monitor. When normal light/fluorescence simultaneous observation is designated, an input terminal through which a fluorescence image signal (IR") is input is not limited to the green input terminal 6G of the monitor 6. Alternatively, the fluorescence image signal may be allocated to two or more input terminals among the red input terminal 6R, blue input terminal 6B, and green input terminal 6G.

This embodiment has the advantage described below.

According to this embodiment, both a fluorescence image and normal light image can be viewed simultaneously, and the intensity of fluorescence can be discerned accurately.

Next, the sixth embodiment of the present invention will be described. When a fluorescence image depicted by fluorescence emanating from an antibody labeled by indocyanine green (ICG) is viewed on a monitor, a region in which the fluorescent substance is not accumulated is visualized completely dark. An object of this embodiment is therefore to provide a fluorescent endoscope system making it possible to recognize the orientation (direction) of an object shown in an image even during fluorescence observation and making it easy to manipulate an endoscope or conduct an endoscopic treatment.

Figure 26:
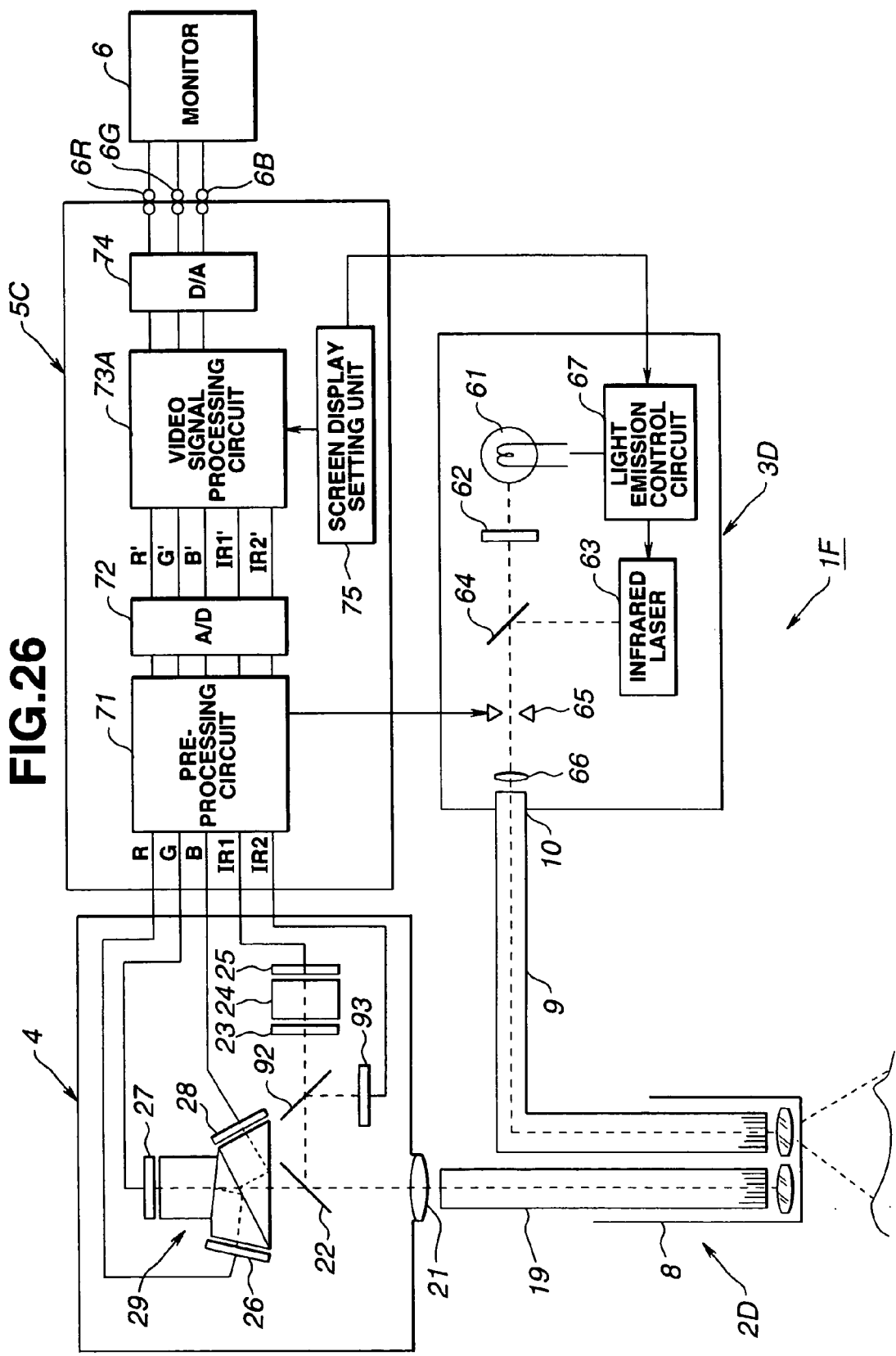
FIGS. 26 to 30 relate to the sixth embodiment.
Figure 27:
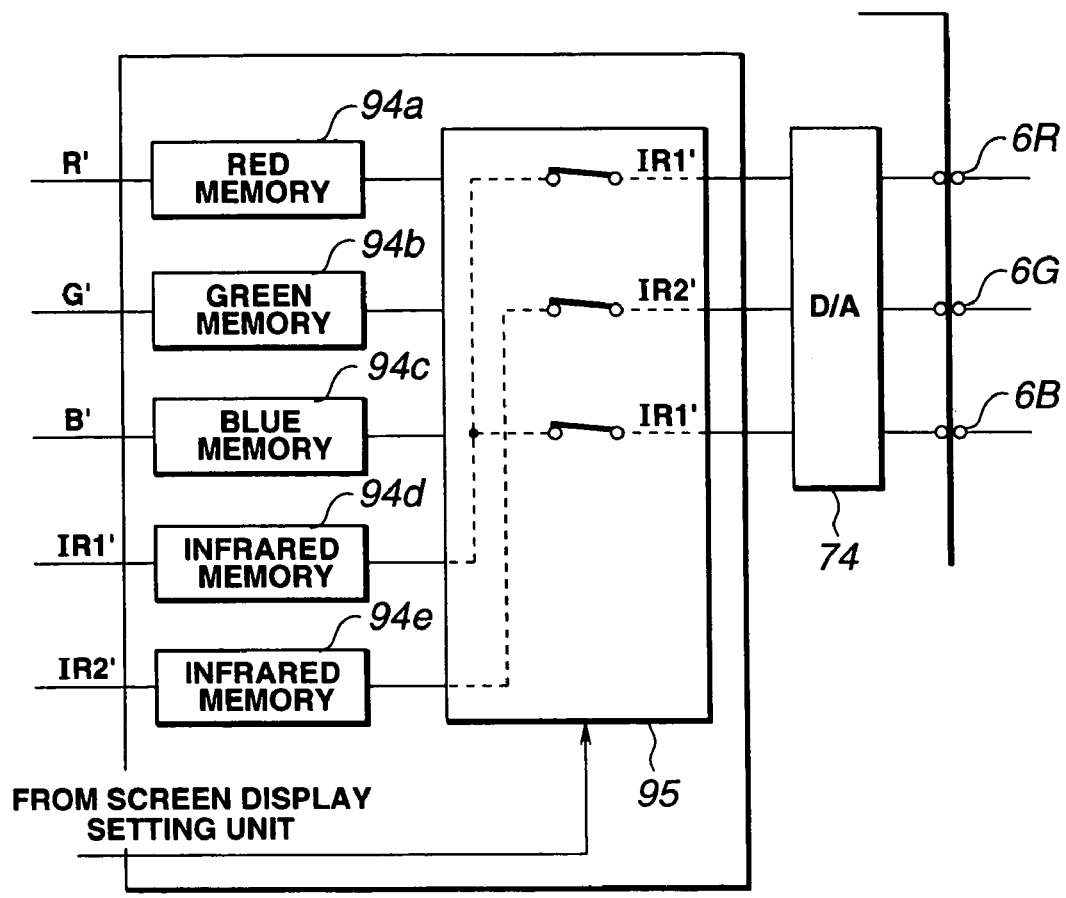

A fluorescent endoscope system 1F of the sixth embodiment of the present invention shown in FIG. 26 is different from the fluorescent endoscope system 1E of the fifth embodiment shown in FIG. 21 in points that a camera head 4C has a second dichroic mirror 92 and fifth CCD 93 in addition to the components of the camera head 4A and that a video signal processing circuit 73A having the configuration shown in FIG. 27 is substituted for the video signal processing circuit 73 in the processor 5C.

The second dichroic mirror 92 is placed on an optical path linking the dichroic mirror 22 for reflecting light with wavelengths of 700 nm or longer and the excitation light cutoff filter 23. As shown in FIG. 26, the dichroic mirror 92 is characteristic of reflecting light with wavelengths of less than 800 nm and transmitting light with wavelengths of 800 nm or longer.

The video signal processing circuit 73A shown in FIG. 27 is composed of five frame memories, in particular, red, green, and blue memories 94a, 94b, and 94c and two infrared memories 94d and 94e, and a multiplexer 95 for selecting an output destination for each of the frame memories. Selection performed by the multiplexer 95 is controlled by the screen display setting unit 75. FIG. 27 shows a selected state of the multiplexer 95 in which a fluorescence synthetic observation mode to be described later is selected.

Next, the operation of the sixth embodiment will be described by referring mainly to a difference from the fifth embodiment. Visible light and infrared excitation light emitted from the light source apparatus 3D are irradiated to a living tissue through the endoscope 2D. Reflected light and fluorescence stemming from the living tissue fall on the camera head 4C through the endoscope 2D.

Light incident on the camera head 4C has infrared light components and visible light components thereof separated therefrom by means of the dichroic mirror 22. The dichroic mirror 22 exhibits the characteristic shown in FIG. 3. The infrared light components reflected from the dichroic mirror 22 fall on the second dichroic mirror 92.

Figure 28:
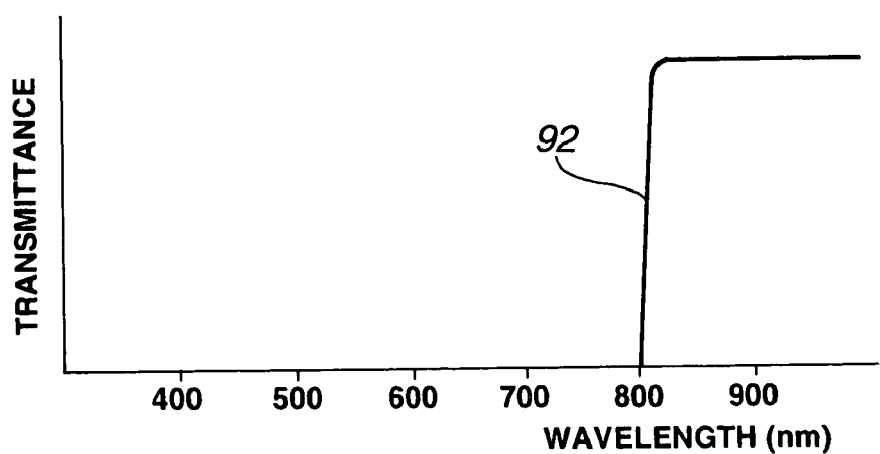

The second dichroic mirror 92 reflects, as seen from the characteristic curve shown in FIG. 28, excitation light components and transmits fluorescence components. The fluorescence components transmitted by the second dichroic mirror 92 have excitation light components, which cannot be removed perfectly by the second dichroic mirror 92, removed by the excitation light cutoff filter 23, are amplified by the image intensifier 24, and then detected by the first CCD 25. The excitation light cutoff filter 23 exhibits the spectroscopic characteristic of transmission shown in FIG. 4.

Moreover, light with wavelengths of 700 to 800 nm that is reflected light components of excitation light is detected by the fifth CCD 93. On the other hand, visible light components transmitted by the dichroic mirror 22 are, like the ones in the fifth embodiment, detected by the second, third, and fourth CCDs 26, 27, and 28.

Output signals of the CCDs 25, 26 to 28, and 93 (R, G, B, IR1, and IR2) are input to the pre-processing circuit 71 in the processor 5C. Herein, the signal R is an image signal representing red light, the signal G is an image signal representing green light, the signal B is an image signal representing blue light, the signal IR1 is an image signal representing infrared fluorescence, and the signal IR2 is an image signal representing reflected light of infrared excitation light.

The pre-processing circuit 71 carries out signal processing such as amplification of an image signal. A signal passed by the pre-processing circuit 71 is input to the A/D conversion circuit 72, converted into a digital signal, and then input to the video signal processing circuit 73A.

Signals output from the A/D conversion circuit 62 are temporarily stored in the frame memories, that is, the red, green, and blue memories 94a to 94c and the infrared memories 94d and 94e, and read according to the reading timing suitable to the format of a display on the monitor 6. According to an output signal of the screen display setting unit 75, the multiplexer 95 determines which of the signals (R', G', B', IR1', and IR2') that are output from the CCDs 25, 26 to 28, and 93 should be allocated to which of the red, green, and blue input terminals of the monitor 6 for display on the monitor 6.

A signal output from the multiplexer 95 is input to the D/A conversion circuit 74, converted into an analog signal, and input to the monitor 6. On the monitor, according to the setting defined by the screen display setting unit 75, a normal light image and fluorescence image are displayed. A user can view the normal light image and fluorescence image.

A screen display setting signal issued from a switch on an operation unit of the endoscope which is not shown is input to the screen display setting unit 75. A user can choose any of three modes of (1) normal light sole observation, (2) fluorescence synthetic observation, and (3) normal light/fluorescence dual-screen observation.

When normal light sole observation is designated, a light emission control signal is sent from the screen display setting unit 75 to the light emission control circuit 67. The lamp. 61 alone glows and the infrared laser 63 is turned off.

Moreover, a control signal is sent to the multiplexer 95 in the video signal processing circuit 73A. The multiplexer 95 selects an output destination so that a signal R' will be applied to the red input terminal 6R of the monitor 6, a signal G' will be applied to the green input terminal 6G thereof, and a signal B' will be applied to the blue input terminal 6B thereof. Consequently, a normal light image is displayed at a proper position on the monitor 6.

When fluorescence synthesis observation is designated, a light emission control signal is sent from the screen display setting unit 75 to the light emission control circuit 67. Both the lamp 61 and infrared laser 63 glow. At this time, the multiplexer 95 selects an output destination according to a setting signal sent from the screen display setting unit 75 so that a signal (IR2') representing an image depicted by reflected light of excitation light will be applied to the red input terminal 6R and blue input terminal 6B of the monitor 6 and a signal (IR') representing a fluorescence image will be applied to the green input terminal 6G of the monitor 6. On the monitor 6, the image depicted by reflected light of excitation light and the fluorescence image are displayed in different colors at the same position.

Figure 29:
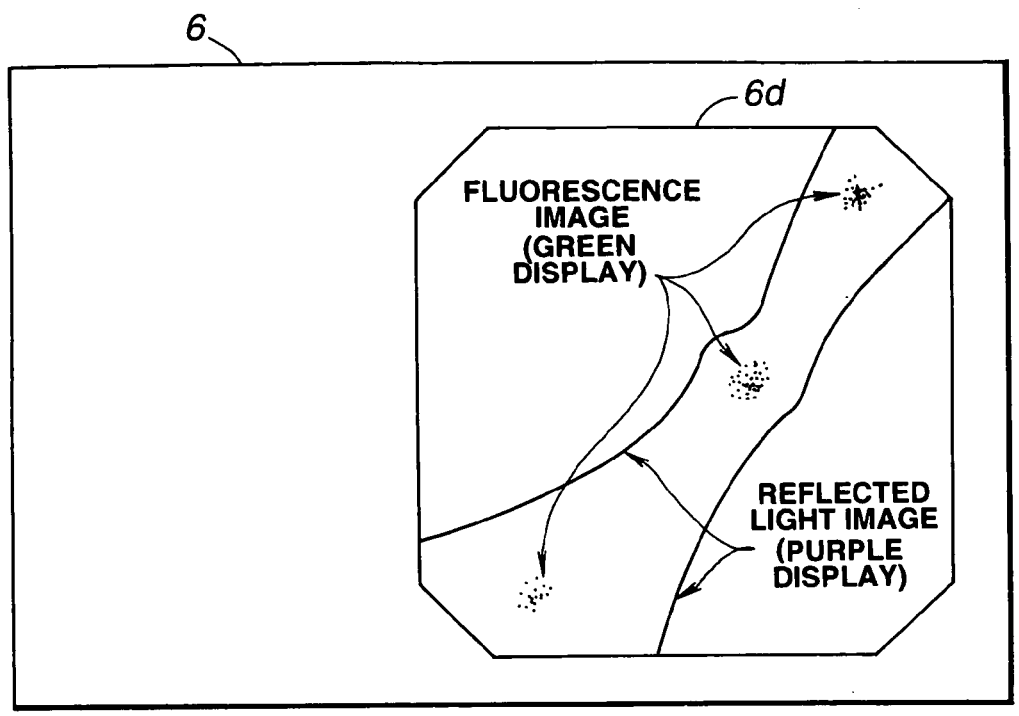

For example, as shown in FIG. 29, displayed on the monitor is a fluorescence synthetic image 6*d* in which a contour or the like of an object depicted by reflected light components of infrared excitation light is expressed in purple, and a lesion depicted by fluorescence components is expressed in green.

An antibody labeled by ICG is not accumulated in a normal mucosa in a living body. Reflected light components of infrared excitation light are therefore output as red and blue light components to the monitor 6. An image depicted by fluorescence components or green light components and displayed on the monitor 6 gets very dark. The normal mucosa is therefore expressed in purple on the monitor 6.

By contrast, a region in which the antibody labeled by ICG is apt to be accumulated, such as, a carcinoma fluoresces in the infrared spectrum. Green light components to be output to the monitor 6 get more intense. Since excitation light components are absorbed by the antibody labeled by ICG, reflected light components (red and blue light components on the monitor 6) of the excitation light get weaker. Consequently, the lesion is expressed in bright green on the monitor 6.

As mentioned above, a normal region and lesion are displayed in different tones. The lesion can therefore be detected easily due to a difference in color. Moreover, the endoscope 2D can be manipulated while reflected light of excitation light is referenced. When the endoscope 2D is manipulated, the orientation of the endoscope can be recognized easily. Even when forceps are used for biopsy, the endoscope can be manipulated reliably. Thus, maneuverability can be improved.

Figure 30:
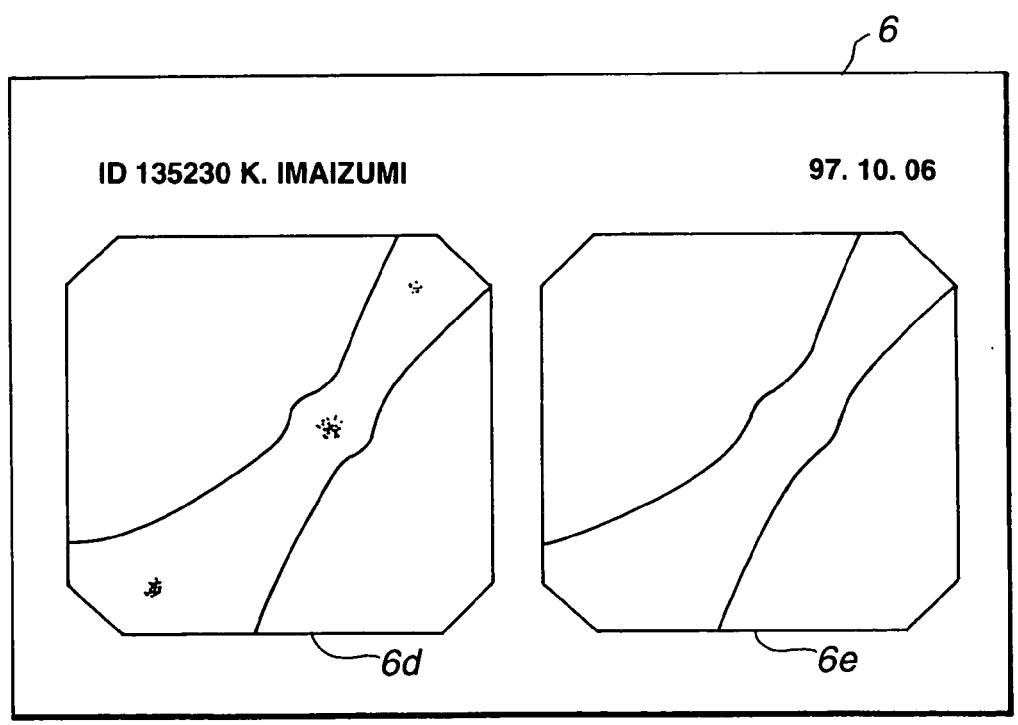

When normal light/fluorescence dual-screen observation is designated, a light emission control signal is sent from the screen display setting unit 75 to the light emission control circuit 67. Both the lamp 61 and infrared laser 63 glow. In the video signal processing circuit 73A, the memories and multiplexer 95 are controlled by a control circuit that is not shown so that the same image as the one displayed in normal light sole observation can be displayed on the right half of the monitor 6 and the same image as the one displayed in fluorescence synthetic observation can be displayed on the left half of the monitor 6. FIG. 30 shows an example of images displayed on the monitor 6 in this mode.

In the example of a display shown in FIG. 30, both a normal light image 6*e* and fluorescence image (more particularly, a fluorescence synthetic image) 6*d* are displayed.

In normal light/fluorescence dual-screen observation, the normal light image 6*e* and fluorescence image 6*d* can be viewed on the same monitor 6 without the necessity of switching the images. Diverse diagnoses can be carried out simultaneously, for example, while a tumorous lesion is observed in the fluorescence image 6*d*, the cured state of ulcer can be assessed by checking the tone of the normal light image 6*e* or the running state of vessels.

The sizes of the normal light image 6*e* and fluorescence image 6*d* to be displayed in normal light/fluorescence dual-screen observation are not limited to the same size adopted in this embodiment. Alternatively, the fluoroscence image 6*d* may be displayed in a smaller size as a child screen, the normal light image 6*e* may be displayed in a smaller size as a child screen, or the images may be able to be switched.

When fluorescence synthetic observation is designated, a signal representing a fluorescent image (IR1') is input to the monitor 6. The input terminal of the monitor 6 through which the signal is input is not limited to the green input terminal 6G of the monitor 6 but may be the red input terminal 6R or blue input terminal 6B thereof. Alternatively, the signal may be allocated to two or more of the red, green, and blue input terminals so that the signal can be input through two or more input terminals.

According to this embodiment, a fluorescence image and an image depicted by reflected light of excitation light can be displayed while one of the images is superposed on the other. The orientation of an endoscope can therefore be recognized clearly. When the endoscope is manipulated in order to carry out an endoscopic treatment while the fluorescence image is viewed, safety can be guaranteed.

Moreover, when a fluorescence image and an image depicted by reflected light of excitation light are displayed while one of the images is superposed on the other, the images are displayed in different colors. A lesion and the contour or structure of an object can be identified and easily discerned simultaneously. Diagnosis can therefore be achieved properly, and an endoscopic treatment can be carried out properly.

Next, the seventh embodiment of the present invention will be described. In general, fluorescence observed after irradiation of excitation light is feeble and much darker than reflected light observed after irradiation of normal light. According to a prior art, therefore, it is hard to produce both a fluorescence image and normal light image with proper brightness.

Accordingly, an object of this embodiment is to provide a fluorescent endoscope system making it possible to observe an object brightly during fluorescence observation and observe the object with a large depth of field during normal light observation.

Figure 31:
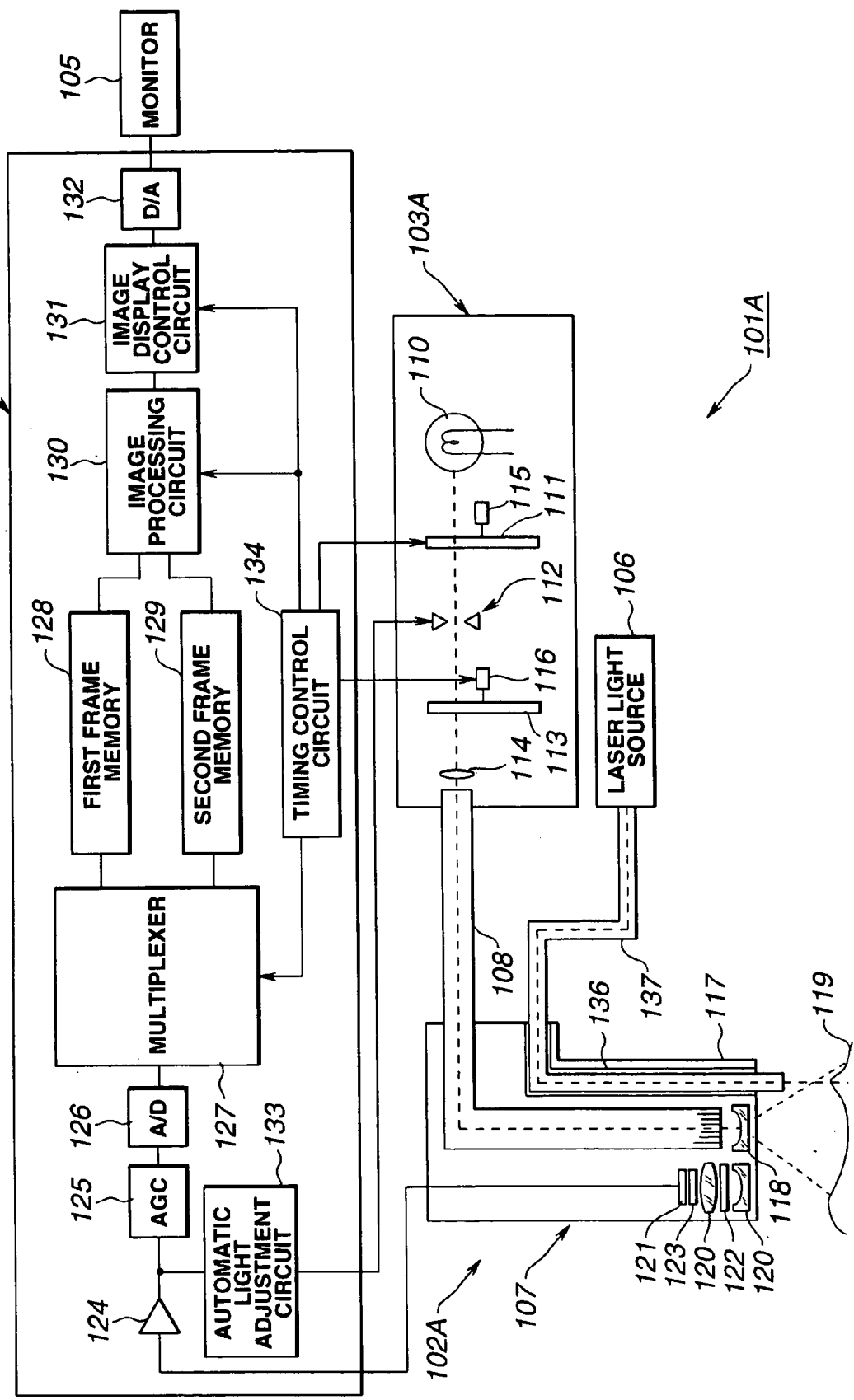

A fluorescent endoscope system 101A in accordance with the seventh embodiment of the present invention shown in FIG. 31 comprises an electronic endoscope 102A to be inserted into a body cavity for observation, a light source apparatus 103A for emitting light for normal observation and light for excitation, a processor 104A for carrying out signal processing, a monitor 105 for displaying an image depicted by normal light and an image depicted by fluorescence, and a laser light source 106 for emitting laser light used for a treatment.

The electronic endoscope 102A has an elongated insertional part 107 to be inserted into a body cavity. An imaging means is incorporated in a distal part 117 of the insertional part 107. A light guide fiber 108 over which illumination light used for normal observation and excitation light are propagated is run through the insertional part 107. An incident end of the light guide fiber 108 to be placed near an operator's hand can be freely detachably attached to the light source apparatus 103A.

The light source apparatus 103A includes a lamp 110 for radiating light with wavelengths in the infrared spectrum and visible spectrum, a rotary filter 111 located on the path of illumination light emanating from the lamp 110 for restricting a spectrum, an illumination light diaphragm 112 for restricting an amount of light emanating from the lamp 110, an RGB rotary filter 113, and a condenser 114 for concentrating light.

The spectrum restriction filter 111 and RGB rotary filter 113 are driven to rotate by motors 115 and 116 respectively.

Figure 32:
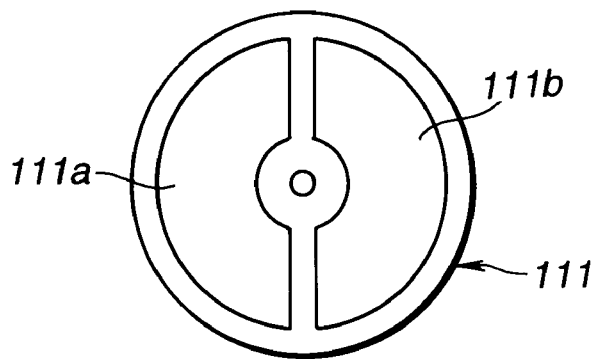
Figure 33:
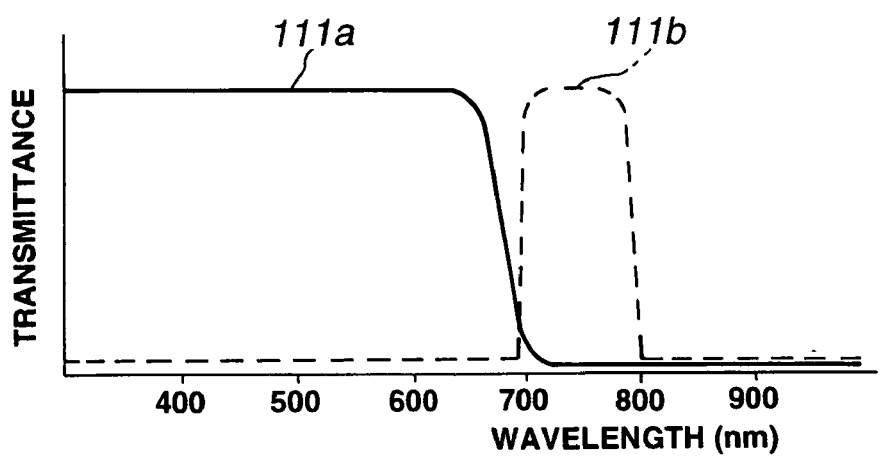

The spectrum restriction filter 111 has, as shown in FIG. 32, a visible light transmission filter 111a and an infrared light transmission filter 111b. FIG. 33 shows the characteristic of the visible light transmission filter 111a concerning transmission and the characteristic of the infrared light transmission filter 111b concerning transmission.

Only light components with wavelengths in the visible spectrum or infrared spectrum are extracted from light emanating from the lamp 110 by means of the visible light transmission filter 111a or infrared light transmission filter 111b. The amount of extracted light is controlled by the illumination light diaphragm 112. The resultant light then falls on the RGB rotary filter 113.

Figure 34:
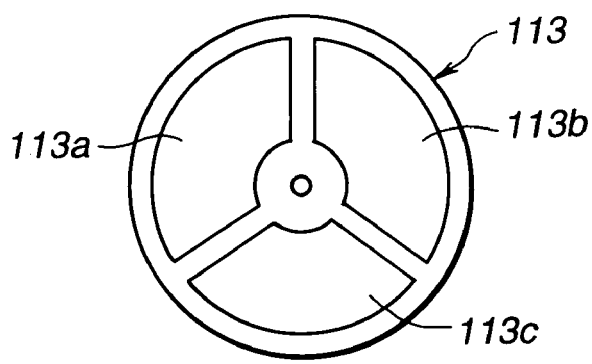

The RGB rotary filter 113 is, as shown in FIG. 34, composed of and trisected circumferentially into red, green, and blue transmission filters 113a, 113b, and 113c. When the RGB rotary filter is driven to rotate by a motor 116, the transmission filters are successively inserted into the optical path.

Figure 35:
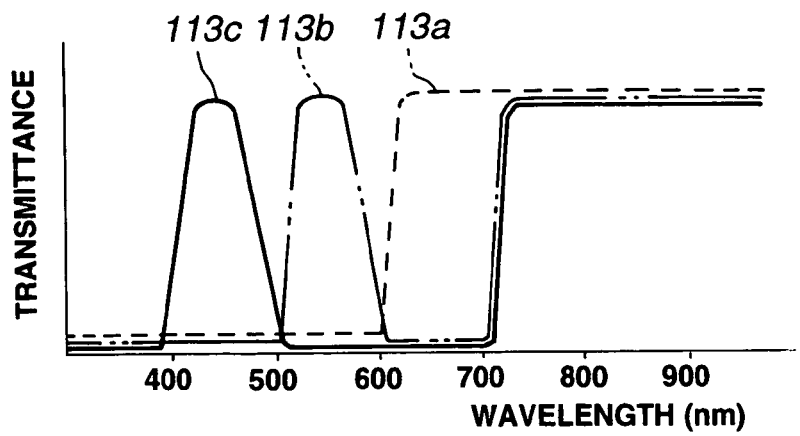

FIG. 35 shows the characteristics of the red, green, and blue transmission filters 113a, 113b, and 113c concerning transmission. According to the spectroscopic characteristics of transmission, the red, green and blue transmission filters 113a, 113b, and 113c transmit light with wavelengths permitting excitation of an antibody labeled by ICG as well as red, green, and blue light rays.

Light passed by the RGB rotary filter 113 is concentrated by the condenser 114 and irradiated to the incident end of the light guide fiber 108. The light is propagated along the light guide fiber 108, and emitted from the distal end of the light guide fiber 108 locked in the distal part 117 of the insertional part 107 to an examined object 119 in the body cavity through the illumination lens 118 attached to an illumination window.

When an antibody labeled by ICG is administered as a fluorescent substance having an affinity for a lesion such as a carcinoma to the examined object 119, the fluorescent substance is excited by infrared light with wavelengths of about 770 to 780 nm. Fluorescence with wavelengths in the infrared spectrum of about 810 to 820 nm is generated.

The distal part 117 has an observation window adjacently to the illumination window. An objective lens 120 is attached to the observation window. Reflected light and fluorescence stemming from the illuminated examined object 119 are converged to form images at an image formation position. A CCD 121 is placed as a solid-state imaging device at the image formation position. The CCD 121 photoelectrically converts the converged light. The objective lens system 120 and CCD 121 constitute an imaging means.

In this embodiment, a filter diaphragm 122 exhibiting the characteristic of transmission dependent on specified wavelengths is placed as a diaphragm means for restricting an amount of incident light on an optical path linking the objective lens system 120 and CCD 121. Moreover, an excitation light cutoff filter 123 for cutting off excitation light is also placed.

Figure 36:
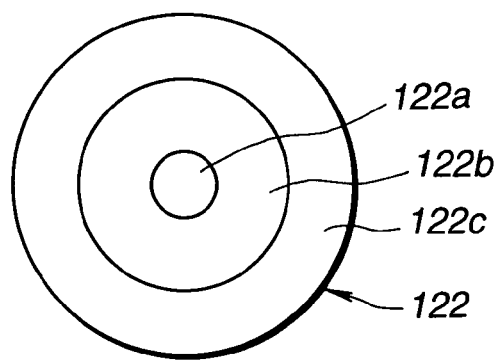

The filter diaphragm 122 is, as shown in FIG. 36, coaxially trisected.

Specifically, the filter diaphragm 122 has a circular visible light transmission area 122a formed along an innermost circumference, an annular visible light non-transmission area 122b formed outside the area 122a, and an annular light interception area 122c formed outside the area 122b.

Figure 37:
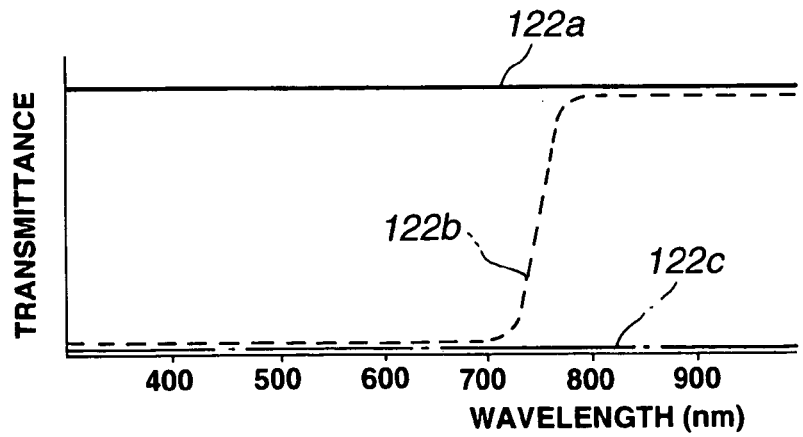

FIG. 37 shows the characteristics of the visible light transmission area 122a, visible light non-transmission area 122b, and light interception area 122c concerning transmission.

The visible light transmission area 122a that is the smallest innermost circular area exhibits a nearly flat characteristic of transmission in relation to the visible spectrum and infrared spectrum. The visible light non-transmission area 122b is characteristic of not transmitting visible light but transmitting light with wavelengths of fluorescence in the infrared spectrum. For visible light, since only the visible light transmission area 122a that has the smallest sectional area or the smallest transmission field transmits the visible light, the filter diaphragm 122 therefore plays a role of a diaphragm providing a small magnitude of open. For fluorescence with wavelengths in the infrared spectrum, since both the visible light transmission area 122a and visible light non-transmission area 122 transmit the fluorescence, the filter diaphragm 122 plays a role of a diaphragm providing a a large magnitude of open. Incidentally, the outermost light interception area 122c intercepts visible light and light with wavelengths in the infrared spectrum.

Figure 38:
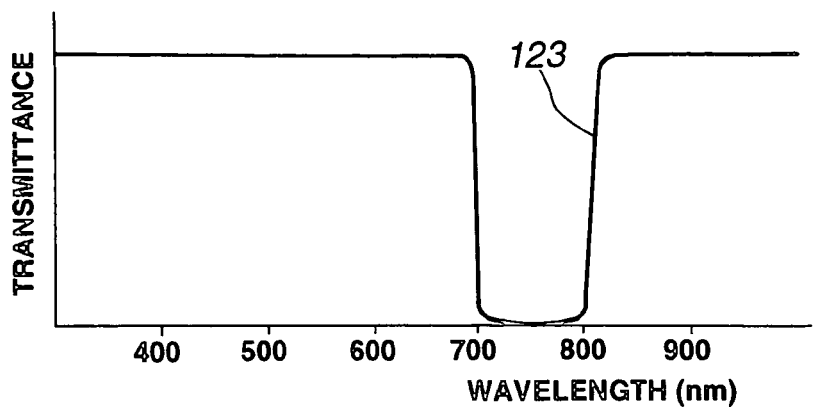

As shown in FIG. 38, the excitation light cutoff filter 123 cuts off light with wavelengths of 700 to 800 nm, and therefore intercepts excitation light incident on the CCD 121.

An image signal photoelectrically converted by the CCD 121 is sent to a pre-amplifier 124 included in the processor 104A for amplifying a signal, an automatic gain control (AGC) circuit 125 for automatically controlling the gain of a signal, an A/D conversion circuit 126, a multiplexer 127 for switching output destinations, a first frame memory 128 for temporarily storing an image, a second frame memory 129, an image processing circuit 130 for carrying out processing such as image enhancement, an image display control circuit 131 for controlling image display, and a D/A conversion circuit 132, and then output to the monitor 105.

The processor 104A includes an automatic light adjustment circuit 133 for controlling a magnitude of open, by which the illumination light diaphragm 112 opens, on the basis of a signal passing through the pre-amplifier 124, and a timing control circuit 134 for synchronizing the whole of the fluorescent endoscope system 101A.

A laser guide 137 for routing laser light is connected to the laser light source 106 for generating laser light for laser therapy. The laser guide 137 is structured to be inserted into a forceps channel 136 formed in the electronic endoscope 102A.

An observation mode selection switch is located on a front panel or the like of the processor 104A. Using the observation mode selection switch, any of a normal observation mode in which a normal endoscopic image depicted by visible light is used for observation, a fluorescence observation mode in which a fluorescence image depicted by fluorescence is used for observation, and a fluorescence/normal light observation mode in which the fluorescence image and normal endoscopic image are used for observation can be selected.

Specifically, when the observation mode selection switch is used for selection, an instruction is input to the timing control circuit 134. The timing control circuit 134 controls switching of the motors 115 and 116 and switching by the multiplexer 127. Thus, control is given according to a selected one of the modes explained in FIGS. 39 to 41.

For example, when the normal observation mode is selected, the timing control circuit 134 controls a magnitude of rotation of the motor 115 so that the visible light transmission filter 111a of the spectrum restriction rotary filter 111 will be locked on the optical path, and controls rotation of the motor 116 so that the RGB rotary filter 113 will rotate 30 times per second.

An image signal produced by the CCD 121 under illumination in this state, that is, under successive illumination of red, green, and blue light is stored in the first frame memory 128 or second frame memory 129 by controlling switching by the multiplexer 127.

Furthermore, when the fluorescence/normal light observation mode is selected, the timing control circuit 134 controls rotation of the motor 115 so that the spectrum restriction rotary filter 111 will rotate 90 times per second, and controls rotation of the motor 116 so that the RGB rotary filter 113 will rotate 30 times per second.

Moreover, image signals representing red light, fluorescence, green light, fluorescence, blue light, and fluorescence and resulting from imaging by the CCD 121 performed sequentially under illumination in the above state, that is, performed under successive illumination of red, infrared, green, infrared, blue, and infrared light rays are controlled by controlling switching by the multiplexer 127 so that image signals representing visible light will be stored in the first frame memory 128, and image signals representing fluorescence will be stored in the second frame memory 129.

In this embodiment, a diaphragm means formed with the filter diaphragm 122 for restricting an amount of incident light is located on the optical path of the imaging means. The filter diaphragm 122 has the visible light transmission area 122a and visible light non-transmission area 122b formed so that the center small circular part of the filter diaphragm 122 opens to transmit visible light, and the center small circular part of the filter diaphragm and the annular part outside the center part open to transmit fluorescence. For visible light, an amount of incident light is reduced greatly so that an image demonstrating a large depth of field can be produced. For fluorescence, the amount of incident light is not reduced very much so that a bright image can be produced.

Next, the operations of the fluorescent endoscope system 101A having the aforesaid components will be described. A fluorescent substance having an affinity for a lesion such as a carcinoma, being excited with light with wavelengths in the infrared spectrum, and fluorescing in the infrared spectrum, for example, an antibody labeled by ICG is administered to the examined object 119.

The antibody labeled by ICG is excited with irradiation of infrared light with wavelengths of about 770 to 780 nm, and fluoresces in the infrared spectrum of about 810 to 820 nm.

When excitation light is irradiated to inside of a body, a large amount of fluorescence emanates from a lesion. The presence or absence of the lesion can therefore be recognized by detecting the fluorescence.

The lamp 110 in the light source apparatus 103A is a xenon lamp and radiates light with wavelengths in a spectrum including the visible spectrum and the spectrum of wavelengths of excitation light for exciting an antibody labeled by ICG. Light radiated from the lamp 110 falls on the spectrum restriction rotary filter 111.

The spectrum restriction rotary filter 111 is, as shown in FIG. 32, composed of a visible light transmission filter 111a that is a half of a circular filter disk, and an infrared light transmission filter 111b that is the other half thereof.

The visible light transmission filter 111a is a bandpass filter for, as indicated with the spectroscopic characteristic curve of transmission drawn with a solid line in FIG. 33, transmitting light with wavelengths in a spectrum including the visible spectrum and the spectrum of wavelengths of red, green, and blue light rays. The infrared light transmission filter 111b is a bandpass filter for, as indicated with a dashed line, transmitting light with the wavelengths of excitation light for exciting an antibody labeled by ICG and cutting off light with the wavelengths of fluorescence.

Light passed by the spectrum restriction rotary filter 111 has an amount thereof adjusted by the illumination light diaphragm 112 and then falls on the RGB rotary filter 113.

The RGB rotary filter 113 is, as shown in FIG. 34, composed of red, green, and blue filters 113a, 113b, and 113c which are trisections of a filter disk. The spectroscopic characteristics of the filters concerning transmission are, as shown in FIG. 35, such that the filters transmit light with wavelengths in the spectrum of wavelengths of red, green, and blue light rays as well as light with wavelengths in the spectrum of wavelengths of excitation light for exciting an antibody labeled by ICG.

In normal light observation, the visible light transmission filter 111a of the spectrum restriction rotary filter 111 is locked on the optical path, and the RGB rotary filter 13 is rotated 30 times per second. Thus, red, green, and blue light rays are irradiated successively (See FIG. 39).

In fluorescence observation, the infrared light transmission filter 111b of the spectrum restriction rotary filter 111 is locked on the optical path, and the RGB rotary filter 113 is rotated 30 times per second. Thus, infrared light with wavelengths in the spectrum of wavelengths of excitation light is irradiated (See FIG. 40).

For simultaneously viewing both a fluorescence image and normal light image, the RGB rotary filter 113 is rotated 30 times per second and the spectrum restriction rotary filter 111 is rotated 90 times per second. Thus, red light, excitation light, green light, excitation light, blue light, and excitation light are irradiated successively (See FIG. 41).

At this time, the timing control circuit 134 gives control so that the RGB rotary filter 113 and spectrum restriction rotary filter 111 can rotate synchronously.

Light transmitted by the RGB rotary filter 113 falls on the incident end of the light guide fiber 108 in the electronic endoscope 102A, and propagates along the light guide fiber 108. The light is then irradiated from the distal end of the light guide fiber 108 to the examined object 119. The optical systems in the electronic endoscope 102 and light source apparatus 103A are designed to cope with light with wavelengths in the infrared spectrum. In the examined object 119, irradiated light is absorbed or reflected by a living tissue, and fluorescence is emitted from the administered fluorescent substance accumulated in a lesion.

Reflected light and fluorescence stemming from the examined object 119 is passed by the filter diaphragm 122 and excitation light cutoff filter 123 placed on the optical path, and then imaged by the CCD 121. The filter diaphragm 122 is, as shown in FIG. 36, composed of the visible light transmission area 122a, visible light non-transmission area 122b, and light interception area 122c. The areas exhibit the spectroscopic characteristics of transmission shown in FIG. 37.

The visible light non-transmission area 122b does not transmit visible light but transmit light with wavelengths in the spectrum of wavelengths of fluorescence within the infrared spectrum. For visible light, since the visible light transmission area 122a alone of the filter diaphragm 122 transmits light, the filter diaphragm 122 serves as a diaphragm providing a small magnitude of open. For infrared fluorescence, since both the visible light transmission area 122a and visible light non-transmission area 122b transmit light, the filter diaphragm 122 serves as a diaphragm providing a large magnitude of open.

In normal light (visible light) observation, a sharp visible light image demonstrating a large depth of field is formed on the CCD 121. In fluorescence observation, a bright fluorescence image is formed on the CCD 121. In normal light observation using visible light, a sharp image is needed for identifying a lesion in terms of the color or shape of a living tissue. However, fluorescence observation is regarded as assessment of presence. In fluorescence observation, presence or absence of a lesion is merely detected by checking the level of brightness of an image. It is therefore required to produce a brighter image other than a sharp image demonstrating a high spatial resolution. This embodiment satisfies this requirement.

The excitation light cutoff filter 123 is designed to cut off excitation light components emanating from an antibody labeled by ICG, and to transmit fluorescence components and visible light components. The excitation light cutoff filter 123 exhibits the spectroscopic characteristic of transmission shown in FIG. 38.

The CCD 121 receives red, green, and blue visible light rays or infrared fluorescence according to the positions of the RGB rotary filter 113 and spectrum restriction rotary filter 111. The CCD 121 is driven synchronously with the rotations of the RGB rotary filter 113 and spectrum restriction filter 111 by means of a CCD drive circuit that is not shown, and forms 180 frame images or 90 frame images per second according to whether or not the spectrum restriction rotary filter 111 has rotated (See FIGS. 39 to 41).

An electric signal output from the CCD 121 is input to the preamplifier 124 in the processor 104A. After amplified, the gain of the signal is controlled by the AGC circuit 125. Thereafter, the signal is input to the A/D conversion circuit 126 and converted into a digital signal. The digital signal is stored in the first frame memory 128 or second frame memory 129 selected by the multiplexer 127.

Based on a control signal sent from the timing control circuit 134, the multiplexer 127 routes a signal, which is produced with the visible light transmission area 111a of the spectrum restriction rotary filter 111 inserted to the optical path, to the first frame memory 128, and routes a signal, which is produced with the infrared light transmission area 111b inserted thereto, to the second frame memory 129.

The first and second frame memories 128 and 128 are each composed of three frame memories that are not shown. An image formed with the red filter 113a of the RGB rotary filter 113 inserted to the optical path, an image formed with the green filter 113b thereof inserted thereto, and an image formed with the blue filter 113c inserted thereto are recorded in the three frame memories respectively.

The three frame memories are read simultaneously, whereby color-sequential images sent time-sequentially are timed. Signals output from the first and second frame memories 128 and 129 are input to the image processing circuit 130, and subjected to image processing such as image enhancement and noise elimination. The resultant signals are input to the image display control circuit 131 and controlled for simultaneous display of a fluorescence image, normal light image, and character information.

A digital signal output from the image display control circuit 131 is input to the D/A conversion circuit 132, converted into an analog signal, and then output to the monitor 5. The automatic light adjustment circuit 133 sends a signal for use in controlling the illumination light diaphragm 112 so that illumination light of proper brightness can be irradiated. The timing control circuit 134 synchronizes rotations of the RGB rotary filter 113 and spectrum restriction filter 111, drive of the CCD, and various kinds of video signal processing.

On the monitor 105, depending on the position of the spectrum restriction rotary filter 111, a normal light image or fluorescence image can be viewed or both of them can be viewed simultaneously.

In this case, the normal light image displayed on the display surface of the monitor 105 is a sharp image demonstrating a large depth of field. By contrast, the fluorescence image is a bright image and helpful in diagnosis.

In this embodiment, both a normal light image and fluorescence image can be produced simultaneously. The embodiment therefore has the merit that an endoscope can be positioned easily for further observing a region, which is suspected to contain a lesion and observed in the fluorescence image, using a normal light image.

For laser therapy, laser light is emitted from the laser light source 106. The emitted laser light is irradiated to a lesion through the laser guide 137. The laser light source 106 is a semiconductor laser and emits laser light whose wavelengths are matched with those of excitation light for exciting an antibody labeled by ICG.

It will therefore not take place that a fluorescence image or normal light image is disturbed greatly with irradiation of laser light. Moreover, since laser light is well-absorbed by an antibody labeled by ICG, a lesion can be treated efficiently.

In this embodiment, a single lamp is used as a light source means for observation. Alternatively, two or more light sources, for example, a halogen lamp for normal light observation and a laser or light-emitting diode for use in exciting a fluorescent substance may be used in combination.

Moreover, illumination light for exciting a fluorescent substance may be irradiated in vitro.

Moreover, the function for cutting off excitation light is not limited to the one located on the face of the CCD 121 but may be located on the objective lens 120 or filter diaphragm 122.

The position of the CCD 121 is not limited to the position in the display part 117 of the insertional part 107 of the electronic endoscope 102A. Alternatively, the CCD 121 may be placed inside the processor 104A and light may be routed by the image guide filter. Otherwise, the CCD 121 may be placed in the camera head that is attachable or detachable to or from the optical endoscope.

Moreover, an image intensifier may be located on the face of the CCD 121 in order to improve sensitivity.

Moreover, field-by-field processing may be adopted instead of frame-by-frame processing.

This embodiment has the advantages described below.

Since the area of a diaphragm for transmitting fluorescence is made larger than the area thereof for transmitting visible light (normal light), a large amount of fluorescence can be passed by the diaphragm. An image depicted by the fluorescence therefore gets brighter. An image depicted by the normal light demonstrates a larger depth of field.

Next, the eighth embodiment of the present invention will be described.

An object of this embodiment is to provide a fluorescent endoscope system making it possible to view a brighter image little affected by a noise under fluorescence, and to view an image with a little blur, which demonstrates a larger depth of field, under normal light.

The eighth embodiment is configured similarly to the seventh embodiment. Differences will be described mainly. The same reference numerals will be assigned to the components having similar functions, and the description of the components will be omitted.

Figure 42:
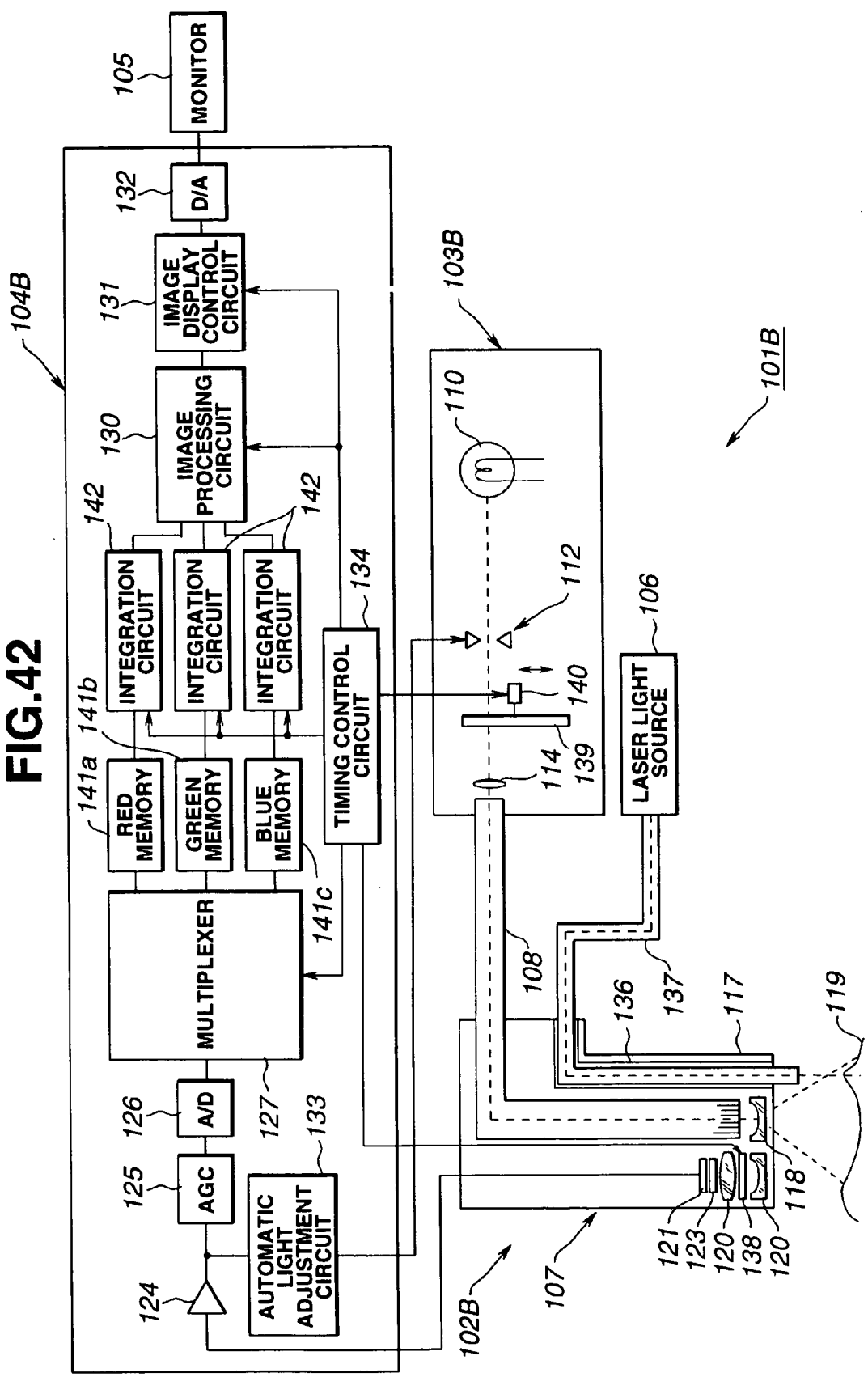

A fluorescent endoscope system 101B of the eighth embodiment shown in FIG. 42 is different from the fluorescent endoscope system 101A shown in FIG. 31 in points that an electronic endoscope 102B adopts a liquid-crystal diaphragm 138 using a liquid crystal in place of the filter diaphragm 122 included in the electronic endoscope 102A, that a light source apparatus 103B does not include the spectrum restriction filter 111 included in the light source apparatus 103A but employs a parallel rotary filter 139 for restricting wavelengths of transmitted light in place of the RGB rotary filter 113, and that a processor 104B has red, green, and blue memories 141a, 141b, and 141c in place of the first frame memory 128 and second frame memory 129 included in the processor 104A and includes three integration circuits 142.

Figure 43:
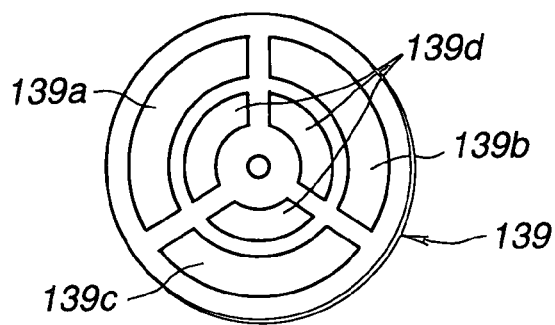
FIGS. 42 to 46 relate to the eighth embodiment.

The parallel rotary filter 139 in the light source apparatus 103B is driven to rotate by a motor 140. The motor 140 is controlled by the timing control circuit 134 so that the rotating speed will remain constant. The parallel rotary filter 139 has, as shown in FIG. 43, red, green and blue filters 139a, 139b, and 139c along the outer circumference thereof and has three infrared filters 139d along the inner circumference thereof. The parallel rotary filter 139 is movable in directions orthogonal to the axis of rotation (vertical directions in FIG. 42). In normal observation, the red, green, and blue filters 139a, 139b, and 139c formed along the outer circumference are inserted into the optical path. In fluorescence observation, the infrared filters 139d formed along the inner circumference are inserted.

Figure 44:
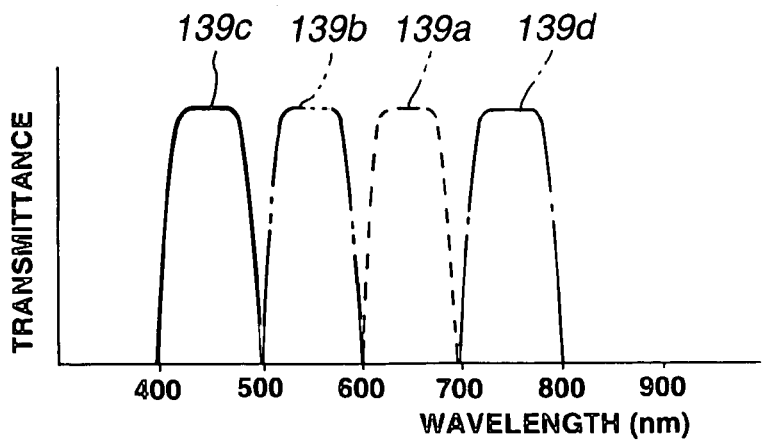

The red, green, and blue filters 139a, 139b, and 139c, and the infrared filters 139d exhibit the characteristics of transmission shown in FIG. 44. The red, green, and blue filters 139a, 139b, and 139c transmit red, green, and blue light components, and the infrared filters 139d transmit excitation light components for exciting an antibody labeled by ICG.

Figure 45:
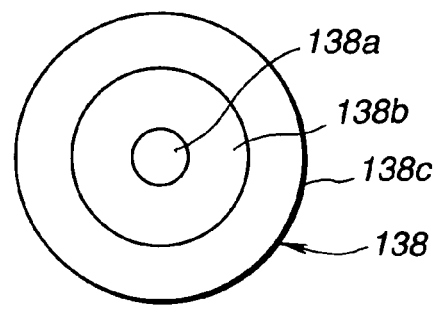

The liquid-crystal diaphragm 138 located on the optical path between the objective lens 120 and CCD 121 in the electronic endoscope 102B and designed for restricting an amount of transmitted light is, as shown in FIG. 45, concentrically divided into three portions.

Specifically, as shown in FIG. 45, the liquid-crystal diaphragm 138 is composed of an aperture 138a, liquid-crystal plate 138b, and light interceptor 138c in that order concentrically from the center thereof. A voltage to be applied to the liquid-crystal plate 138b is controlled by the timing control circuit 134.

The liquid-crystal plate 138b has the property of not transmitting light when a voltage is applied to the liquid-crystal plate but transmitting light when no voltage is applied thereto. When a voltage is applied, an opening provided by the diaphragm gets smaller, and a sharp image demonstrating a large depth of fields is formed on the CCD 121. When no voltage is applied, the opening provided by the diaphragm gets larger. A bright image is therefore formed on the CCD 121.

The processor 104B includes, like the one shown in FIG. 31, the preamplifier 124, AGC circuit 125, A/C conversion circuit 126, and multiplexer 127. A signal input to the multiplexer 127 is routed to the red memory 141a, green memory 141b, or blue memory 141c.

Output signals of the red memory 141a, green memory 141b, and blue memory 141c are input to the image processing circuit 130 via the integration circuits 142. An output of the image processing circuit 130 is, like that of the one shown in FIG. 31, output to the monitor 105 via the image display control circuit 131 and D/A conversion circuit 132.

The processor 104B includes the timing control circuit 134 for synchronizing the automatic light adjustment circuit 133 and the whole of the fluorescent endoscope system 101B and for controlling the rotation of the parallel rotary filter 139 and the operations of the liquid-crystal diaphragm 138 and integration circuits 142.

Figure 46:
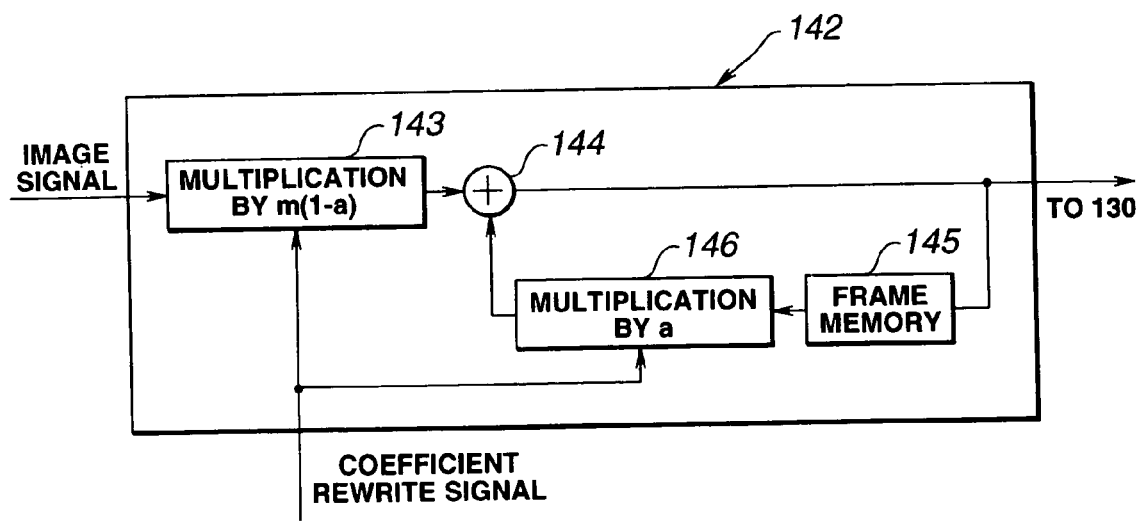

The integration circuits 142 are, as shown in FIG. 46, each composed of two multipliers 143 and 146 whose coefficients can be rewritten, an adder 144, and a frame memory 145.

Moreover, the laser light source 106 for generating laser light used for laser therapy and the laser guide 137 along which the laser light is routed are included.

Next, the operations of the fluorescent endoscope system 101B having the foregoing components will be described.

A fluorescent substance having an affinity for a lesion such as a carcinoma, such as, an antibody labeled by ICG is administered in advance to the examined object 119.

The lamp 110 in the light source apparatus 103B radiates light with wavelengths in a spectrum including the visible spectrum and a spectrum of wavelengths of excitation light for exciting the antibody labeled by ICG. The light radiated from the lamp 110 has the amount thereof adjusted by the illumination light diaphragm 112 and is then transmitted by the parallel rotary filter 139.

The light transmitted by the parallel rotary filter 139 falls on the incident end of the light guide fiber 108 of the electronic endoscope 102B. The parallel rotary filter 139 has, as shown in FIG. 43, the red filter 139a, green filter 139b, and blue filter 139c, which transmit red, green, and blue light rays respectively with wavelengths in the visible spectrum, formed along the outer circumference thereof, and has the infrared filters 139d, which transmit light with wavelengths in the infrared spectrum, formed along the inner circumference thereof.

The filters have the characteristics of transmission shown in FIG. 44. The infrared filters 139d transmit excitation light components for exciting an antibody labeled by ICG. During operation, the parallel rotary filter 139 rotates 30 times per second. The parallel rotary filter 139 is movable in directions perpendicular to the axis of rotation. In normal light observation, the red, green, and blue filters 139a, 139b, and 139c formed along the outer circumference are inserted into the path of illumination light, whereby red, green, and blue light rays are irradiated successively to the object. In fluorescence observation, the infrared filters 139d formed along the inner circumference are inserted into the path of illumination light, whereby infrared light with wavelengths in the spectrum of wavelengths of excitation light is irradiated.

Reflected light and fluorescence stemming from the examined object 119 are passed by the liquid-crystal diaphragm 138 and excitation light cutoff filter 123 and then imaged by the CCD 121. The liquid-crystal diaphragm 138 is, as shown in FIG. 45, composed of the aperture 138a, liquid-crystal plate 138b, and light interceptor 138c which are arranged in that order concentrically from the center. A voltage to be applied to the liquid-crystal plate 138b is controlled by the timing control circuit 134. The liquid-crystal plate 138b has the property of not transmitting light when a voltage is applied thereto but transmitting light when no voltage is applied thereto.

As shown in FIG. 47, in normal observation, a voltage is applied. Consequently, the diaphragm provides a small opening, and a sharp image demonstrating a large depth of field is formed on the CCD 121. Moreover, in fluorescence observation, no voltage is applied. Consequently, the diaphragm provides a large opening, and a bright image is formed on the CCD 121.

The excitation light cutoff filter 123 is designed to cut off excitation light components for exciting an antibody labeled by ICG and to transmit fluorescence components and visible light components. The excitation light cutoff filter exhibits the spectroscopic characteristic of transmission shown in FIG. 38.

The CCD 121 receives visible light rays of red, green, and blue or infrared fluorescence depending on the position of the parallel rotary filter 139. The CCD 121 is driven by a CCD drive circuit that is not shown synchronously with the rotation of the parallel rotary filter 139. In normal light observation, the CCD 121 forms 90 frame images per second. In fluorescence observation, the CCD 121 forms 30 frame images per second (See FIG. 47).

In fluorescence observation, the exposure time of the CCD 121 is made longer (three times longer in FIG. 47) than that in normal light observation in order to produce a brighter image.

An electric signal output from the CCD 121 is input to the preamplifier 124 in the processor 104B. After amplified, the gain of the signal is controlled by the AGC circuit 125. Thereafter, the signal is input to the A/D conversion circuit 126 and thus converted into a digital signal. The digital signal is stored to any of the three frame memories of the red memory 141a, green memory 141b, and blue memory 141c selected by the multiplexer 127.

Based on a control signal sent from the timing control circuit, the multiplexer 127 routes an input signal to the red memory 141a when the red filter 139a of the parallel rotary filter 139 is inserted into the optical path, to the green memory 141b when the green filter 139b or infrared filter 139d is inserted thereto, or to the blue memory 141c when the blue filter 139c is inserted thereto.

Data items carried by image signals sent from the three frame memories 141a, 141b, and 141c are read simultaneously, whereby color sequential images sent time-sequentially are timed. The digital signals output from the frame memories 141a, 141b, and 141c are subjected to noise elimination and amplification by means of the integration circuits 142.

The integration circuits 142 each have the configuration of a recursive filter shown in FIG. 46. An input image signal is multiplied by m(1−a) by means of the multiplier 143, and then input to the adder 144. The resultant signal is therefore added to an output of the multiplier 146 that multiplies an input by a. An output of the adder 144 is input to the frame memory 145 and also input to the image processing circuit 130.

In the frame memory 145, an image is delayed by one frame and then output. The coefficients set in the two multipliers 143 and 145 can be rewritten in response to a coefficient rewrite signal output from the timing control circuit 134.

In the recursive filter, the coefficient m denotes an amplification factor. The larger the coefficient m is, the brighter a produced image is. The larger a results in a greater effect of an afterimage. Consequently, a noise in an image is reduced.

In this embodiment, as shown in FIG. 47, the coefficient m is set to 1 for normal light observation and set to 2 for fluorescence observation. Thus, a brighter image can be produced under fluorescence. The coefficient a is set to 0.1 for normal light observation and to 0.5 for fluorescence observation. Thus, in fluorescence observation, a noise is reduced to a greater extent.

A clipping circuit for preventing a result of multiplication from becoming an overflow is incorporated in the multiplier 143.

Signals output from the integration circuits 142 are input to the image processing circuit 130 and subjected to image processing such as image enhancement. The resultant signals are input to the image display control circuit 131 and controlled for display of character information. A digital signal output from the image display control circuit 131 is input to the D/A conversion circuit 132, and converted into an analog signal. The analog signal is output to the monitor 105.

The automatic light adjustment circuit 133 sends a signal for use in controlling the illumination light diaphragm 112 so that illumination light of proper brightness can be irradiated. The timing control circuit 134 synchronizes rotation of the parallel rotary filter 139, drive of the CCD, and processing of various video signals, and controls a voltage to be applied to the liquid-crystal diaphragm 138 and the coefficients set in the multipliers 143 and 146 according to switching of visible light and infrared light by the parallel rotary filter 139.

In normal light observation using visible light, a voltage is applied to the liquid-crystal diaphragm 138 so that the diaphragm can provide a smaller opening. This results in a sharp image demonstrating a large depth of field. Moreover, values permitting suppression of a blur even when an object makes a quick motion are assigned to the coefficients set in the multipliers 143 and 146. For example, 1 and 0.1 are assigned to the coefficients m and a respectively.

In fluorescence observation using infrared light, no voltage is applied to the liquid-crystal diaphragm 138 so that the diaphragm can provide a larger opening. This results in a bright image. Moreover, values permitting exertion of a great effect of noise elimination and an effect of amplification are assigned to the coefficients set in the multipliers 143 and 146. For example, 2 and 0.5 are assigned to the coefficients m and a respectively.

On the monitor 105, depending on the position of the parallel rotary filter 139, a normal light image or fluorescence image can be viewed.

In this embodiment, a single lamp is employed as a light source means for observation. Alternatively, two or more light sources, for example, a halogen lamp for normal light observation and a laser or light-emitting diode for use in exciting a fluorescent substance may be used in combination.

Moreover, illumination light for exciting a fluorescent substance may be irradiated in vitro.

Moreover, the position of the CCD 121 is not limited to the position in the distal part 117 of the insertional part 107. Alternatively, the CCD 121 may be incorporated in the processor 104B and light may be introduced using an image guide fiber. Otherwise, the CCD 121 may be placed in the camera head attachable or detachable to or from the optical endoscope.

Moreover, an image intensifier may be placed on the face of the CCD 121, thus improving sensitivity.

Moreover, a diaphragm employed is not limited to a liquid-crystal diaphragm but may be a diaphragm made of a shape memory alloy. Alternatively, a light interceptive member may be thrust and plunged mechanically.

Moreover, the three filters 139d for excitation (formed along the inner circumference) of the parallel rotary filter 139 are not limited to filters having the same characteristic of transmission such as the ones in this embodiment. Alternatively, for example, one of the filters may be designed to transmit light with wavelengths of about 900 nm and to thus receive reflected light of infrared.

Owing to this configuration, an image made by superposing a reflected light image depicted by light with wavelengths of about 900 nm on a fluorescence image can be viewed on the monitor. It will therefore not take place that a region in which an antibody labeled by ICG is not accumulated is seen completely dark. When the endoscope is manipulated while a fluorescence image is viewed, or when the endoscope is used for a treatment, safety can be guaranteed readily.

This embodiment has the advantages described below.

Since a diaphragm is controlled responsively to switching of fluorescence observation and normal light observation, a brighter image can be used for observation in fluorescence observation, and an image demonstrating a large depth of field can be used for observation in normal light observation.

Moreover, the coefficients set in a recursive filter are changed responsively to switching of fluorescence observation and normal light observation. Fluorescence can be observed while little affected by a noise. Normal light can be observed in line with the quick motion of an object.

Moreover, the exposure time of the CCD 21 is varied responsively to switching of fluorescence observation and normal light observation. An object emitting feeble fluorescence can be observed more brightly.

Next, the ninth embodiment will be described.

An object of this embodiment is to provide a fluorescent endoscope system making it possible to observe an object, from which both fluorescence and normal light originate, at proper brightness.

This embodiment is configured similarly to the seventh embodiment. Differences will be described mainly. The same reference numerals will be assigned to components having similar functions. The description of the components will be omitted.

A fluorescent endoscope system 101C of the ninth embodiment shown in FIG. 48 is different from the fluorescent endoscope system 101A shown in FIG. 31 in points that an electronic endoscope 102C adopts a CCD 151 capable of varying an amplification factor internally in place of the CCD 121 employed in the electronic endoscope 102A, and adopts a diaphragm 152 for restricting an amount of transmitted light in place of the filter diaphragm 122, that a light source apparatus 103C includes a lamp light emission control circuit 153 for controlling glowing of a lamp 110 in addition to the components of the light source apparatus 103A, and that a processor 104C includes a CCD drive circuit 154 for controlling the CCD 151 in addition to the components of the processor 104A.

The light source apparatus 103C includes, like the one shown in FIG. 31, the lamp 110 for radiating light, the spectrum restriction rotary filter 111 located on the path of illumination light for restricting the wavelengths of transmitted light, the illumination light diaphragm 112 for restricting an amount of light, the RGB rotary filter 113 for restricting the wavelengths of transmitted light, the condenser 114, and the lamp light emission control circuit 153 for controlling glowing of the lamp 110.

The spectrum restriction rotary filter 111 is, as shown in FIG. 32, bisected into the visible light transmission filter 111a and infrared light transmission filter 111b. The RGB rotary filter 113 is, as shown in FIG. 34, trisected into the red, green, and blue filters 113a, 113b, and 113c.

The electronic endoscope 102C includes the light guide filter 108 over which illumination light is propagated, the illumination lens 118 opposed to the distal end of the light guide fiber 108, a diaphragm for restricting an amount of passed light, the excitation light cutoff filter.123 for removing excitation light, and the CCD 151 in which an amplification factor is variable.

The processor 104C includes the preamplifier 124, AGC circuit 125, A/D conversion circuit 126, multiplexer 127, first frame memory 128, second frame memory 129, image processing circuit 130 for carrying out processing such as image enhancement, image display control circuit 131, D/A conversion circuit 132, automatic light adjustment circuit 133 for controlling the illumination light diaphragm 112, timing control circuit for synthesizing all the components of the fluorescent endoscope system 101C, and CCD drive circuit 154 for controlling the CCD 151.

Moreover, the laser light source 106 for generating laser light for the purpose of laser therapy and the laser guide 137 for guiding laser light are included.

Next, the operations of the fluorescent endoscope system 101C having the foregoing components will be described. A fluorescent substance having an affinity for a lesion such as a carcinoma, such as, an antibody labeled by ICG is administered to the examined object 119 in advance.

Light with wavelengths in a spectrum including the visible spectrum and the spectrum of wavelengths of excitation light for exciting the antibody labeled by ICG is radiated from the lamp 110 in the light source apparatus 103C. The light radiated from the lamp 110 is passed by the spectrum restriction rotary filter 111 and illumination light diaphragm 112, and transmitted by the RGB rotary filter 113. The light passed by the RGB rotary filter 113 falls on the light guide filter 108 of the electronic endoscope 102C.

The spectrum restriction rotary filter 111 has the structure shown in FIG. 32, and exhibits the spectroscopic characteristics of transmission shown in FIG. 33. The RGB rotary filter 113 has the structure shown in FIG. 34, and exhibits the spectroscopic characteristics of transmission shown in FIG. 35.

In normal light observation, as shown in FIG. 49, the lamp light emission control circuit 153 supplies a pulsating current of, for example, 18 A to the lamp. The lamp 110 glows synchronously with the rotation of the RGB rotary filter 113.

The visible light transmission filter 111a of the spectrum restriction rotary filter 111 is locked on the optical path. The RGB rotary filter 113 is rotated 30 times per second. Thus, red, green, and blue light rays are irradiated successively (See FIG. 49).

In fluorescence observation, the lamp light emission control circuit 153 supplies, as shown in FIG. 50, a pulsating current of 21 A. The lamp 110 glows synchronously with the rotation of the RGB rotary filter 113.

The infrared light transmission filter 111b of the spectrum restriction rotary filter 111 is locked on the optical path, and the RGB rotary filter 113 is rotated 30 times per second. Thus, infrared light with wavelengths in the spectrum of wavelengths of excitation light is irradiated (See FIG. 50).

Figure 51:
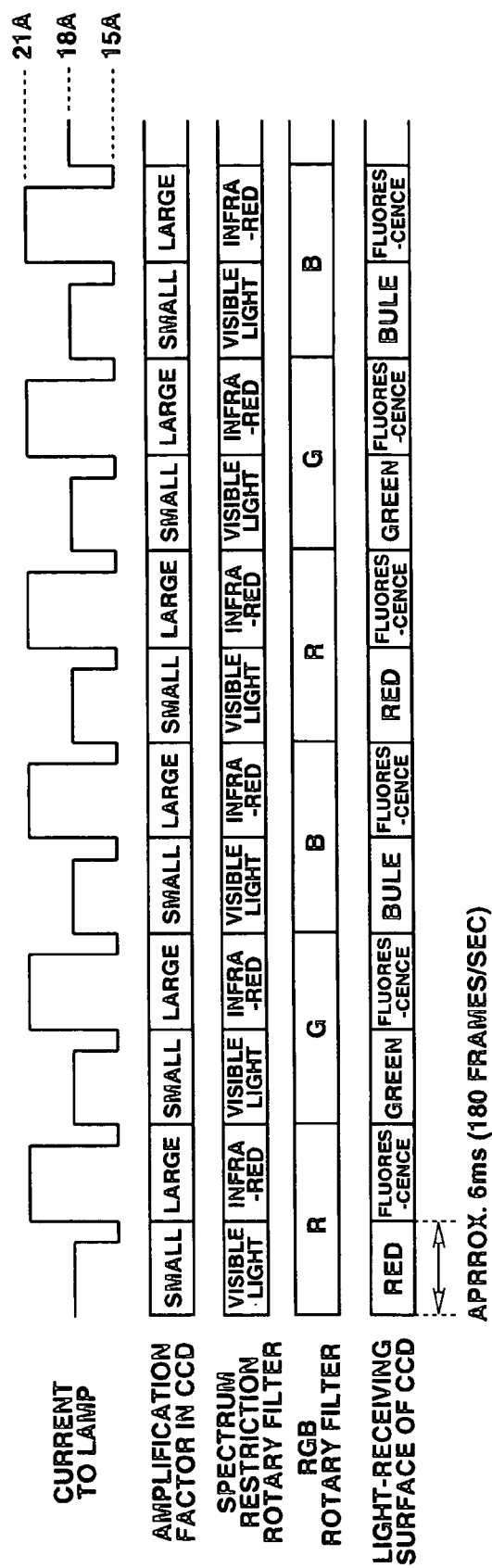

In fluorescence/normal light simultaneous observation, as shown in FIG. 51, the lamp light emission control circuit 153 supplies a pulsating current of 21 A or 18 A according to the position of the spectrum restriction rotary filter 111. The lamp 110 glows synchronously with the rotation of the RGB rotary filter 113.

The RGB rotary filter 113 is rotated 30 times per second and the spectrum restriction rotary filter 111 is rotated 90 times per second. Thus, red light, excitation light, green light, excitation light, blue light, and excitation light are irradiated successively (See FIG. 51).

At this time, the timing control circuit 134 gives control so that the RGB rotary filter 113 and spectrum restriction rotary filter 111 will rotate mutually synchronously. The lamp light emission control circuit 153 gives control so as to supply a given current to the lamp 110 responsively to switching of the portions of the spectrum restriction rotary filter 111.

As mentioned above, a larger current than the current to be supplied in normal light observation is supplied in fluorescence observation. Thus, the intensity of fluorescence can be increased, and a bright fluorescence image can be produced.

Reflected light and fluorescence stemming from the examined object 119 are passed by the diaphragm 152 for restricting an amount of light and excitation light cutoff filter 123, and imaged by the CCD 151. The excitation light cutoff filter 123 is designed to cut off excitation light components for exciting the antibody labeled by ICG and transmit fluorescence components and visible-light components. The excitation light cutoff filter 123 exhibits the spectroscopic characteristic of transmission shown in FIG. 38. The CCD 151 therefore receives red, green, and blue visible light rays or infrared fluorescence according to the positions of the RGB rotary filter 113 and spectrum restriction rotary filter 111.

The CCD 151 employed in this embodiment can provide a high amplification factor owing to an avalanche effect. The amplification factor is controlled on the basis of the amplitude of a clock. Since amplification is achieved inside the CCD 151, the amplification is little affected by an extraneous noise. When the amplification factor is raised by increasing the amplitude of the clock, even if light stemming from a region is feeble, the region can be observed brightly.

The CCD 151 is driven synchronously with the rotations of the rotary filters 111 and 113 by means of the CCD drive circuit 154. Depending on whether or not the spectrum restriction rotary filter 111 is rotated, the CCD 151 forms 180 frame images or 90 frame images per second. When the visible light transmission filter 111a of the spectrum restriction rotary filter 111 is inserted (in normal light observation), the CCD drive circuit 154 reduces the amplitude of the clock so as to lower the amplification factor in the CCD 151 (See FIGS. 49 and 51).

In observation using normal light, a relatively bright image can be produced. A low amplification factor will therefore do. When the infrared light transmission filter 111b is inserted (in fluorescence observation), the amplitude of the clock is increased in order to raise the amplification factor in the CCD 151 (See FIGS. 50 and 51).

By raising the amplification factor, even a region from which feeble fluorescence originates can be observed at sufficient brightness.

An electric signal output from the CCD 151 is input to and amplified by the preamplifier 124 in the processor 104C. The gain of the signal is controlled by the AGC circuit 125. Thereafter, the signal is input to the A/D conversion circuit 126 and converted into a digital signal.

The digital signal is stored in the first frame memory 128 or second frame memory 129 selected by the multiplexer 127. Based on a control signal sent from the timing control circuit 134, when the visible light transmission filter 111a of the spectrum restriction rotary filter 111 is inserted to the optical path, the multiplexer 127 selects the first frame memory 128. When the infrared light transmission filter 111b is inserted thereto, the multiplexer 127 selects the second frame memory 129.

Signals output from the first and second frame memories 128 and 129 are input to the image processing circuit 130 and subjected to image processing such as image enhancement and noise elimination. A resultant signal is then input to the display control circuit 131 and thus controlled for simultaneous display of a fluorescence image, a normal light image, and character information.

A digital signal output from the image display control circuit 131 is input to the D/A conversion circuit 132 and converted into an analog signal. The analog signal is then output to the monitor 105. The automatic light adjustment circuit 133 sends a signal for use in controlling the illumination light diaphragm 112 so that illumination light of proper brightness can be irradiated. The timing control circuit 134 synchronizes and controls rotations of the rotary filters, drive of the CCD, processing of various video signals, and glowing of the lamp.

In this embodiment, the single lamp 110 is employed as a light source for observation. Alternatively, two or more light sources, for example, a halogen lamp for normal line observation and a laser or light-emitting diode for use in exciting a fluorescent substance may be used in combination.

Moreover, illumination light for use in exciting a fluorescent substance may be irradiated in vitro.

Moreover, a means for controlling an amount of illumination light is not limited to the mechanism for varying a current to be supplied to the lamp. Alternatively, the opening provided by an illumination light diaphragm may be controlled or a filter for restricting an amount of light may be inserted to the path of illumination light.

Moreover, the position of the CCD 151 is not limited to the position in the distal part 117 of the insertional part 7. Alternatively, the CCD 151 may be incorporated in the processor 104C, and light may be introduced over an image guide fiber. Otherwise, the CCD 151 may be incorporated in the camera head attachable or detachable to or from the optical endoscope.

This embodiment has the advantage described below.

An amount of light emanating from the lamp and an amplification factor in the CCD 151 are controlled responsively to switching of fluorescence observation and normal light observation. It will not take place that a fluorescence image and normal light image are mutually greatly different in brightness. Both fluorescence and normal light can be observed at proper brightness Next, the tenth embodiment of the present invention will be described.

An object of this embodiment is to provide a fluorescent endoscope system capable of removing light, which leaks in from outside during fluorescence observation, and producing a fluorescence image little affected by a noise.

This embodiment is configured similarly to the seventh embodiment. Differences will be described mainly. The same reference numerals will be assigned to components having similar functions. The description of the components will be omitted.

Figure 52:
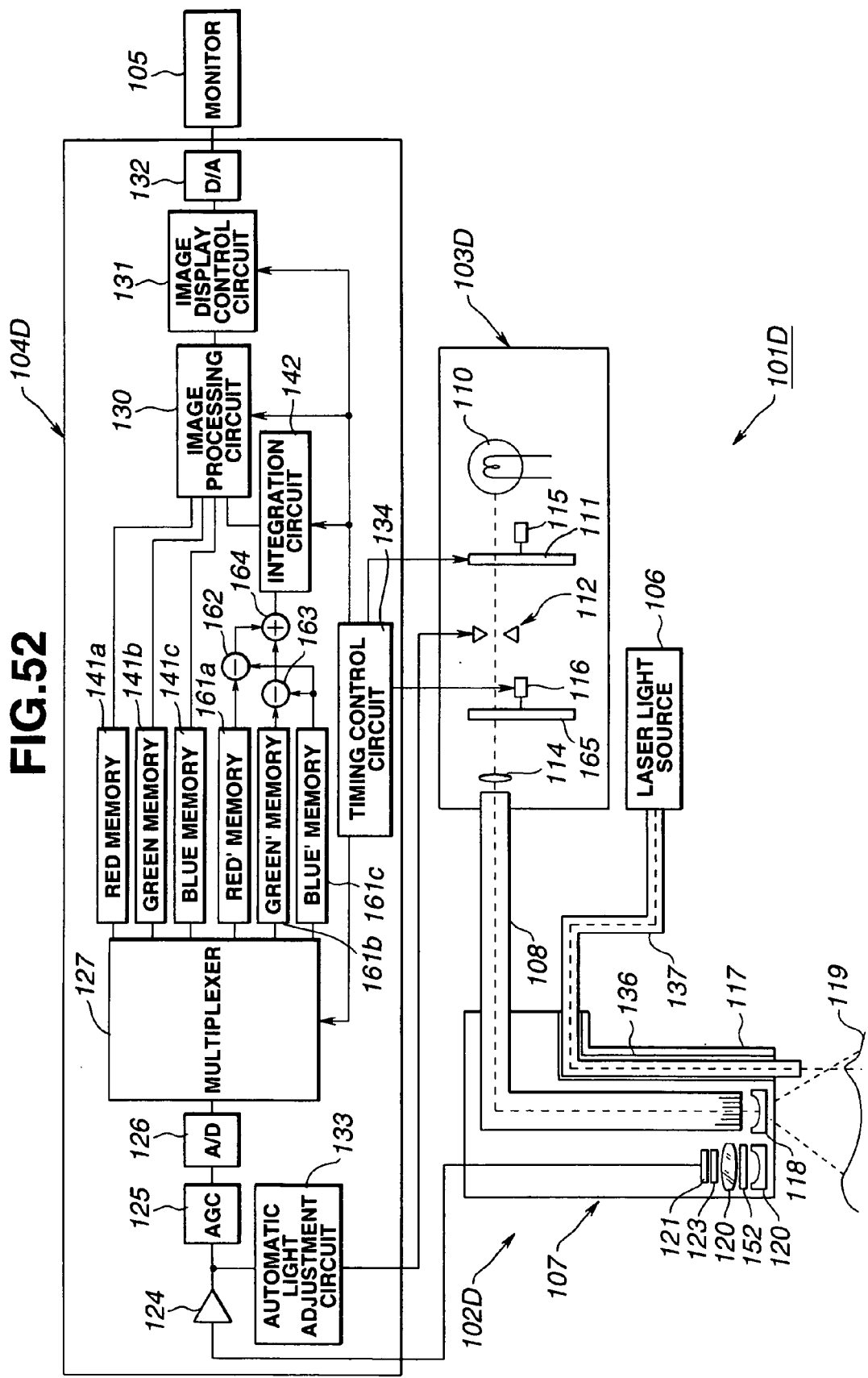

A fluorescent endoscope system 101D of the tenth embodiment shown in FIG. 52 is different from the fluorescent endoscope system 101A shown in FIG. 31 in points that an electronic endoscope 102D adopts a diaphragm 152 in place of the filter diaphragm 122 included in the electronic endoscope 102A, that a processor 104D has a red memory 141*a*, green memory 141*b*, blue memory 141*c*, red' memory 161*a*, green' memory 161*b*, and blue' memory 161*c* in place of the first frame memory 128 and second frame memory 129 included as the output stage of the multiplexer in the processor 104A, and includes two subtracters 162 and 163, an adder 164, and an integration circuit 142, and that a light source apparatus 103D employs an RGB rotary filter 165 having a characteristic different from the characteristic of the RGB rotary filter 113 included in the light source apparatus 103A.

The light source apparatus 103D includes, like the one shown in FIG. 31, the lamp 110 for radiating light, the spectrum restriction rotary filter 111 located on the path of illumination light for restricting the wavelengths of transmitted light, the illumination light diaphragm 112 for restricting an amount of light, and the RGB rotary filter 165 having a characteristic different from the characteristic of the RGB rotary filter 113 shown in FIG. 31 and restricting the wavelengths of transmitted light.

Figure 53:
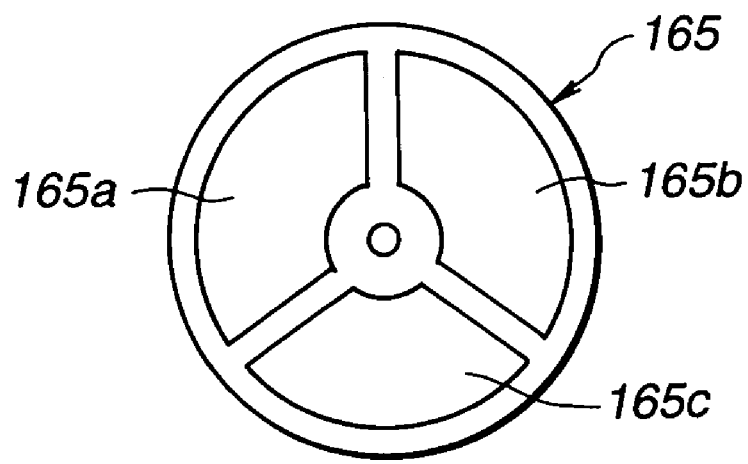

The spectrum restriction rotary filter 111 is, as shown in FIG. 32, bisected into the visible light transmission filter 111*a* and infrared light transmission filter 111*b*. The RGB rotary filter 165 is, as shown in FIG. 53, trisected into a red, green, and blue filters 165*a*, 165*b*, and 165*c*. The electronic endoscope 102D includes the light guide fiber 108 over which illumination light is propagated, the diaphragm 152 for restricting an amount of light falling on an imaging means, the excitation light cutoff filter 123 for removing excitation light, and the CCD 121.

The processor 104D includes the preamplifier 124, AGC circuit 125, A/D conversion circuit 126, multiplexer 127, red memory 141*a*, green memory 141*b*, blue memory 141*c*, red' memory 161*a*, green' memory 161*b*, blue' memory 161*c*, two subtracters 162 and 163, adder 164, integration circuit 142, image processing circuit 130, image display control circuit 131, D/A conversion circuit 132, automatic light adjustment circuit 133 for controlling the illumination light diaphragm 112, and timing control circuit 134 for synchronizing all the components of the fluorescent endoscope system 101D.

Moreover, the laser light source 106 for generating laser light for the purpose of laser therapy and the laser guide 137 over which laser light is introduced are included.

Next, the operations of the fluorescent endoscope system 101D having the foregoing components will be described.

A fluorescent substance having an affinity for a lesion such as a carcinoma, such as, an antibody labeled by indocyanine green (ICG) is administered to the examined object 119.

Light with wavelengths in a spectrum including the visible spectrum and the spectrum of wavelengths of excitation light for exciting the antibody labeled by ICG is radiated from the lamp 110 in the light source apparatus 103D. The light radiated from the lamp 110 is passed by the spectrum restriction rotary filter 111 and illumination light diaphragm 112, and transmitted by the RGB rotary filter 165.

Figure 54:
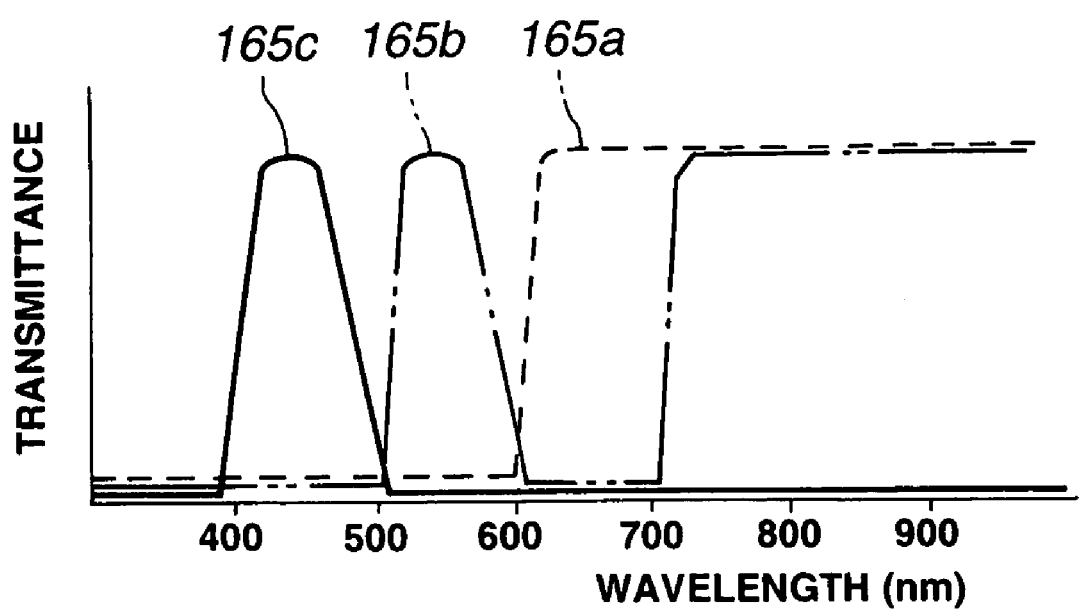

The light transmitted by the RGB rotary filter 165 falls on the light guide fiber 108 of the electronic endoscope 102D. The spectrum restriction rotary filter 111 has the structure shown in FIG. 32, and exhibits the spectroscopic characteristics of transmission shown in FIG. 33. The RGB rotary filter 165 has the structure shown in FIG. 53, and exhibits the spectroscopic characteristics of transmission shown in FIG. 54.

Specifically, the red filter 165*a* and green filter 165*b* transmit excitation light components of infrared light for exciting an antibody labeled by ICG, but the blue filter 165*c* does not transmit the excitation light components. When the infrared light transmission filter 111*b* of the spectrum restriction rotary filter 111 is inserted to the path of illumination light, if the red filter 165*a* or green filter 165*b* is inserted, the excitation light components are irradiated. However, if the blue filter 165*c* is inserted, no light is irradiated.

In normal light observation, the visible light transmission filter 111*a* of the spectrum restriction rotary filter 111 is locked on the optical path, and the RGB rotary filter 165 is rotated 30 times per second. Thus, red, green, and blue light rays are irradiated successively (See FIG. 55).

In fluorescence observation, the infrared light transmission filter 111*b* of the spectrum restriction rotary filter 111 is locked on the optical path, and the RGB rotary filter 165 is rotated 30 times per second. Thus, infrared light with wavelengths in the spectrum of wavelengths of excitation light is irradiated intermittently (See FIG. 56).

In fluorescence/normal light simultaneous observation, the RGB rotary filter 165 is rotated 30 times per second and the spectrum restriction rotary filter 111 is rotated 90 times per second. Thus, red light, excitation light, green light, excitation light, blue light, and excitation light are irradiated in that order (See FIG. 57).

At this time, the timing control circuit 134 gives control so that the RGB rotary filter 165 and spectrum restriction rotary filter 111 can be rotated synchronously.

Reflected light and fluorescence stemming from the examined object 119 are passed by the diaphragm 152 for restricting an amount of light and the excitation light cutoff filter 123, and then imaged by the CCD 121. The excitation light cutoff filter 123 is designed to cut off excitation light components for exciting an antibody labeled by ICG and to transmit fluorescence components and visible light components. The diaphragm 152 exhibits the spectroscopic characteristic of transmission shown in FIG. 38.

The CCD 121 therefore receives red, green, and blue visible light rays, fluorescence of infrared light, or light leaking in from outside the body and resulting in a noise according to the positions of the RGB rotary filter 165 and spectrum restriction rotary filter 111 (See FIGS. 55 to 57).

The CCD 121 is driven synchronously with the rotations of the rotary filters 111 and 165 by means of a CCD drive circuit that is not shown, and forms 180 frame images or 90 frame images per second depending on whether or not the spectrum restriction rotary filter 111 is rotated.

An electric signal output from the CCD 121 is input to and amplified by the preamplifier 124 in the processor 104D. The gain of the signal is controlled by the AGC circuit 125. Thereafter, the signal is input to the A/D conversion circuit 126 and converted into a digital signal.

The digital signal is stored in any of the six frame memories 141a to 141c and 161a to 161c selected by the multiplexer 127. The multiplexer 27 selects a memory, in which an image is stored, on the basis of a control signal sent from the timing control circuit 134.

When the visible light transmission filter 111a of the spectrum restriction rotary filter 111 is inserted to the path of illumination light, an image signal is stored in the red memory 141a, green memory 141b, or blue memory 141c according to the position of the RGB rotary filter 165. In other words, an image formed under light irradiated through the red filter is stored in the red memory 141a, an image formed under light irradiated through the green filter is stored in the green memory 141b, and an image formed under light irradiated through the blue filter is stored in the blue memory 141c.

When the infrared light transmission filter 111b is inserted into the path of illumination light, an image signal is stored in the red' memory 161a, green' memory 161b, or blue' memory 161c according to the position of the RGB rotary filter 165. In other words, a fluorescence image is stored in the red' memory 161a or green' memory 161b, and an image (background image) formed without illumination light is stored in the blue' memory 161c.

The background image is represented by a noise derived from light leaking in from outside the body and a stationary noise inherent to an equipment. The background noises do not pose a very serious problem during normal light observation, but pose a serious problem when feeble fluorescence is observed.

In particular, light with wavelengths in the near infrared spectrum is well-transmitted by a living tissue because it is little absorbed by hemoglobin or water. When fluorescence with wavelengths in the near infrared spectrum like fluorescence emanating from an antibody labeled by ICG is observed, mixture of leakage light coming from outside a subject poses a problem.

The two subtracters 162 and 163 subtract a background image from a fluorescence image, whereby the above background noises are removed. Two fluorescence images from which the background noises are removed are added up by the adder 164. A resultant signal is input to the integration circuit 142 having the configuration shown in FIG. 46. A noise that is temporally unsteady is thus eliminated.

Signals output from the red memory 141a, green memory 141b, blue memory 141c, and integration circuit 142 are input to the image processing circuit 130, and subjected to image processing such as image enhancement and noise elimination. The resultant signal is input to the image display control circuit 131 and controlled for simultaneous display of a fluorescence image, a normal light image, and character information.

A digital signal output from the image display control circuit 131 is input to the D/A conversion circuit 132 and converted into an analog signal. The analog signal is then output to the monitor 105. The automatic light adjustment circuit 133 sends a signal for use in controlling the illumination light diaphragm 112 so that illumination light of proper brightness can be irradiated. The timing control circuit 134 synchronizes and controls rotations of the rotary filters, drive of the CCD, and processing of various video signals.

On the monitor 105, depending on the position of the spectrum restriction rotary filter 111, a normal light image or fluorescence image can be displayed or both of the images can be displayed simultaneously.

In this embodiment, the single lamp 110 is used as a light source for observation. Alternatively, two or more light sources, for example, a halogen lamp for normal light observation and a laser or light-emitting diode for use in exciting a fluorescent substance may be used in combination.

Moreover, illumination light for exciting a fluorescent substance may be irradiated in vitro.

Moreover, the position of the CCD 121 is not limited to the position in the distal part 117 of the insertional part 107. Alternatively, the CCD 121 may be incorporated in the processor 104D, and light may be introduced over an image guide fiber. Otherwise, the CCD 121 may be incorporated in a camera head attachable or detachable to or from an optical endoscope.

Moreover, processing may be carried out field by field instead of frame by frame.

This embodiment has the advantage described below.

Since a background image formed without irradiation of light is subtracted from a fluorescence image formed with irradiation of excitation light, a fluorescence image little affected by a noise derived from light leaking in from outside can be produced.

Next, the eleventh embodiment of the present invention will be described. An object of this embodiment is to provide a fluorescent endoscope system capable of offering image quality, which is good enough to permit easy observation and thus facilitate diagnosis, in either normal light observation or fluorescence observation.

Figure 58:
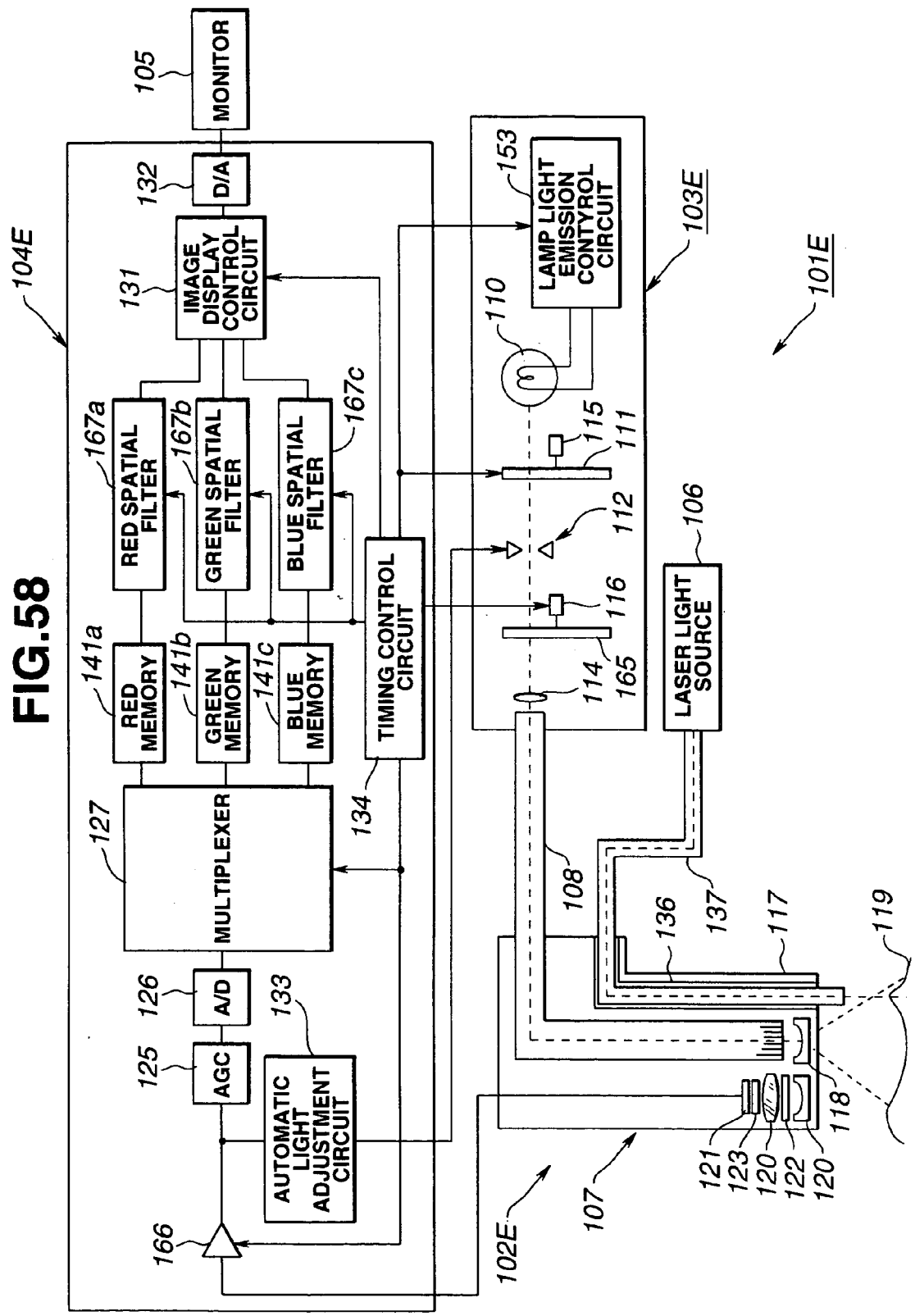

A fluorescent endoscope system 101E of the eleventh embodiment shown in FIG. 58 is different from the fluorescent endoscope system 101A shown in FIG. 31 in points that a light source apparatus 103E includes, in addition to the components of the light source apparatus 103A, a lamp light emission control circuit 153 for controlling glowing of the lamp 110, and that a processor 104E has a variable preamplifier 166 whose amplification factor is variable in place of the preamplifier included in the processor 104A, has red, green, and blue memories 141a, 141b, and 141c in place of the first and second frame memories 128 and 129, and has red, green, and blue spatial filters 167a, 167b, and 167c in place of the image processing circuit 130.

The spectrum restriction rotary filter 111 has the structure shown in FIG. 32, and exhibits the spectroscopic characteristics of transmission shown in FIG. 33. The RGB rotary filter 113 has the structure shown in FIG. 34, and exhibits the spectroscopic characteristics of transmission shown in FIG. 35.

Next, the operations of the fluorescent endoscope system 101E having the foregoing components will be described.

A fluorescent substance having an affinity for a lesion such as a carcinoma, such as, an antibody labeled by ICG is administered in advance to the examined object 119.

In normal light observation, the visible light transmission filter 111a of the spectrum restriction rotary filter 111 is locked on the optical path, and the RGB rotary filter 113 is rotated 30 times per second. Thus, red, green, and blue light rays are irradiated successively (See FIG. 49).

In fluorescence observation, the infrared light transmission filter 111b of the spectrum restriction rotary filter 111 is locked on the optical path, and the RGB rotary filter 113 is rotated 30 times per second. Thus, infrared light with wavelengths in the spectrum of wavelengths of excitation light is irradiated (FIG. 50).

In this embodiment, the mode of fluorescence/normal light simultaneous observation is not implemented in an attempt to simplify the configuration of memories and reduce cost. The lamp light emission control circuit 153 gives control so that a current to be supplied to the lamp 110 varies responsively to the change of positions of the spectrum restriction rotary filter 111. A larger current than a current to be supplied in normal light observation is supplied in fluorescence observation, whereby the intensity of fluorescence can be increased. This results in a bright fluorescence image.

Reflected light and fluorescence stemming from the examined object 119 is passed by the diaphragm 152 for restricting an amount of light and the excitation light cutoff filter 123, and then imaged by the CCD 121. The excitation light cutoff filter 123 is designed to cut off excitation light components for exciting an antibody labeled by ICG and to transmit fluorescence components and visible light components. The excitation light cutoff filter 123 exhibits the spectroscopic characteristic of transmission shown in FIG. 38. The CCD 121 therefore receives red, green, and blue visible light rays or infrared fluorescence according to the positions of the RGB rotary filter 113 and spectrum restriction rotary filter 111.

An electric signal output from the CCD 121 is input to and amplified by the variable preamplifier 166 in the processor 104E. The gain of the signal is controlled by the AGC circuit 125.

The amplification factor in the variable preamplifier 166 employed in this embodiment can be varied and is controlled with a control signal input over an external control line. The variable preamplifier 166 is controlled synchronously with the rotation of the spectrum restriction rotary filter 111 in response to a control signal output from the timing control circuit 134. When the visible light transmission filter 111a of the spectrum restriction rotary filter 111 is inserted to the optical path (in normal light observation), the amplification factor is lowered. When normal light is imaged for observation, since a relatively bright image is produced, a low amplification factor will do. When the infrared light transmission filter 111b is inserted (in fluorescence observation), the amplification factor in the variable preamplifier 166 is raised. With a higher amplification factor, even a region from which feeble fluorescence originates can be observed at sufficient brightness.

Thereafter, the signal is input to the A/D conversion circuit 126 and converted into a digital signal. The digital signal is stored in the red memory 141a, green memory 141b, or blue memory 141c selected by the multiplexer 127.

Based on a control signal sent from the timing control circuit 134, the multiplexer 127 selects the red memory 141a when the red filter 113a of the RGB rotary filter 113 is inserted to the optical path, selects the green memory 141b when the green filter 113b is inserted thereto, and selects the blue memory 141c when the blue filter 113c is inserted thereto.

Signals output from the red, green, and blue memories 141a, 141b, and 141c are input to the red, green, and blue spatial filters 167a, 167b, and 167c respectively, and subjected to image processing such as image enhancement (contour enhancement) or noise elimination.

The spatial filters 167a, 167b, and 167c execute convolution for two-dimensional image data using a window of 5 by 5 in size. Each of the spatial filters 167a, 167b, and 167c has a plurality of coefficient registers therein. Coefficients can be rewritten or changed from one to another in response to a control signal.

The timing control circuit changes coefficients synchronously with the change of the position of the spectrum restriction rotary filter 111. For example, when the infrared light transmission filter 111b is inserted to the optical path (in fluorescence observation), coefficients permitting smoothing of an image like the one shown in FIG. 59 are set. A fluorescence image that is unprocessed is affected by a noise because of a low signal-to-noise ratio. By carrying out the smoothing, the fluorescence image can be viewed without the adverse effect of a noise.

When the visible light transmission filter 111a of the spectrum restriction rotary filter 111 is inserted to the optical path (in normal light observation), coefficients permitting sharpening of an image like the one shown in FIG. 60 are set. When normal light is imaged for observation, a relatively bright image is produced. In this case, the image is little affected by a noise because of a good signal-to-noise ratio. A sharpening filter enabling clear vision of even the microscopic structure of a lesion will therefore prove effective.

Image signals output from the spatial filters are input to the image display control circuit 131, and controlled for display, for example, synthesized with character information. A digital signal output from the image display control circuit 131 is input to the D/A conversion circuit 132 and converted into an analog signal. The analog signal is output to the monitor 105.

The automatic light adjustment circuit 133 sends a signal for use in controlling the illumination light diaphragm 112 so that illumination light of proper brightness can be irradiated. The timing control circuit 134 synchronizes and controls rotation of the RGB rotary filter 113, change of the position of the spectrum restriction rotary filter 111, drive of the CCD, processing of various video signals, and glowing of the lamp.

On the monitor 105, either of a normal light image and fluorescence image can be viewed depending on the position of the spectrum restriction rotary filter 111.

In this embodiment, coefficients of each of the spatial filters 167a, 167b, and 167c are set so that the sum thereof will be 1. Alternatively, the coefficients may be set so that the sum thereof will be larger than 1. In this case, the spatial filters 167a, 167b, and 167c are provided with an amplification function. Otherwise, the coefficients may be set according to the position of the rotary filter 111 so that the sum thereof will be larger in fluorescence observation than in normal light observation.

A light source for observation is not limited to the single lamp 110. Alternatively, two or more light sources, for example, a halogen lamp for normal light observation and a laser or light-emitting diode for use in exciting a fluorescent substance may be used in combination.

Moreover, illumination light for exciting a fluorescent substance may be irradiated in vitro.

Moreover, a means for controlling an amount of illumination light is not limited to the mechanism for varying a current to be supplied to the lamp. Alternatively, the opening provided by an illumination light diaphragm may be controlled or a filter for restricting an amount of light may be inserted to the path of illumination light.

Moreover, the position of the CCD 121 is not limited to the position in the distal part of the insertional part of the electronic endoscope 102E. Alternatively, the CCD 121 may be incorporated in the processor 104E, and light may be introduced over the image guide fiber. Otherwise, the CCD 121 may be placed in a camera head attachable or detachable to or from the optical endoscope.

Moreover, processing may be carried out field by field instead of frame by frame.

According to this embodiment, the amplification factor in the variable preamplifier 166 or an amount of illumination light is controlled responsively to switching of fluorescence observation and normal light observation. It will therefore not take place that a fluorescence image and normal light image are markedly different in brightness. An object from which fluorescence and normal light originate can be observed at proper brightness.

Moreover, coefficients to be set in each of the spatial filters 167a, 167b, and 167c are changed responsively to switching of fluorescence observation and normal light observation. A fluorescence image is produced as an image little affected by a noise, and a normal light image is produced as an image showing even the microscopic structure of an object clearly. Thus, the object can be observed using an appropriate image.

Finally, embodiments constructed by combining parts of the aforesaid plurality of embodiments belong to the present invention.

What is claimed is:

1. An endoscope system for imaging an object in a living body, comprising:
   a light source for radiating irradiation light to said object to produce reflected and flourescent light;
   an endoscope having an elongated insertion part capable of being inserted into said living body;
   a solid-state imaging device having a variable amplification factor being variable without loss of resolution and provided to said endoscope for receiving said reflected and fluorescent light and outputting a variable amplitude related signal;
   a signal processor for processing said output signal from said solid-state imaging device and producing a video signal;
   a display device for receiving said video signal and displaying an image represented by said video signal;
   a controller for controlling said amplification factor in said solid-state imaging device in response to said reflected and fluorescent light to provide greater amplification for said received fluorescent light than for said received reflected light;
   a variable light diaphragm in an optical path linking said light source means and said object and controllable based on said output signal from said solid-state imaging device to pass greater or lesser amounts of light from said light source means, and
   a switching device for switching said irradiation light from said light source to provide a first spectrum to excite a fluorescent substance contained in said object and a second spectrum including at least a part of a spectrum of visible light; and
   a wavelength limiter in an optical path linking said object and said solid-state imaging device for preventing transmission of light with wavelengths in said first spectrum and permitting transmission of light with wavelengths in at least a part of a fluorescent spectrum of said fluorescent substance and in at least a part of said second spectrum.

2. An endoscope system for imaging an object in a living body, comprising:
   a light source for radiating irradiation light in at least a visible and non-visible spectrum to said object to produce reflected and fluorescent light;
   a light switching device in an optical path between said light source and said object for switching between said visible and non-visible spectrum to irradiate said object;
   an endoscope having an elongated insertion part capable of being inserted into said living body and operable to collect said reflected and fluorescence light;
   a solid-state imaging device coupled to said endoscope for receiving said reflected and fluorescence light collected by said endoscope, said solid-state imaging device being provided at a distal end of the insertion part of the endoscope and having an amplification function that serves to amplify a signal subjected to a photoelectric conversion inside the solid-state imaging device, and effective to provide a variable amplification factor and a variable amplitude output related to said received light in said visible spectrum and a value of said amplification factor;
   a signal processor coupled to said solid-state imaging device for processing said output from said solid-state imaging device and producing a video signal;
   a display device coupled to said signal processor for receiving said video signal and displaying an image represented by said video signal;
   a controller for controlling said amplification factor in said solid-state imaging device to provide greater amplification for said received fluorescence light than for said received reflected light; and
   a light source controller for controlling power supplied to said light source in relation to a switching state of said light switching device, such that said light source operates at higher power when said non-visible spectrum is switched to irradiate said object than when said visible spectrum is switched to irradiate said object.

3. An endoscope system according to claim 2, further comprising a wavelength limiter in an optical path linking said object and said solid-state imaging device for preventing transmission of light with wavelengths in said non-visible spectrum and permitting transmission of at least a portion of said reflected and fluorescence light.

4. An endoscope system according to claim 2, wherein said non-visible light spectrum is operable to excite a fluorescent substance introduced into said object to produce said fluorescence light.

5. An endoscope system according to claim 4, further comprising a variable light diaphragm in an optical path linking said light source and said object and controllable based on said output from said solid-state imaging device to pass greater or lesser amounts of light from said light source.

6. An endoscope system, comprising:
   a light source apparatus including a light for radiating light to an object and a first filter unit provided on an illumination path linking the light source and the object and including plural filters through which visible light having different spectra are successively irradiated to the object;
   an endoscope having an elongated insertion part capable of being inserted into a living body;
   a solid-state imaging device having a variable amplification factor provided to the endoscope for controlling an image brightness of a fluorescence image, the amplification factor being varied without loss of resolution, and said solid-state imaging device being provided at a distal end of the insertion part of the endoscope and having an amplification function that serves to amplify a signal subjected to a photoelectric conversion inside the solid-state imaging device;
   a signal processor for processing a signal output from the solid-state imaging device and producing a video signal;

a display device for displaying an image represented by the video signal;

a controller for controlling the amplification factor in the solid-state imaging device based on visible light received by the imaging device; and a second filter unit provided on the illumination path and including an infrared light transmission filter to produce fluorescent light.

7. An endoscope system according to claim 6, wherein the first filer unit transmits visible light to produce reflected light, and the display device can display a normal light image by the reflected light and a fluorescent light image by fluorescent light.

8. The endoscope system according to claim 7, wherein said first filter unit includes red, green and blue filters.

9. The endoscope system according to claim 7, wherein said variable amplification factor is varied based on an amplitude of a periodical signal controlled by said controller.

10. The endoscope system according to claim 7, wherein said controller controls said amplitude of said periodical signal depending on said spectrum irradiated to said object.

11. An endoscope system according to claim 7, wherein the solid-state imaging device receives both the reflected light and the fluorescent light without changing an optical path thereof.

12. An endoscope system according to claim 11, wherein the second filter unit further includes a visible light transmission filter for transmitting the visible light, and the controller controls an amplitude of a periodical signal in response to switching between the visible light transmission filter and the infrared light transmission filter.

13. An endoscope system according to claim 12, wherein the second filter unit is composed of a rotary filter, and the controller controls the amplification factor in the solid-state imaging device in correspondence with rotation of the second filter unit.

14. An endoscope system according to claim 12, wherein the second filter unit is provided between the first filter unit and the light.

15. An endoscope system according to claim 12, further comprising:

an amount-of-light controller for controlling amounts of the light, the amount-of-light controller controlling the amount of the light so as to operate the light with a higher output when irradiating excitation light to an object by the infrared light transmission filter than that when irradiating the visible light to the object by the visible light transmission filter.

16. An endoscope system according to claim 12, further comprising:

a variable light diaphragm provided in an illumination optical path for controlling amounts of illumination light irradiated to the object; and a diaphragm controller for controlling the variable light diaphragm, the diaphragm controller controlling the variable light diaphragm so that the amount of the light irradiated to the object when irradiating the excitation light to the object by the infrared light transmission filter may be greater than that when irradiating the visible light to the object by the visible light transmission filter.

17. An endoscope system according to claim 12, further comprising an amount-of light limiting filter that limits an amount of illumination light irradiated to the object when irradiating the visible light to the object by the visible light transmission filter.

18. An endoscope system, comprising:

a light source apparatus including a light for irradiating an object;

an endoscope having an insertion part capable of being inserted into a living body;

a solid-state imaging device for imaging an object in the living body by the endoscope, the solid-state imaging device having a variable amplification factor that is variable without loss of resolution and provided for receiving reflected light and fluorescent light without changing an optical path;

a filter unit provided on an illumination optical path between the light source and the object, the filter unit including a visible light transmission filter for transmitting visible light to the object to produce reflected light and an excitation light transmission filter for transmitting excitation light to produce fluorescent light;

an excitation light cutoff filter provided on an optical path linking the object and the solid-state imaging device for preventing transmission of the excitation light;

a filter switching device for providing the visible light transmission filter and the excitation light transmission filter selectively on the illumination light path to switch the illumination light irradiated to the object between the visible light and the excitation light;

a signal processor for processing an output signal from the solid-state imaging device;

a display device for displaying an image based on the signal processed by the signal processor, the display device is capable of displaying a normal light image by the reflected light and a fluorescent light image by the fluorescent light; and a controller for controlling an amplification factor in the solid-state imaging device, the controller controlling the amplification factor in correspondence with the switching of the filter switching device.

19. An endoscope system according to claim 18, further comprising:

an amount-of-light controller for controlling an amount of the light, the amount-of-light controller controlling the amount of the light so as to operate the light with a higher output when irradiating excitation light to an object by the excitation light transmission filter than that when irradiating the visible light to the object by the visible light transmission filter.

20. An endoscope system according to claim 19, wherein the visible light transmission filter and the excitation light transmission filter are provided in parallel with a direction of rotation of the filter unit.

21. An endoscope system according to claim 19, further comprising:

an RGB rotary filter provided on the illumination optical path, the RGB filter including red, green and blue filters.

22. An endoscope system according to claim 21, wherein the filter unit is provided between the light and the RGB filter.

23. An endoscope system according to claim 18, further comprising:

a variable light diaphragm provide in an illumination optical path for controlling amounts of illumination light irradiated to the object; and a diaphragm controller for controlling the variable light diaphragm, the diaphragm controller controlling the variable light diaphragm so that the amounts of the light irradiated to the object when irradiating the excitation light to the object by the excitation light transmission filter may be greater than that when irradiating the visible light to the object by the visible light transmission filter.

24. An endoscope system according to claim 23,
wherein the visible light transmission filter and the excitation light transmission filter are provided to parallel with a direction of rotation of the filter unit.

25. An endoscope system according to claim 23, further comprising:
an RGB rotary filter provided on the illumination optical path, the RGB filter including red, green and blue filters.

26. An endoscope system according to claim 25,
wherein the filter unit is provided between the light source and the RGB filter.

27. An endoscope system according to claim 18, further comprising an amount-of-light limiting filter limits an amount of illumination light irradiated to the object when irradiating the visible light to the object by the visible light transmission filter.

28. An endoscope system according to claim 27,
wherein the visible light transmission filter and the excitation light transmission filter are provided in parallel with a direction of rotation of the filter unit.

29. An endoscope system according to claim 27, further comprising:
an RGB rotary filter provided on the illumination optical path, the RGB filter including red, green and blue filters.

30. An endoscope system according to claim 29,
wherein the filter unit is provided between the light and the RGB filter.

31. An endoscope system, comprising:
a light source apparatus including a light for irradiating an object;
an endoscope having an insertion part capable of being inserted into a living body;
a solid-state imaging device for imaging an object in the living body by the endoscope, the solid-state imaging device having a variable amplification factor that is variable without loss of resolution;
a filter unit provided on an illumination optical path between the light source and the object, the filter unit including a visible light transmission filter for transmitting visible light to the object to produce reflected light and an excitation light to produce an image;
an excitation light cutoff filter provided on an optical path linking the object and the solid-state imaging device for preventing transmission of the excitation light;
a filter switching device for providing the visible light transmission filter and the excitation light transmission filter selectively on the illumination light path to switch the illumination light irradiated to the object between the visible light and the excitation light;
a signal processor for processing an output signal from the solid-state imaging device;
a display device for displaying an image based on the signal processed by the signal processor; the display device is capable of displaying a normal light image by the reflected light and a fluorescent light image by the fluorescent light; and a controller for controlling an amplification factor in the solid-state imaging device; the controller controlling the amplification factor in correspondence with the switching of the filter switching device.

32. An endoscope system according to claim 31, further comprising:
a variable light diaphragm provided in an illumination optical path for controlling amounts of illumination light irradiated to the object; and
a diaphragm controller for controlling the variable light diaphragm, the diaphragm controller controlling the variable light diaphragm so that the amounts of the light irradiated to the object when irradiating the excitation light to the object by the excitation light transmission filter may be greater than that when irradiating the visible light to the object by the visible light transmission filter.

33. An endoscope system according to claim 31,
wherein the visible light transmission filter and the excitation light transmission filter are provided in parallel with a direction of rotation of the filter unit.

34. An endoscope system according to claim 31, further comprising:
an RGB rotary filter provided on the illumination optical path, the RGB filter including red, green and blue fibers.

35. An endoscope system according to claim 34,
wherein the filter unit is provided between the light and the RGB filter.

36. An endoscope system according to claim 31, further comprising:
an amount-of-light controller for controlling an amount of the light, the amount-of-light controller controlling the amount of the light so as to operate the light with a higher output when irradiating excitation light to an object by the excitation light transmission filter than that when irradiating the visible light to the object by the visible light transmission filter.

37. An endoscope system according to claim 36,
wherein the visible light transmission filter and the excitation light transmission filter are provided in parallel with a direction of rotation of the filter unit.

38. An endoscope system according to claim 37,
wherein the filter unit is provided between the light and the RGB filter.

39. An endoscope system according to claim 36, further comprising:
an RGB rotary filter provided on the illumination optical path, the RGB filter including red, green and blue filters.

40. An endoscope system comprising:
a light source means including a light for irradiating an object;
an endoscope having an insertion part capable of being inserted into a living body;
an imaging means having a variable amplification factor that is variable without loss of resolution;
an illumination light switching means provided on an illumination optical path between the light source means and the object, the illumination light switching means being able to irradiate visible light to produce reflected light and excitation light to produce fluorescent light selectively to an object;

a switching means for switching the illumination light switching means to switch between a normal light observation by the visible light and a fluorescent light observation by the excitation light;

a signal processing means for processing an output signal from the imaging means;

a display means for displaying an image based on the signal processed by the signal processing means, the display means is capable of displaying a normal light image by the reflected light and a fluorescent light image by the fluorescent light; and an amplification controlling means for controlling an amplification factor of the imaging means, the amplification controlling means controlling the amplification factor in correspondence with the switching of the filter switching means.

41. An endoscope system according to claim 40, further comprising:

a diaphragm provided in an illumination optical path for controlling an amount of illumination light irradiated to the object; and a diaphragm controlling means for controlling the diaphragm, the diaphragm controlling means controlling the diaphragm so that the amount of the light irradiated to the object at the time of the fluorescent light observation may be greater than at the time of the normal light observation.

42. An endoscope system according to claim 41, further comprising:

an amount-of-light controlling means for controlling an amount of the light, the amount-of-light controlling means controlling the amount of the light so that the amount of light irradiated to the object at the time of the fluorescent light observation may be greater than that at the time of the normal light observation.

43. An endoscope system comprising:

a light source apparatus for radiating irradiation light to an object in a living body to produce reflected and fluorescent light;

an endoscope including a solid-state imaging device having a variable amplification factor for controlling an image brightness of a fluorescence image, the solid-state imaging device receiving the reflected and fluorescent light, and said solid-state imaging device being provided at a distal end of an insertion part of the endoscope and having an amplification function that serves to amplify a signal subjected to a photoelectric conversion inside the solid-state imaging device;

a signal processor for processing a signal output from the solid-state imaging device and producing a video signal;

a controller for controlling the amplification factor in the solid-state imaging device based on the visible light received by the imaging device;

a switching device for switching the irradiation light from the light source apparatus to provide a first spectrum to excite a fluorescent substance contained in the object and a second spectrum including at least a part of a spectrum of visible light; and a wavelength limiter in an optical path linking the object and the solid-state imaging device for preventing transmission of light with wavelengths in the first spectrum and permitting transmission of light with wavelengths in at least a part of a fluorescent spectrum of the fluorescent light and in at least a part of the second spectrum.

44. An endoscope system comprising:

a light source apparatus for radiating irradiation light in at least a visible and non-visible spectrum to an object in a living body to produce reflected and fluorescent light, the light source apparatus including a light;

an irradiation light switching device in an optical path between the light and the object for switching between the visible and non-visible spectrum to irradiate the object;

an endoscope including a solid-state imaging device for receiving the reflected and fluorescent light, the solid-state imaging device having a variable amplification factor for controlling an image brightness of a fluorescence image, and said solid-state imaging device being provided at a distal end of an insertion part of the endoscope and having an amplification function that serves to amplify a signal subjected to a photoelectric conversion inside the solid-state imaging device;

a signal processor for processing a signal output from the solid-state imaging device and producing a video signal;

a controller for controlling the amplification factor in the solid-state imaging device based on visible light received by the imaging device; and a light controller for controlling power supplied to the light in relation to a switching state of the irradiation light switching device, such that the light operates at higher power when the non-visible spectrum is switched to irradiate the object than when the visible spectrum is switched to irradiate the object.

45. An endoscope system comprising:

a light source apparatus including a light for radiating light to an object and a first filter unit provided on an illumination path linking the light and the object and including plural filters through which visible light having different spectra are successively irradiated to the object;

an endoscope including a solid-state imaging device having a variable amplification factor for controlling an image brightness of a fluorescence image, and said solid-state imaging device being provided at a distal end of an insertion part of the endoscope and having an amplification function that serves to amplify a signal subjected to a photoelectric conversion inside the solid-state imaging device;

a signal processor for processing a signal output from the solid-state imaging device and producing a video signal;

a controller for controlling the amplification factor in the solid-state imaging device based on visible light received by the imaging device; and a second filter unit provided on the illumination path and including an excitation light transmission filter to produce fluorescent light.

46. An endoscope system comprising:

a light source apparatus including a light for irradiating an object;

an endoscope including a solid-state imaging device having a variable amplification factor, the solid-state imaging device receiving the reflected and fluorescent light without changing an optical path;

a filter unit provided on an illumination optical path between the light and the object, the filter unit including a visible light transmission filter for transmitting visible light to the object to produce reflected light and an excitation light transmission filter for transmitting excitation light to produce fluorescent light;

an excitation light cutoff filter provided on an optical path linking the object and the solid-state imaging device for preventing transmission of the excitation light;

a filter switching device for providing the visible light transmission filter and the excitation light transmission filter selectively on the illumination light path to switch the illumination light irradiated on the object between the visible light and the excitation light;

a signal processor for processing an output signal from the solid-state imaging device; and a controller for controlling an amplification factor in the solid-state imaging device for controlling an image brightness of a fluorescence image based on visible light received by the imaging device, and said solid-state imaging device being provided at a distal end of an insertion part of the endoscope and having an amplification function that serves to amplify a signal subjected to a photoelectric conversion inside the solid-state imaging device.

47. An endoscope system comprising:

a light source apparatus including a light for irradiating an object;

an endoscope including a solid-state imaging device having a variable amplification factor;

a filter unit provided on an illumination optical path between the light and the object, the filter unit including a visible light transmission filter for transmitting visible light to the object to produce reflected light and an excitation light transmission filter for transmitting excitation light to produce fluorescent light;

an excitation light cutoff filter provided on an optical path linking the object and the solid-state imaging device for preventing transmission of the excitation light;

a filter switching device for providing the visible light transmission filter and the excitation light transmission filter selectively on the illumination light path to switch the illumination light irradiated to the object between the visible light and the excitation light;

a signal processor for processing an output signal from the solid-state imaging device; and a controller for controlling an amplification factor in the solid-state imaging device for controlling an image brightness of a fluorescence image based on visible light received by the imaging device, and said solid-state imaging device being provided at a distal end of an insertion part of the endoscope and having an amplification function that serves to amplify a signal subjected to a photoelectric conversion inside the solid-state imaging device.

48. An endoscope system comprising:

a light source means including a light for irradiating an object to produce reflected and fluorescent light;

an endoscope including an imaging means having a variable amplification factor for controlling an image brightness of a fluorescence image, and said imaging device being provided at a distal end of an insertion part of the endoscope and having an amplification function that serves to amplify a signal subjected to a photoelectric conversion inside the imaging device;

an illumination light switching means provided on an illumination optical path between the light and the object, the illumination light switching means being able to irradiate visible light to produce reflected light and excitation light to produce fluorescent light selectively to the object;

a switching means for switching the illumination light switching means to switch between a normal light observation by the visible light and a fluorescent light observation by the excitation light;

a signal processing means for processing an output signal from the imaging means; and an amplification controlling means for controlling the amplification factor of the imaging means based on visible light received by the imaging device.

49. An endoscope system comprising:

a light source apparatus including a light for irradiating an object to produce reflected and fluorescent light;

an endoscope including a solid-state imaging device having a variable amplification factor for controlling an image brightness of a fluorescence image, and said solid-state imaging device being provided at a distal end of an insertion part of the endoscope and having an amplification function that serves to amplify a signal subjected to a photoelectric conversion inside the solid-state imaging device;

a filter unit provided on an illumination path between the light and the object, the filter unit including an excitation light transmission filter for transmitting excitation light to the object to produce fluorescent light;

a switching device that switches the irradiation light from the light source apparatus to produce the reflected light or the fluorescent light by selectively providing the excitation light transmission filter on the illuminating path;

a signal processor for processing an output signal from the solid-state imaging device; and a controller for controlling an amplification factor in the solid-state imaging device based on visible light received by the imaging device.

* * * * *